United States Patent
Shi et al.

(10) Patent No.: US 8,524,703 B2
(45) Date of Patent: Sep. 3, 2013

(54) BRIDGEHEAD AMINE RING-FUSED INDOLES AND INDOLINES

(75) Inventors: Lei Shi, Gurnee, IL (US); William H. Bunnelle, Mundelein, IL (US); Tao Li, Grayslake, IL (US); Marc J. Scanio, Lindenhurst, IL (US); Michael R. Schrimpf, Grayslake, IL (US); Chih-Hung Lee, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 241 days.

(21) Appl. No.: 12/968,113

(22) Filed: Dec. 14, 2010

(65) Prior Publication Data
US 2011/0152248 A1 Jun. 23, 2011

Related U.S. Application Data

(60) Provisional application No. 61/287,549, filed on Dec. 17, 2009, provisional application No. 61/382,284, filed on Sep. 13, 2010.

(51) Int. Cl.
 A61P 25/28 (2006.01)
 A61K 31/407 (2006.01)
 C07D 471/18 (2006.01)
 C07D 487/18 (2006.01)

(52) U.S. Cl.
 USPC ..................... 514/214.02; 540/579

(58) Field of Classification Search
 USPC ..................... 514/214.02; 540/579
 See application file for complete search history.

(56) References Cited

FOREIGN PATENT DOCUMENTS

| WO | WO2005090333 A1 | 9/2005 |
|---|---|---|
| WO | WO2007068476 A1 | 6/2007 |
| WO | WO2008067863 A2 | 6/2008 |
| WO | WO2009001129 A1 | 12/2008 |
| WO | WO2009120720 A1 | 10/2009 |
| WO | WO2010036998 A2 | 4/2010 |
| WO | WO2011003021 A1 | 1/2011 |

OTHER PUBLICATIONS

Bachurin, et al., "Antihistamine Agent Dimebon as a Novel Neuroprotector and a Cognition Enhancer," Annals of the New York Academy of Sciences, 2001, vol. 939, pp. 425-435.
Beal, M., "Mitochondria and Neurodegeneration," Novartis Found. Symp., 2007, vol. 287, pp. 183-196.
Bennett, et al., "A Peripheral Mononeuropathy in Rat that Produces Disorders of Pain Sensation like those Seen in Man," Pain, 1988, vol. 33 (1), pp. 87-107.
Berge, et al., "Pharmaceutical Salts," Journal of Pharmaceutical Sciences, 1977, vol. 66 (1), pp. 1-19.
Bitner, et al., "Broad-Spectrum Efficacy Across Cognitive Domains by α7 Nicotinic Acetylcholine Receptor Agonism Correlates with Activation of ERK1/2 and CREB Phosphorylation Pathways," The Journal of Neuroscience, 2007, vol. 27 (39), pp. 10578-10587.

Borroni, et al., "Combined Biomarkers for Early Alzheimer Disease Diagnosis," Current Medicinal Chemistry, 2007, vol. 14 (11), pp. 1171-1178.
Bouwman, et al., "Longitudinal Changes of CSF Biomarkers in Memory Clinic Patients," Neurology, 2007, vol. 69 (10), pp. 1006-1011.

(Continued)

*Primary Examiner* — Brenda Coleman
(74) *Attorney, Agent, or Firm* — Lisa V. Mueller; Michael Best & Friedrich LLP

(57) ABSTRACT

The present application relates to indole and indoline derivatives of formula (I), formula (II), formula (III), or formula (IV)

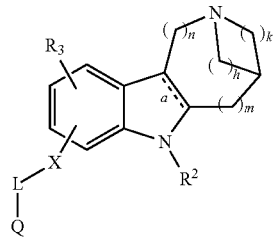

(I)

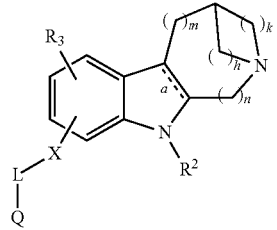

(II)

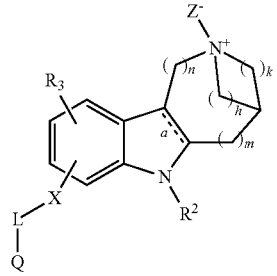

(III)

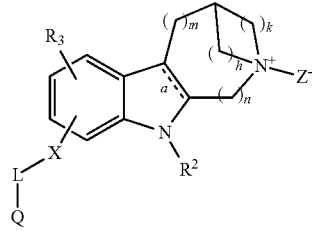

(IV)

wherein a, $R^2$, $R^3$, h, k, m, n, L, Q, X, and Z are as defined in the specification. The present application also relates to compositions comprising such compounds, and methods of treating disease conditions using such compounds and compositions.

30 Claims, 3 Drawing Sheets

(56) References Cited

OTHER PUBLICATIONS

Buccafusco, et al., "Profile of Nicotinic Acetylcholine Receptor Agonists ABT-594 and A-582941, with Differential Subtype Selectivity, on Delayed Matching Accuracy by Young Monkeys," Biochemical Pharmacology, 2007, vol. 74 (8), pp. 1202-1211.
Burns, et al., "Dimebon in Alzheimer's Disease: Old Drug for New Indication," Lancet, 2008, vol. 372 (9634), pp. 179-180.
Cavalli, et al., "Multi-Target Directed Ligands to Combat Neurodegenerative Diseases," Journal of Medicinal Chemistry, 2008, vol. 51 (3), pp. 347-372.
Chaplan, et al., "Quantitative Assessment of Tactile Allodynia in the Rat Paw," Journal of Neuroscience Methods, 1994, vol. 53, pp. 55-63.
Chauvier, et al., "Upstream Control of Apoptosis by Caspase-2 in Serum-Deprived Primary Neurons." Apoptosis, 2005, vol. 10 (6), pp. 1243-1259.
Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Csermel, et al., "The Efficiency of Multi-Target Drugs: The Network Approach Might Help Drug Design," Trends in Pharmacological Sciences, 2005, vol. 26 (4), pp. 178-182.
Cummings, et al., "18-month data from an open-label extension of a one-year controlled trial of dimebon in patients with mild-to-moderate Alzheimer's disease," Presented at the International Conference on Alzheimer's Disease (ICAD), Chicago, IL, USA, 2, 2008, Paper P4-334.
Cummings, et al., "Disease-Modifying Therapies for Alzheimer Disease: Challenges to Early Intervention," Neurology, 2007, vol. 69 (16), pp. 1622-1634.
Dixon, W., "Efficient Analysis of Experimental Observations," Annual Review of Pharmacology and Toxicology, 1980, vol. 20, pp. 441-462.
Doody, et al., "Effect of Dimebon on Cognition, Activities of Daily Living, Behaviour, and Global Function in Patients with Mild-to-Moderate Alzheimer's Disease: A Randomized, Double-Blind, Placebo-Controlled Study," Lancet, 2008, vol. 372 (9634), pp. 207-215.
Goetz, et al., "Animal Models of Alzheimer's Disease and Front Temporal Dementia," Nature Reviews Neuroscience, 2008, vol. 9 (7), pp. 532-544.
Green, et al., "Linking Calcium to A$\beta$ and Alzheimer's Disease," Neuron, 2008, vol. 59 (2), pp. 190-194.
Greene, et al., Protective Groups in Organic Synthesis, 3rd Edition, John Wiley and Sons, Inc., 1999, Table of Contents.
Grigore, et al., "Comparative Study of Action Mechanisms of Dimebon and Memantine on AMPA- and NMDA-Subtypes Glutamate Receptors in Rat Cerebral Neurons," Bulletin of Experimental Biology and Medicine, 2003, vol. 136(5), pp. 474-477.
Hu, et al., "High Content Screen Microscopy Analysis of A$\beta_{1-42}$-Induced Neurite Outgrowth Reduction in Rat Primary Cortical Neurons: Neuroprotective Effects of $\alpha$7 Neuronal Nicotinic Acetylcholine Receptor Ligands," Brain Research, 2007, vol. 1151, pp. 227-235.
Hu, et al., "Role of GSK-3$\beta$ Activation and $\alpha$7 nAChRs in A$\beta_{1-42}$-Induced Tau Phosphorylation in PC12 Cells," Journal of Neurochemistry, 2008, vol. 106 (3), pp. 1371-1377.
Hughes, D., "Progress in the Fischer Indole Reaction," A Review. Org. Prep. Proced. Int., 1993, vol. 25, pp. 607-632.
Humphrey, et al., "Practical Methodologies for the Synthesis of Indoles," Chemical Reviews, 2006, vol. 106 (7), pp. 2875-2911.
Hung, et al., "Dimebon: A phase 3 investigational agent for Alzheimer's disease with a novel mitochondrial mechanism of action," Presented at the International Conference on Alzheimer's Disease, Chicago, IL, USA, 2008, pp. S4-04-05.
International Search Report for Application No. PCT/US2010/060346, mailed on Mar. 10, 2011, 4 pages.
Juhaszova, et al., "Glycogen Synthase Kinase-3$\beta$ Mediates Convergence of Protection Signaling to Inhibit the Mitochondrial Permeability Transition Pore," The Journal of Clinical Investigation, 2004 vol. 113 (11), pp. 1535-1549.
Juhaszova, et al., "The Identity and Regulation of the Mitochondrial Permeability Transition Pore: Where the Known Meets the Unknown," Annals of the New York Academy of Sciences, 2008, vol. 1123, pp. 197-212.
Kar, et al., "Amyloid $\beta$ Peptides and Central Cholinergic Neurons: Functional Interrelationship and Relevance to Alzheimer's Disease Pathology," Progress in Brain Research, 2004, vol. 145, pp. 261-274.
Kim, et al., "An Experimental Model for Peripheral Neuropathy Produced by Segmental Spinal Nerve Ligation in the Rat," Pain, 1992, vol. 50 (3), pp. 355-363.
Lebedev, et al., "Palladium-Catalyzed Stereocontrolled Vinylation of Azoles and Phenothiazine," Organic Letters, 2002, vol. 4 (4), pp. 623-626.
Lermontova, et al., "Dimebon and Tacrine Inhibit Neurotoxic Action of $\beta$-Amyloid in Culture and Block L-Type Ca(2+) Channels," Bulletin of Experimental Biology and Medicine, 2001, vol. 132 (11), pp. 1079-1078.
Lermontova, et al., "Dimebon Improves Learning in Animals with Experimental Alzheimer's Disease," Bulletin of Experimental Biology and Medicine, 2000, vol. 129 (6), pp. 544-546.
Lin, et al., "Bax-Regulated Mitochondrial-Mediated Apoptosis is Responsible for the in Vitro Ischemia Induced Neuronal Cell Death of SPRAGUE Dawley Rat," Neuroscience Letter, 2005, vol. 387 (1), pp. 22-27.
Linseman, et al., "Glycogen Synthase Kinase-3$\beta$ Phosphorylates Bax and Promotes Its Mitochondrial Localization During Neuronal Apoptosis," The Journal of Neuroscience, 2004, vol. 24 (44), pp. 9993-10002.
Mader, et al., "Acyl Sulfonamide Anti-Proliferatives. Part 2: Activity of Heterocyclic Sulfonamide Derivatives," Bioorganic and Medicinal Chemistry Letters, 2005, vol. 15 (3), pp. 617-620.
Moreira, et al., "Is mitochondrial impairment a common link between Alzheimer's disease and diabetes A matter under discussion," Trends Alzheimer's Dis. Res., 2006, pp. 259-279.
Oddo, et al., "Temporal Profile of Amyloid-$\beta$ (A$\beta$) Oligomerization in an Invivo Model of Alzheimer Disease. A Link Between A$\beta$ and Tau Pathology," The Journal of Biological Chemistry, 2006, vol. 281 (3), pp. 1599-1604.
Phillips, et al., "Diagnostics and Biomarker Development: Priming the Pipeline," Nature Reviews, 2006 vol. 5 (6), pp. 463-469.
Piers, et al., "The Synthesis of Mercaptoindoles", 1962, vol. 40, pp. 511-517.
Poste, et al., "Lipid Vesicles as Carriers for Introducing Biologically Active Materials into Cells," Methods in Cell Biology, 1976, vol. 14, pp. 33-71.
Ray, et al., "Classification and Predictions of Clinical Alzheimer's Diagnosis based on Plasma Signaling Proteins", Nature Medicine, 2007, vol. 13(11), pp. 1359-1362.
Reddy, et al., "Amyloid $\beta$, Mitochondrial Dysfunction and Synaptic Damage: Implications for Cognitive Decline in Aging and Alzheimer's Disease," Trends in Molecular Medicine, 2008, vol. 14 (2), pp. 45-53.
Scatena, et al., "An Update on Pharmacological Approaches to Neurodegenerative Diseases," Expert Opinion on Investigational Drugs, 2007, vol. 16 (1), pp. 59-72.
Shaw, et al., "Biomarkers of Neurode Generation for Diagnosis and Monitoring Therapeutics," Nature Reviews, 2007, vol. 6 (4), pp. 295-303.
Soskic, et al., "A Connection Between the Mitochondrial Permeability Transition Pore, Autophagy, and Cerebral Amyloidogenesis," Journal of Proteome Research, 2008, vol. 7 (6), pp. 2262-2269.
Sullivan, et al., "Mitochondrial Permeability Transition in CNS Trauma: Cause or Effect of Neuronal Cell Death," Journal of Neuroscience Research, 2005, vol. 79 (1-2), pp. 231-239.

Timmermann, et al., "An Allosteric Modulator of the α7 Nicotinic Acetylcholine Receptor Possessing Cognition-Enhancing Properties in Vivo," Journal of Pharmacology and Experimental Therapeutics, 2007, vol. 323 (1), pp. 294-307.

Tkachenko, S., "Discovery and in vivo evaluation of potent 5-HT6 receptor antagonists for cognition enhancement in treating Alzheimer's disease," International Conference on Alzheimer's Disease, Chicago, IL, USA, 2008, paper P2-47.

Walsh, et al., "Deciphering the Molecular Basis of Memory Failure in Alzheimer's Disease," Neuron, 2004, vol. 44 (1), pp. 181-193.

Youdim, et al., "Multi-Functional Drugs for Various CNS Targets in the Treatment of Neurodegenerative Disorders," Trends in Pharmacological Sciences, 2005, vol. 26 (1), pp. 27-35.

Zhang, H., "One-Compound-Multiple-Targets Strategy to Combat Alzheimer's Disease," FEBS Letters, 2005, vol. 579 (24), pp. 5260-5264.

Zhang, et al., "Copper Sulfate-Pentahydrate-1,10-Phenanthroline Catalyzed Amidations of Alkynyl bromides. Synthesis of Heteroaromatic Amine Substituted Ynamides," Organic Letters, 2004, vol. 6 (7), pp. 1151-1154.

\*     p<0.05
\*\*\*   p<0.001

**  p<0.01
***  p<0.001

\*    p<0.05
\*\*   p<0.01

BRIDGEHEAD AMINE RING-FUSED INDOLES AND INDOLINES

CROSS-REFERENCE TO RELATED APPLICATION

This application claims the benefit of U.S. Provisional Patent Application No. 61/287,549, filed on Dec. 17, 2009, and U.S. Provisional Patent Application No. 61/382,284, filed on Sep. 13, 2010, each of which is herein incorporated by reference in its entirety.

STATEMENT REGARDING FEDERALLY SPONSORED RESEARCH OR DEVELOPMENT

Not applicable.

FIELD OF THE INVENTION

The present invention relates to indole and indoline derivatives, compositions comprising these indole and indoline derivatives, and methods of preventing or treating disease conditions such as neurodegeneration or neuropsychiatric disorders using such compounds and compositions.

BACKGROUND OF THE INVENTION

Treatment of dementias of various types, such as but not limited to, Alzheimer's disease (AD), Parkinson's disease, Huntington's disease and other forms, continue to be unmet medical needs. Alzheimer's disease is the most common form of dementia, wherein loss of memory and other intellectual abilities are serious enough to interfere with daily living. Alzheimer's disease is an age-related neurodegenerative disorder characterized by progressive loss of memory accompanied with cholinergic neurodegeneration (Kar, S.; Quirion, R. Amyloid β peptides and central cholinergic neurons: functional interrelationship and relevance to Alzheimer's disease pathology. *Prog. Brain Res.* 2004, 145 (Acetylcholine in the Cerebral Cortex), 261-274.). This disease accounts for over 50% of all progressive cognitive impairment in elderly patients. The prevalence increases with age. Alzheimer's disease is classified by its severity as mild, moderate and severe. The pathological hallmarks of AD include neuronal dysfunction/death, accumulation of senile plaques extracellularly and neurofibrillary tangles (NFTs) intraneuronally. Several hypotheses have been put forth to explain the pathophysiology of this disease, including aberrant β-amyloid (Aβ) metabolism, hyperphosphorylation of cytoskeletal proteins, genetic predisposition such as mutations in genes coding for presenilin-1 and -2 (PS-1 and PS-2) and amyloid precursor protein (APP), apolipoprotein E genotype, oxidative stress, excitotoxicity, inflammation and abnormal cell cycle re-entry. However to date, none of these hypotheses is sufficient to explain the diversity of biochemical and pathological abnormalities in AD.

Two pathological hallmarks of AD are generally recognized: senile plaques composed of β-amyloid peptide 1-42 ($A\beta_{1-42}$) and neurofibrillary tangles (NFTs) formed by abnormal polymerization of microtubule-associated protein tau (Walsh, D. M.; Selkoe, D. J. Deciphering the molecular basis of memory failure in Alzheimer's disease. *Neuron* 2004, 44 (1), 181-193.). While the precise cause underlying AD-related memory loss and cognitive changes remains to be fully elucidated, there is evidence indicating that pathological assemblies of $A\beta_{1-42}$ cause diverse forms of AD and that tau plays a role including in mechanisms leading to $A\beta_{1-42}$-induced neurodegeneration. More recent evidence from studies using transgenic animals suggests that tau pathology exacerbates neurodegenerative and cognitive processes in the presence of $A\beta_{1-42}$ (Oddo, S.; Caccamo, A.; et al. Temporal Profile of Amyloid-β (Aβ) Oligomerization in an in Vivo Model of Alzheimer Disease: a link between Aβ and tau pathology. *J. Biol. Chem.* 2006, 281(3), 1599-1604.). In addition to Aβ and tau, dysregulation of calcium homeostasis also plays an integral role in the pathophysiology of AD (Green, K. N.; LaFerla, F. M. Linking calcium to Aβ and Alzheimer's disease. *Neuron* 2008, 59(2), 190-194.). It is becoming evident that dysregulation of mitochondrial function and resultant altered cellular homeostasis increasingly contributes to the pathology of neurodegenerative diseases such as AD (Moreira, P. I.; Santos, M. S.; et al. Is mitochondrial impairment a common link between Alzheimer's disease and diabetes? A matter under discussion. *Trends Alzheimer's Dis. Res.* 2006, 259-279. Beal, M. F. Mitochondria and neurodegeneration. *Novartis Found. Symp.* 2007, 287 (Mitochondrial Biology), 183-196. Reddy, P. H.; Beal, M. F. Amyloid beta, mitochondrial dysfunction and synaptic damage: implications for cognitive decline in aging and Alzheimer's disease. *Trends Mol. Med.* 2008, 14(2), 45-53.).

Mitochondria play major roles in bioenergetics and cell death/survival signaling of the mammalian cell as they are 'gatekeepers of life and death'. Mitochondrial dysfunction contributes to the pathogenesis of various neurodegenerative diseases with pathophysiological consequences at multiple levels including at the level of calcium-driven excitotoxicity. One of the primary mitochondrial mechanisms is the mitochondrial permeability transition pores (MPTP) that represent a multiprotein complex derived from components of inner and outer mitochondrial membrane. The pores regulate transport of ions and peptides in and out of mitochondria, and their regulation is associated with mechanisms for maintaining cellular calcium homeostasis. A deficit in mitochondria is the earliest feature of neurodegenerative diseases. One general characteristic of aging and neurodegeneration is an increase in the number of neuronal cells undergoing signs of apoptotic degeneration. A key role for this apoptotic process is attributable to the mitochondrial permeability transition pore, which provides transport in and out of mitochondria for both calcium ions and compounds with low molecular weight. It has been proposed that MPTP is a multiprotein complex with the outer membrane fragment including porin (a voltage-dependent ion channel), anti-apoptotic proteins of the Bcl-2 family, and the peripheral benzodiazepine receptor. The inner fragment of MPTP contains an adenine nucleotide translocator and cyclophilin, which may interact with proapoptotic proteins of the Bax family Inhibition of mitochondrial calcium uptake and/or blocking of MPTP may protect cells against the development of apoptosis in the presence of pathological factors such as excitotoxins and anti-oxidants. Indirect modulation of MPTP via kinase pathways is also known wherein glycogen synthase kinase-3β (GSK3β) mediates convergence of protection signaling to inhibit the mitochondrial MPTP (Juhaszova, M.; Zorov, D. B.; et al. Glycogen synthase kinase-3β mediates convergence of protection signaling to inhibit the mitochondrial permeability transition pore. *J. Clin. Invest.* 2004, 113 (11), 1535-1549. Juhaszova, M.; Wang, S.; et al. The identity and regulation of the mitochondrial permeability transition pore: where the known meets the unknown. *Ann. N.Y. Acad. Sci.* 2008, 1123 (Control and Regulation of Transport Phenomena in the Cardiac System), 197-212.) and mitochondrial localization during apoptosis (Linseman, D. A.; Butts, B. D.; et al. Glycogen synthase kinase-3β phosphorylates Bax and promotes its mitochondrial localization during neuronal apoptosis. *J. Neurosci.* 2004, 24(44), 9993-10002.). Furthermore, calcium-dependent activation of MPTP in brain mitochondria enhances with age and may play an important role in age related neurodegenerative disorders.

Neuroprotective effects of agents have been linked to various cellular processes including inhibition of mitochondrial MPTPs. For example, the neuroprotective effects of 4-azasteroids parallel the inhibition of the mitochondrial transition pore (Soskic, V.; Klemm, M.; et al. A connection between the mitochondrial permeability transition pore, autophagy, and cerebral amyloidogenesis. *J. Proteome Res.* 2008, 7(6): 2262-2269.). In vivo administration of MPTP inhibitor, 1-(3-chlorophenyl)-3-phenyl-pyrrole-2,5-dione to a mouse model of multiple sclerosis significantly prevented the development of the disease (Pelicci, P., Giorgio, M.; et al. MPTP inhibitors for blockade of degenerative tissue damages. WO 2008067863A2). Compounds such as dimebolin (latrepirdine, 2,3,4,5-tetrahydro-2,8-dimethyl-5-[2-(6-methyl-3-pyridinyl)ethyl]-1H-pyrido[4,3-b]indole) have been shown to improve neuronal function and a role for improved neuronal outgrowth and mitochondrial function has been suggested. Dimebolin has been shown to inhibit neuronal death in models of AD and Huntington's disease, another neurodegenerative disease (Lermontova, N. N.; Lukoyanov, N. V.; et al. Dimebon improves learning in animals with experimental Alzheimer's disease. *Bull. Exp. Biol. Med.* 2000, 129 (6), 544-546. Bachurin, S.; Bukatina, E.; et al. Antihistamine agent dimebon as a novel neuroprotector and a cognition enhancer. *Ann. N.Y. Acad. Sci.* 2001, 939 (Neuroprotective Agents), 425-435.). More recently, dimebolin has been shown to possess a clinically beneficial effect in cognition in patients with AD (Burns, A.; Jacoby, R. Dimebon in Alzheimer's disease: old drug for new indication. *Lancet* 2008, 372 (9634), 179-80. Doody, R. S.; Gavrilova, S. I.; et al. Effect of dimebon on cognition, activities of daily living, behaviour, and global function in patients with mild-to-moderate Alzheimer's disease: a randomised, double-blind, placebo-controlled study. *Lancet* 2008, 372 (9634), 207-215.). Patients with mild-to-moderate Alzheimer's disease administered with 20 mg three times a day (60 mg/day) showed significant improvement in the clinical course of disease, as reflected in improvement over baseline for ADAS-Cog (Alzheimer's disease assessment scale—cognitive subscale). In particular, dimebolin-treated patients demonstrated a significant improvement over placebo in cognition, global function, activities of daily living and behavior. A six-month open-label extension trial of dimebolin produced results similar to those in the preceding 12-month clinical trial (Cummings, J.; Doody, R.; Gavrilova, S.; Sano, M.; Aisen, P.; Seely, L.; Hung, D. 18-month data from an open-label extension of a one-year controlled trial of dimebon in patients with mild-to-moderate Alzheimer's disease. Presented at the International Conference on Alzheimer's Disease (ICAD), Chicago, Ill., USA, July 2008; paper P4-334.). Patients with mild-to-moderate AD who had earlier received the drug for 12 months had preservation of function close to their starting baseline on key symptoms of AD. Patients originally on placebo who received dimebolin in the extension study showed stabilization across all key measures.

Dimebolin has been approved in Russia as a non-selective antihistamine. The drug was sold for many years before selective anti-histaminergic agents were developed. Although dimebolin was initially thought to exert its cognitive enhancing effects through inhibition of butyryl-cholinesterase, acetyl cholinesterase, NMDA receptor or L-type calcium channels (Bachurin, S.; Bukatina, E.; et al. Antihistamine agent dimebon as a novel neuroprotector and a cognition enhancer. *Ann. N.Y. Acad. Sci.* 2001, 939 (Neuroprotective Agents), 425-435. Lermontova, N. N.; Redkozubov, A. E.; et al. Dimebon and tacrine inhibit neurotoxic action of beta-amyloid in culture and block L-type Ca(2+) channels. *Bull. Exp. Biol. Med.* 2001, 132(5), 1079-83. Grigor'ev, V. V.; Dranyi, O. A.; et al. Comparative Study of Action Mechanisms of Dimebon and Memantine on AMPA- and NMDA-Subtypes Glutamate Receptors in Rat Cerebral Neurons. *Bull. Exp. Biol. Med.* 2003, 136(5): 474-477.), its interactions at these targets are weak. More recent data suggest that dimebolin may exert its effects at the level of mitochondria, and that these activities could enhance neuronal function (Hung, D. Dimebon: A phase 3 investigational agent for Alzheimer's disease with a novel mitochondrial mechanism of action. Presented at the International Conference on Alzheimer's Disease, Chicago, Ill., USA, July 2008; paper S4-04-05.). Hung and coworkers (Hung, D. Dimebon: A phase 3 investigational agent for Alzheimer's disease with a novel mitochondrial mechanism of action. Presented at the International Conference on Alzheimer's Disease, Chicago, Ill., USA, July 2008; paper S4-04-05.) reported that dimebolin can protect cells from excitotoxic damage and improve neurite outgrowth in neuroblastoma cell lines and primary neurons. From an adverse effect standpoint, in recently reported clinical studies of dimebolin, the most frequent adverse event was dry mouth, which is consistent with the antihistaminic effects of dimebolin (Doody, R. S.; Gavrilova, S. I.; et al. Effect of dimebon on cognition, activities of daily living, behaviour, and global function in patients with mild-to-moderate Alzheimer's disease: a randomised, double-blind, placebo-controlled study. *Lancet* 2008, 372 (9634), 207-215.). There is a need in the art to identify and provide novel agents for treating or preventing conditions associated with neurodegenerative disorders such as AD, lacking histaminergic (H1) interactions.

As noted earlier, given the likely multiple etiologies of neurodegenerative diseases such as AD, multiple avenues are being pursued as symptomatic approaches or as disease modifying approaches to alter the underlying pathology of the disease (Scatena, R.; Martorana, G. E.; et al. An update on pharmacological approaches to neurodegenerative diseases. *Expert Opin. Invest. Drugs* 2007, 16(1), 59-72.). In particular, the reported benefit of dimebolin in double-blind, placebo-controlled study of patients with mild-to-moderate AD across many cognitive and clinical measures demonstrates the potential of such compounds to prevent or treat a variety of neurodegenerative diseases where an underlying pathology involves deficits in cognitive function. In addition to the need for improved receptor selectivity profile (as for example vs. H1 receptors), one of the current limitations with dimebolin is the dosing regimen necessitating three times per day (t.i.d.) administration in humans. As neuroprotective approaches exemplified by dimebolin continue to be validated as a viable clinical approach, there is a need in the art to identify and provide novel compounds for treating or preventing cognitive deficits associated with AD and other neurodegenerative and neuropsychiatric diseases.

SUMMARY OF THE INVENTION

In one aspect, the present invention relates to compounds of having a formula of (I), formula (II), formula (III), or formula (IV):

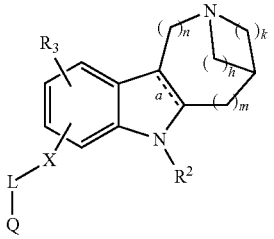

(I)

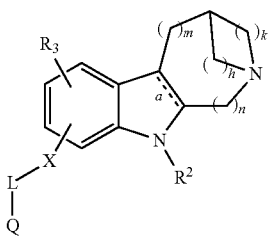

(II)

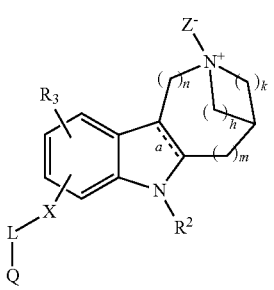

(III)

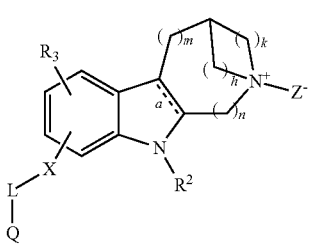

(IV)

or a pharmaceutically acceptable salt thereof, wherein
a is a single or double bond;
k is 1, 2, or 3;
h is 1, 2, or 3;
m is 0, 1, or 2;
n is 1 or 2, wherein the sum of k, m, and n is 3, 4, or 5;
X is O, S, S(O), S(O)$_2$, or a bond;
L is —[C(R$^a$)(R$^b$)]$_p$—, —[C(R$^a$)(R$^b$)]$_{q1}$—[(CR$^c$)=CR$^d$)]—[C(R$^a$)(R$^b$)]$_{q2}$—, —[C(R$^a$)(R$^b$)]$_{r1}$—[C≡C]—[C(R$^a$)(R$^b$)]$_{r2}$—, —[C(R$^a$)(R$^b$)]$_s$-cyclopropylene-[C(R$^a$)(R$^b$)]$_t$—, or a bond; or
X and L taken together are a bond;
Q is substituted or unsubstituted monocyclic aryl, substituted or unsubstituted bicyclic aryl, substituted or unsubstituted monocyclic heteroaryl, or substituted or unsubstituted bicyclic heteroaryl;
R$^2$ is hydrogen, C$_1$-C$_4$ alkyl, C$_2$-C$_4$ alkenyl, or C$_2$-C$_4$ alkynyl, wherein C$_1$-C$_4$ alkyl, and the saturated carbon atoms of C$_2$-C$_4$ alkenyl and C$_2$-C$_4$ alkynyl, can be unsubstituted or substituted by hydroxyl, C$_1$-C$_8$ alkyl, C$_1$-C$_8$ haloalkyl, carboxy, or alkoxycarbonyl;
R$^3$ is hydrogen, halogen, C$_1$-C$_5$ haloalkyl, C$_1$-C$_5$ alkoxy, C$_1$-C$_5$ haloalkoxy, or cyano;
R$^a$, R$^b$, R$^c$, and R$^d$ are, at each occurrence, independently hydrogen, halogen, C$_1$-C$_8$ alkyl, C$_1$-C$_8$ haloalkyl, carboxy, or alkoxycarbonyl;

p is 1, 2, 3, 4, or 5;
q1 and q2 are independently 0, 1, 2, or 3, provided that the sum of q1 and q2 is 0, 1, 2, or 3;
r1 and r2 are independently 0, 1, 2, or 3, provided that the sum of r1 and r2 is 0, 1, 2, or 3;
s is 0, 1 or 2;
t is 0 or 1; and
Z is O or BH$_3$;
wherein Q, when substituted, is independently substituted with 1, 2, 3, 4, or 5 substituents, wherein the substituent is halogen, cyano, C$_1$-C$_5$ haloalkyl, C$_1$-C$_5$ alkyl, C$_2$-C$_5$ alkenyl, C$_2$-C$_5$ alkynyl, hydroxy, C$_1$-C$_5$ alkoxy, —O—C$_1$-C$_5$ haloalkyl, —S—C$_1$-C$_5$ alkyl, —S—C$_1$-C$_5$ haloalkyl, —SO$_2$—C$_1$-C$_5$ alkyl, —SO$_2$—C$_1$-C$_5$ haloalkyl, C$_1$-C$_5$ cyanoalkyl, or —NO$_2$.

In another aspect, the present invention relates to pharmaceutical compositions comprising a therapeutically effective amount of at least one compound(s) having a formula of (I), (II), (III), or (IV) described above or pharmaceutically acceptable salts thereof, in combination with at least one pharmaceutically acceptable carrier.

In yet another aspect, the present invention relates to a method of preventing or treating a neurodegeneration disorder using a compound of formula (I), formula (II), formula (III), or formula (IV). Such methods involves administering a therapeutically effective amount of at least one compound of formula (I), formula (II), formula (III), or formula (IV) to a subject in need of treatment thereof. Examples of neurodegeneration disorders are Alzheimer's disease (AD), mild cognitive impairment (MCI), age-associated memory impairment (AAMI), multiple sclerosis, Parkinson's disease, vascular dementia, senile dementia, AIDS dementia, Pick's disease, dementia caused by cerebrovascular disorders, corticobasal degeneration, amyotrophic lateral sclerosis (ALS), Huntington's disease, diminished CNS function associated with traumatic brain injury or any combinations thereof. The above method also further comprises administering a cognitive enhancing drug to the subject. The cognitive enhancing drug can be administered simultaneously or sequentially with the compound of formula (I), formula (II), formula (III), or formula (IV).

In yet another aspect, the present invention relates to a method of preventing or treating a neuropsychiatric disorder using a compound of formula (I), formula (II), formula (III), or formula (IV). Such methods involve administering a therapeutically effective amount of at least one compound of formula (I), formula (II), formula (III), or formula (IV) to a subject in need of treatment thereof. Examples of neuropsychiatric disorders are schizophrenia, cognitive deficits in schizophrenia, attention deficit disorder, attention deficit hyperactivity disorder, bipolar and manic disorders, depression or any combinations thereof. The above method also further comprises administering a cognitive enhancing drug to the subject. The cognitive enhancing drug can be administered simultaneously or sequentially with the compound of formula (I), formula (II), formula (III), or formula (IV).

In a further aspect, the present invention relates to methods of preventing or treating a pain condition using a compound of formula (I), formula (II), formula (III), or formula (IV). Such methods include administering a therapeutically effective amount of at least one compound of formula (I), formula (II), formula (III), or formula (IV) to a subject in need of treatment thereof. Examples of pain conditions includes neuropathic and nociceptive pain, chronic or acute, such as, without limitation, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, ocular pain, visceral pain, cancer pain, dental pain, headache, migraine, carpal tunnel syndrome, fibromyalgia, neuritis, sciatica, pelvic hypersensitivity, pelvic pain, post operative pain, post stroke pain, and menstrual pain.

The present invention can also include use of a compound of formula (I), formula (II), formula (III), or formula (IV) as neuroprotective agent for the prevention or treatment of a neurological disorder or condition. The method includes administering a therapeutically effective amount of at least one compound of formula (I), formula (II), formula (III), or formula (IV) to a subject in need of treatment thereof. The neurological disorder or condition can include, but is not limited to, neurodegeneration disorders, neuropsychiatric disorder and pain conditions, brain injuries, stroke and other acute and chronic neuronal injuries or degenerative conditions. The neurological disorder or condition can include, for example, conditions associated, at least in part, with mitochondrial dysfunction and/or neuronal apoptosis in the central nervous system.

In still yet another aspect, the present invention relates to the use of a compound of formula (I), formula (II), formula (III), or formula (IV) or a pharmaceutically acceptable salt thereof in the manufacture of a medicament for the prevention or treatment of the neurodegeneration disorders described above, alone or in combination with at least one pharmaceutically acceptable carrier.

The compounds of formula (I), formula (II), formula (III), or formula (IV), compositions comprising these compounds, and methods for preventing or treating neurodegenerative or neuropsychiatric disorders by administering these compounds or pharmaceutical compositions are further described herein.

These and other objects of the invention are described in the following paragraphs. These objects should not be deemed to narrow the scope of the invention.

DETAILED DESCRIPTION

Figure 1:
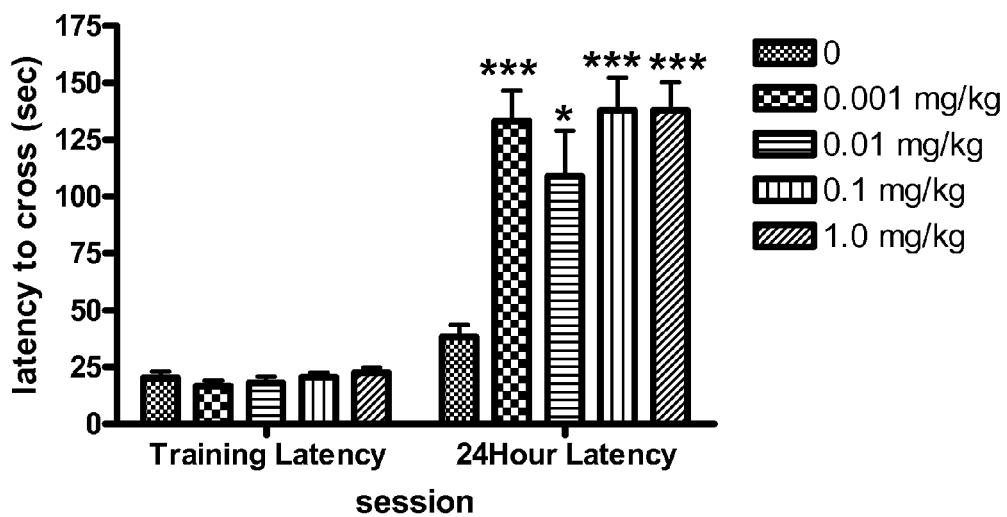
FIG. 1 shows a graphical representation of the concentration-dependent improvement in mouse 24-hour recall inhibitory avoidance scores upon treatment with test compound (Example 1). The X-axis represents the day of exposure to condition, and the Y-axis represents the latency to cross to the punished side.

In one aspect, the present invention relates to compounds having a formula (I), formula (II), formula (III), or formula (IV) as shown below:

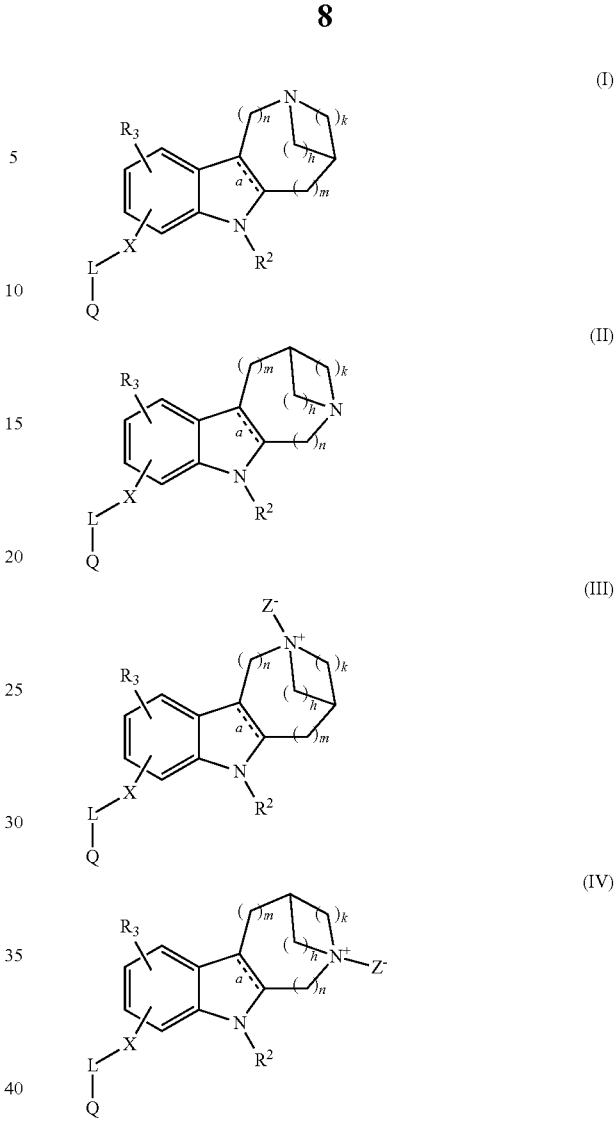

wherein a, $R^2$, $R^3$, h, k, m, n, L, Q, X, and Z are as defined herein.

In another aspect, the present invention relates to composition comprising compounds having a formula (I), formula (II), formula (III), or formula (IV) as described above and at least one pharmaceutically acceptable carrier.

In still yet another aspect, the present invention relates to methods for preventing and treating disease conditions, such as neurodegeneration disorders or neuropsychiatric disorders, using compounds having a formula of formula (I), formula (II), formula (III), or formula (IV) as described above.

In still yet another aspect, the present invention relates to the use of compounds having a formula (I), formula (II), formula (III), or formula (IV) in the manufacture of a medicament for the prevention or treatment of the disease conditions, such as neurodegeneration disorders or neuropsychiatric disorders, described above, alone or in combination with at least one pharmaceutically acceptable carrier.

In various embodiments, the present invention provides at least one variable that occurs more than one time in any substituent or in the compound of the present invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definitions

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2 to 6 carbon atoms and contains at least one carbon-carbon double. The term "$C_2$-$C_5$ alkenylene" means a straight or branched chain divalent hydrocarbon containing 2 to 5 carbon atoms and at least one carbon-carbon double. Representative examples of alkylene include, but are not limited to, —CH=CH— and —CH$_2$CH=CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkyl" as used herein, means a straight or branched, saturated hydrocarbon chain containing from 1 to 10 carbon atoms. The term "lower alkyl" or "$C_1$-$C_6$ alkyl" means a straight or branched chain hydrocarbon containing 1 to 6 carbon atoms. The term "$C_1$-$C_3$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon 1 to 10 carbon atoms. The term "$C_1$-$C_5$ alkylene" means a straight or branched chain divalent hydrocarbon containing 1 to 5 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkynylene" means a divalent group derived from a straight or branched chain hydrocarbon of from 2 to 10 carbon atoms containing at least one triple bond. The term "$C_2$-$C_5$ alkynylene" means a straight or branched chain divalent hydrocarbon containing 2 to 5 carbon atoms and at least one carbon-carbon triple. Representative examples of alkynylene include, but are not limited to, —C≡C—, —CH$_2$C≡C—, —CH(CH$_3$)CH$_2$C≡C—, —C≡CCH$_2$—, and —C≡CCH(CH$_3$)CH$_2$—.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "carbonyl" as used herein, means a —C(O)— group.

The term "carboxy" as used herein, means a —CO$_2$H group.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein, means a monocyclic or bicyclic ring system containing from 3 to 10 carbons and containing at least one carbon-carbon double bond formed by the removal of two hydrogens. Representative examples of monocyclic ring systems include, but are not limited to, 2-cyclohexen-1-yl, 3-cyclohexen-1-yl, 2,4-cyclohexadien-1-yl and 3-cyclopenten-1-yl. Bicyclic ring systems are exemplified by a monocyclic cycloalkenyl ring system which is fused to another monocyclic cycloalkyl ring as defined herein, a monocyclic aryl ring as defined herein, a monocyclic heterocycle as defined herein or a monocyclic heteroaryl as defined herein. The bicyclic ring systems of the present invention must be appended to the parent molecular moiety through an available carbon atom within the cycloalkenyl ring. Representative examples of bicyclic ring systems include, but are not limited to, 4,5-dihydro-benzo[1,2,5]oxadiazole, 3a, 4, 5, 6, 7,7a-hexahydro-1H-indenyl, 1, 2, 3, 4,5, 6-hexahydro-pentalenyl, 1, 2, 3, 4, 4a, 5, 6,8a-octahydro-pentalenyl.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkylene" as used herein, denotes a divalent group derived from a monocyclic cycloalkyl containing 3 to 8 carbon atoms. The two attachment points are not on the same carbon atom. Representative examples of cycloalkylene include, but are not limited to, cyclopropylene, cyclobutylene, cyclopentylene, cyclohexylene, cycloheptalene, and cyclooctalene.

The term "halo" or "halogen" as used herein, means Cl, Br, I, or F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroarylalkyl," as used herein, means a heteroaryl group appended to the parent molecular moiety through an alkyl group, as defined herein.

The term "heteroatom" as used herein, means a nitrogen, oxygen, or sulfur atom.

The term "hydroxyl" or "hydroxy" as used herein, means an —OH group.

The term "oxo" as used herein, means a =O group.

The term "pain", as used herein, is understood to mean nociceptive pain and neuropathic pain, both chronic and acute pain, including but not limited to, osteoarthritis or rheumatoid arthritis pain, ocular pain, pains associated with intestinal inflammation, pains associated with cardiac muscle inflammation, pains associated with multiple sclerosis, pains associated with neuritis, pains associated with carcinomas and sarcomas, pains associated with AIDS, pains associated with chemotherapy, amputation pain, trigeminus neuralgia, headaches, such as migraine cephalalgia, or neuropathic pains, such as post-herpes zoster neuralgia, post-injury pains and post-operative pains.

The term "sulfonyl", as used herein, means a —$SO_2$— group.

b. Compounds

Compounds of the present invention have the formula (I), formula (II), formula (III), or formula (IV) as described above.

Particular values of variable groups in compounds of formula (I), formula (II), formula (III), or formula (IV) are as follows. Such values may be used where appropriate with any of the other values, definitions, claims or embodiments defined hereinbefore or hereinafter.

In one embodiment, a is a single or double bond.

In another embodiment, a is a single bond.

In a further embodiment, a is a double bond.

In one embodiment, X is O, S, S(O), $S(O)_2$, or a bond;

In another embodiment, X is O or a bond.

In a further embodiment, X is a bond.

In one embodiment, Z is O or $BH_3$.

In another embodiment, Z is O.

In another embodiment, Z is $BH_3$.

In one embodiment, L is —$[C(R^a)(R^b)]_p$—, —$[C(R^a)(R^b)]_{q1}$—$[(CR^c)=(CR^d)]$—$[C(R^a)(R^b)]_{q2}$—, —$[C(R^a)(R^b)]_{r1}$—[C≡C]—$[C(R^a)(R^b)]_{r2}$—, —$[C(R^a)(R^b)]_s$-cyclopropylene-$[C(R^a)(R^b)]_t$—, or a bond.

In another embodiment, L is —$[C(R^a)(R^b)]_p$—, and p is 1, 2, 3, 4, or 5.

In a further embodiment, L is —$[C(R^a)(R^b)]_p$—, and p is 1, 2, or 3.

In another embodiment, L is —$[C(R^a)(R^b)]_{q1}$—$[(CR^c)=(CR^d)]$—$[C(R^a)(R^b)]_{q2}$—, and q1 and q2 are independently 0, 1, 2, or 3, provided that the sum of q1 and q2 is 0, 1, 2, or 3.

In another embodiment, L is —$[C(R^a)(R^b)]_{q1}$—$[(CR^c)=(CR^d)]$—$[C(R^a)(R^b)]_{q2}$—, q1 is 0, and q2 is 1, 2, or 3.

In a further embodiment, L is —$[C(R^a)(R^b)]_{q1}$—$[(CR^c)=(CR^d)]$—$[C(R^a)(R^b)]_{q2}$—, and q1 and q2 are each 0.

In another embodiment, L is —$[C(R^a)(R^b)]_{r1}$—[C≡C]—$[C(R^a)(R^b)]_{r2}$—, and r1 and r2 are independently 0, 1, 2, or 3, provided that the sum of r1 and r2 is 0, 1, 2, or 3.

In a further embodiment, L is —$[C(R^a)(R^b)]_{r1}$—[C≡C]—$[C(R^a)(R^b)]_{r2}$—, and r1 and r2 are each 0.

In another embodiment, L is —$[C(R^a)(R^b)]_s$-cyclopropylene-$[C(R^a)(R^b)]_t$—, and s is 0, 1. or 2, and t is 0 or 1.

In a further embodiment, L is —$[C(R^a)(R^b)]_s$-cyclopropylene-$[C(R^a)(R^b)]_t$—, and s and t are each 0.

In another embodiment, L is a bond.

In one embodiment, $R^a$, $R^b$, $R^c$, and $R^d$, are, at each occurrence, independently hydrogen, halogen, $C_1$-$C_8$ alkyl, $C_1$-$C_8$ haloalkyl, carboxy, or alkoxycarbonyl.

In another embodiment, $R^a$, $R^b$, $R^c$, and $R^d$, are, at each occurrence, independently hydrogen, halogen, $C_1$-$C_8$ alkyl, or $C_1$-$C_8$ haloalkyl.

In a further embodiment, $R^a$, $R^b$, $R^c$, and $R^d$, are, at each occurrence, hydrogen.

In one embodiment, X and L together are —$[C(R^a)(R^b)]_p$—, —O—$[C(R^a)(R^b)]_p$—, —$[C(R^a)(R^b)]_{q1}$—$[(CR^c)=(CR^d)]$—$[C(R^a)(R^b)]_{q2}$—, —$[C(R^a)(R^b)]_{r1}$—[C≡C]—$[C(R^a)(R^b)]_{r2}$—, —$[C(R^a)(R^b)]_s$-cyclopropylene-$[C(R^a)(R^b)]_t$—, or a bond.

In another embodiment, X and L together are a bond, —CH=CH—, —CH=CHCH$_2$CH$_2$CH$_2$—, —C≡C—, —CH$_2$—CH$_2$—, —CH$_2$CH$_2$CH$_2$CH$_2$CH$_2$—, or —OCH$_2$—.

In one embodiment, $R^2$ is hydrogen, $C_1$-$C_4$ alkyl, $C_2$-$C_4$ alkenyl, or $C_2$-$C_4$ alkynyl, wherein $C_1$-$C_4$ alkyl, and the saturated carbon atoms of $C_2$-$C_4$ alkenyl and $C_2$-$C_4$ alkynyl, can be unsubstituted or substituted by halogen, hydroxyl, $C_1$-$C_8$ alkyl, $C_1$-$C_8$ haloalkyl, carboxy, or alkoxycarbonyl.

In another embodiment, $R^2$ is $C_1$-$C_4$ alkyl, $C_2$-$C_4$ alkenyl, or $C_2$-$C_4$ alkynyl, wherein $C_1$-$C_4$ alkyl, and the saturated carbon atoms of $C_2$-$C_4$ alkenyl and $C_2$-$C_4$ alkynyl, can be unsubstituted or substituted by halogen, hydroxyl, $C_1$-$C_8$ alkyl, $C_1$-$C_8$ haloalkyl, carboxy, or alkoxycarbonyl.

In a further embodiment, $R^2$ is hydrogen.

In one embodiment, $R^3$ is hydrogen, halogen, $C_1$-$C_5$ haloalkyl, $C_1$-$C_5$ alkoxy, $C_1$-$C_5$ haloalkoxy, or cyano.

In another embodiment, $R^3$ is $C_1$-$C_5$ haloalkyl, $C_1$-$C_5$ alkoxy, $C_1$-$C_5$ haloalkoxy, or cyano.

In a further embodiment, $R^3$ is hydrogen or halogen.

In one embodiment, Q is substituted or unsubstituted monocyclic aryl, substituted or unsubstituted bicyclic aryl, substituted or unsubstituted monocyclic heteroaryl, or substituted or unsubstituted bicyclic heteroaryl, wherein Q, when substituted, is independently substituted with 1, 2, 3, 4, or 5 substituents, wherein the substituent is halogen, cyano, $C_1$-$C_5$ haloalkyl, $C_1$-$C_5$ alkyl, $C_2$-$C_5$ alkenyl, $C_2$-$C_5$ alkynyl, hydroxy, $C_1$-$C_5$ alkoxy, —O—$C_1$-$C_5$ haloalkyl, —S—$C_1$-$C_5$ alkyl, —S—$C_1$-$C_5$ haloalkyl, —$SO_2$—$C_1$-$C_5$ alkyl, —$SO_2$—$C_1$-$C_5$ haloalkyl, $C_1$-$C_5$ cyanoalkyl, or —$NO_2$.

In another embodiment, Q is substituted or unsubstituted monocyclic aryl or substituted or unsubstituted bicyclic aryl, wherein Q, when substituted, is independently substituted with 1, 2, or 3 substituents, wherein the substituent is halogen, $C_1$-$C_5$ alkoxy, —O—$C_1$-$C_5$ haloalkyl, $C_1$-$C_5$ haloalkyl, or $C_1$-$C_5$ alkyl.

In a further embodiment, Q is substituted or unsubstituted phenyl, wherein phenyl, when substituted, is independently substituted with 1 or 2 substituents, wherein the substituent is $C_1$-$C_5$ alkyl, $C_1$-$C_5$ alkoxy, —O—$C_1$-$C_5$ haloalkyl or halogen.

In another embodiment, Q is substituted or unsubstituted monocyclic heteroaryl, or substituted or unsubstituted bicyclic heteroaryl, wherein Q, when substituted, is independently substituted with 1, 2, or 3 substituents, wherein the substituent is halogen, $C_1$-$C_5$ haloalkyl, —O—$C_1$-$C_5$ haloalkyl, $C_1$-$C_5$ alkoxy, or $C_1$-$C_5$ alkyl.

In a another embodiment, Q is substituted or unsubstituted pyridyl, pyrimidinyl, quinolinyl or thienyl, wherein pyridyl, pyrimidinyl, quinolinyl or thienyl, when substituted, are independently substituted with 1 or 2 substituents, wherein the substituent is $C_1$-$C_5$ alkyl, $C_1$-$C_5$ alkoxy, —O—$C_1$-$C_5$ haloalkyl or halogen.

In a further embodiment, Q is substituted or unsubstituted pyridyl, wherein pyridyl, when substituted, is independently substituted with 1 or 2 substituents, wherein the substituent is alkyl, $C_1$-$C_5$ alkoxy, —O—$C_1$-$C_5$ haloalkyl or halogen.

In one embodiment, k is 1, 2, or 3; h is 1, 2 or 3; m is 0, 1, or 2; n is 1 or 2; wherein the sum of k, m, and n is 3, 4, or 5.

In one embodiment, compounds of formula (I), formula (II), formula (III), or formula (IV) can include, but are not limited to compounds wherein a is a double bond; k is 2, m is 0, and n is 1.

In another embodiment, compounds of formula (I), formula (II), formula (III), or formula (IV) can include, but are not limited to compounds wherein a is a single bond; k is 2, m is 0, and n is 1.

In another embodiment, compounds of formula (I), formula (II), formula (III), or formula (IV) can include, but are not limited to compounds wherein a is a double bond; k is 3, m is 0, and n is 1.

In another embodiment, compounds of formula (I), formula (II), formula (III), or formula (IV) can include, but are not limited to compounds wherein a is a single bond; k is 3, m is 0, and n is 1.

In another embodiment, compounds of formula (I) can include, but are not limited to compounds of formula (I-a).

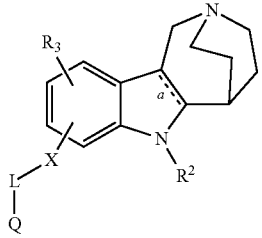
(I-a)

In a further embodiment, compounds of formula (I-a) can include, but are not limited to compounds of formula (I-a-1), (I-a-2), (I-a-3), (I-a-4), (I-a-5), (I-a-6), (I-a-7), (I-a-8), (I-a-9), or (I-a-10).

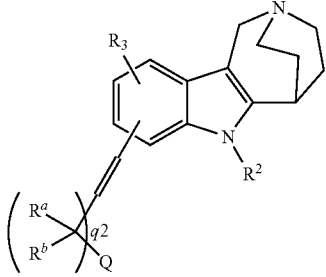
(I-a-1)

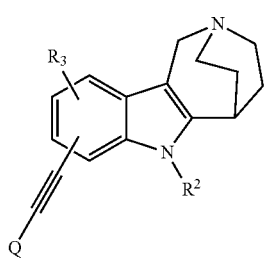
(I-a-2)

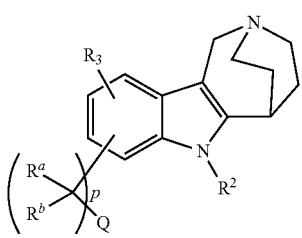
(I-a-3)

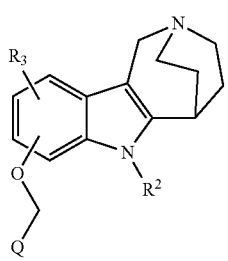
(I-a-4)

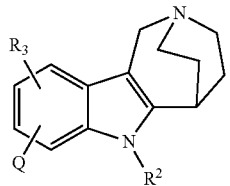
(I-a-5)

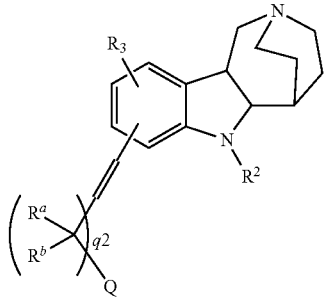
(I-a-6)

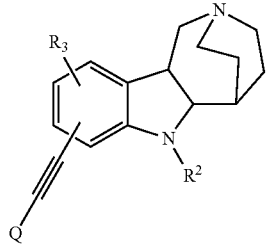
(I-a-7)

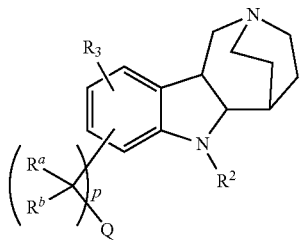
(I-a-8)

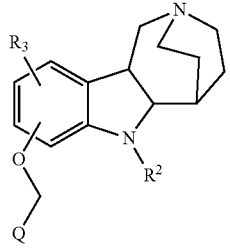
(I-a-9)

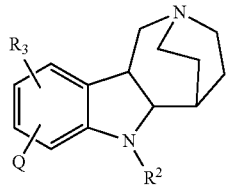
(I-a-10)

In another embodiment, compounds of formula (I) can include, but are not limited to compounds of formula (I-b).

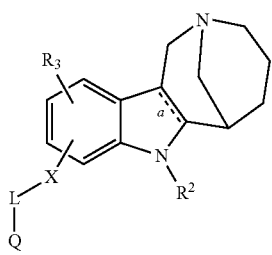
(I-b)
In a further embodiment, compounds of formula (I-b) can include, but are not limited to compounds of formula (I-b-1), (I-b-2), (I-b-3), (I-b-4), (I-b-5), (I-b-6), (I-b-7), (I-b-8), (I-b-9), or (I-b-10).
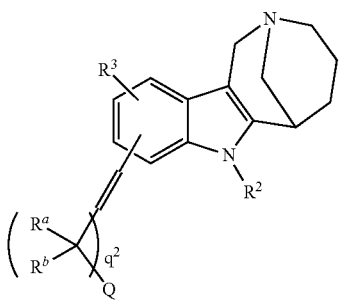
(I-b-1)
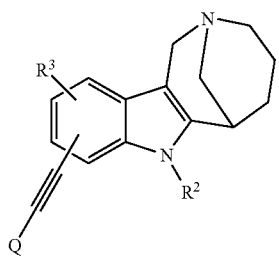
(I-b-2)
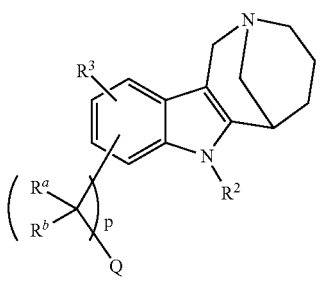
(I-b-3)
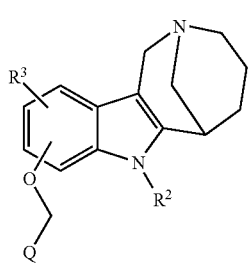
(I-b-4)
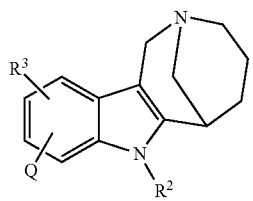
(I-b-5)
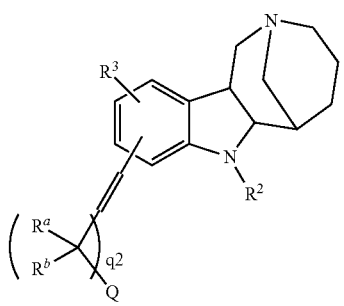
(I-b-6)
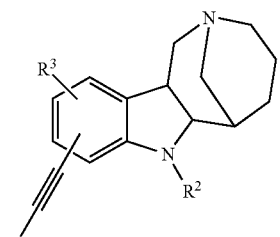
(I-b-7)
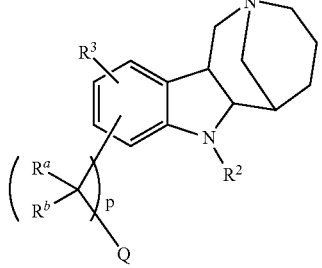
(I-b-8)
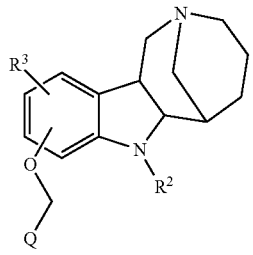
(I-b-9)
(I-b-10)
In another embodiment, compounds of formula (II) can include, but are not limited to compounds of formula (II-a).

(II-a)
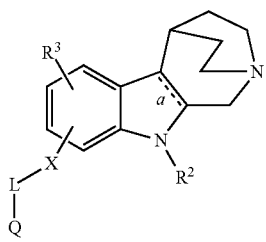
In a further embodiment, compounds of formula (II-a) can include, but are not limited to compounds of formula (II-a-1), (II-a-2), (II-a-3), (II-a-4), (II-a-5), (II-a-6), (II-a-7), (II-a-8), (II-a-9), or (II-a-10).
(II-a-1)
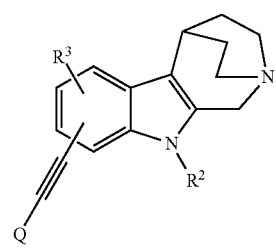
(II-a-2)
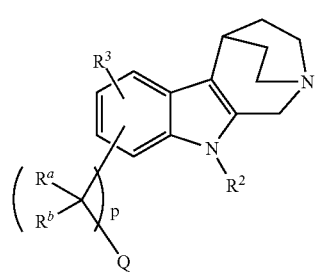
(II-a-3)
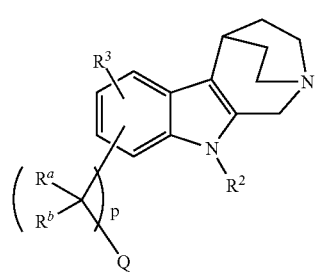
(II-a-4)
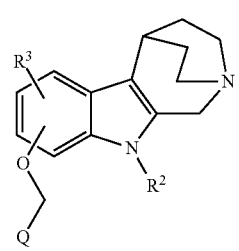
(II-a-5)
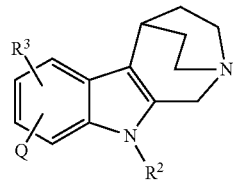
(II-a-6)
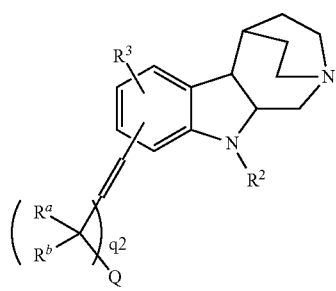
(II-a-7)
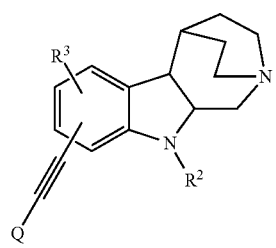
(II-a-8)
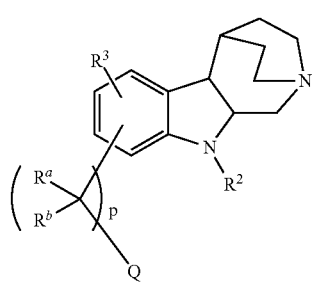
(II-a-9)
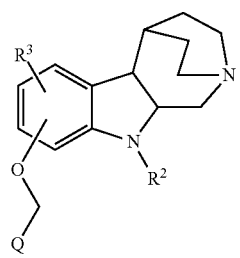
(II-a-10)
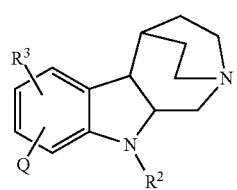
In another embodiment, compounds of formula (II) can include, but are not limited to compounds of formula (II-b).

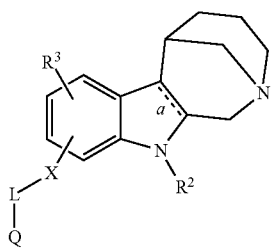
(II-b)
In a further embodiment, compounds of formula (II-b) can include, but are not limited to compounds of formula (II-b-1), (II-b-2), (II-b-3), (II-b-4), (II-b-5), (II-b-6), (II-b-7), (II-b-8), (II-b-9), or (II-b-10).
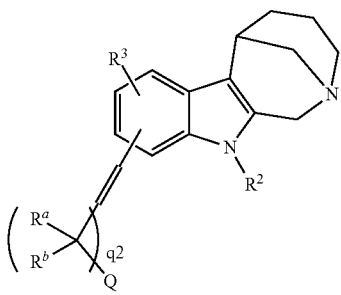
(II-b-1)
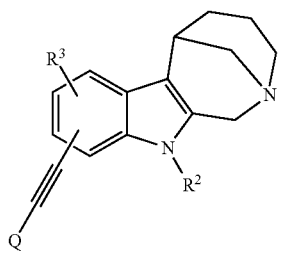
(II-b-2)
(II-b-3)
(II-b-4)
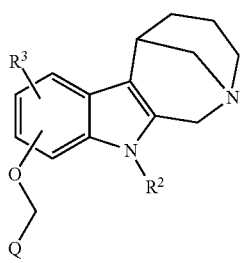
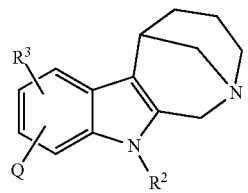
(II-b-5)
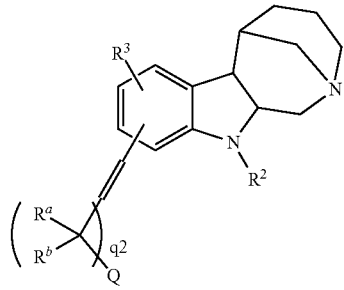
(II-b-6)
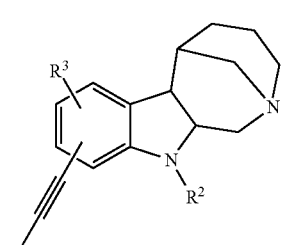
(II-b-7)
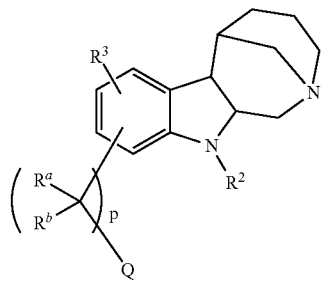
(II-b-8)
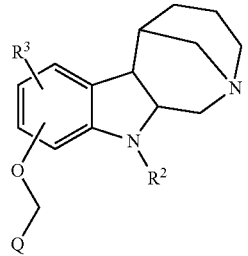
(II-b-9)
(II-b-10)

In another embodiment, compounds of formula (III) can include, but are not limited to compounds of formula (III-a).
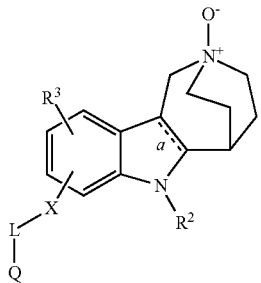
(III-a)
In a further embodiment, compounds of formula (III-a) can include, but are not limited to compounds of formula (III-a-1), (III-a-2), (III-a-3), (III-a-4), (III-a-5), (III-a-6), (III-a-7), (III-a-8), (III-a-9), or (III-a-10).
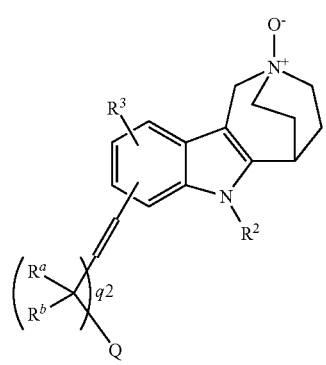
(III-a-1)
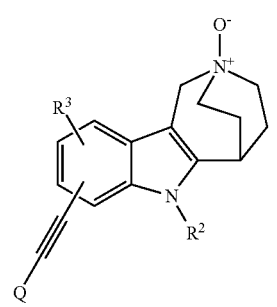
(III-a-2)
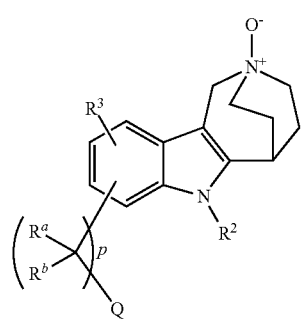
(III-a-3)
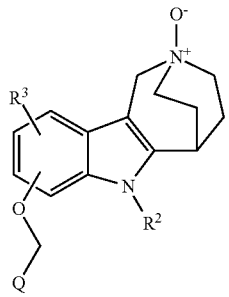
(III-a-4)
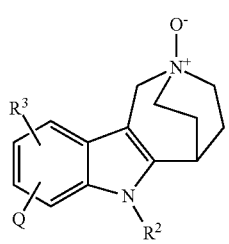
(III-a-5)
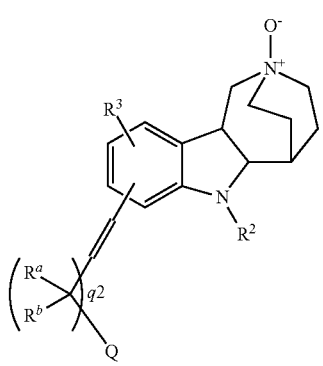
(III-a-6)
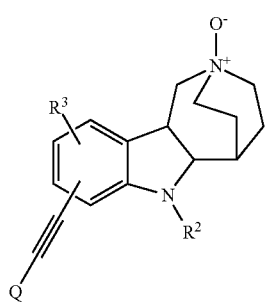
(III-a-7)
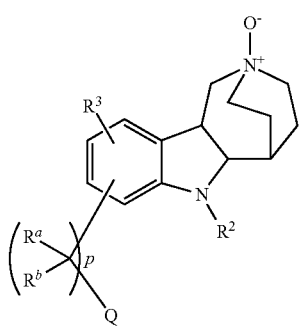
(III-a-8)

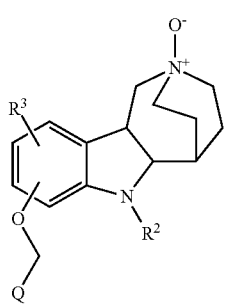
(III-a-9)
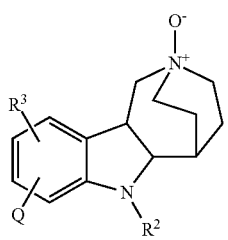
(III-a-10)
In another embodiment, compounds of formula (III) can include, but are not limited to compounds of formula (III-b).
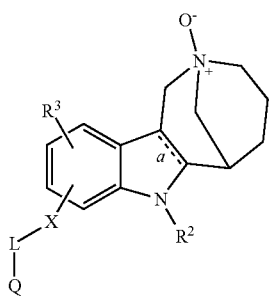
(III-b)
In a further embodiment, compounds of formula (III-b) can include, but are not limited to compounds of formula (III-b-1), (III-b-2), (III-b-3), (III-b-4), (III-b-5), (III-b-6), (III-b-7), (III-b-8), (III-b-9), or (III-b-10).
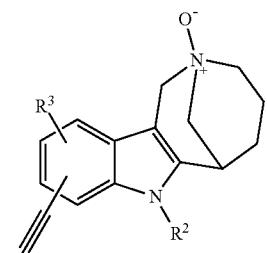
(III-b-1)
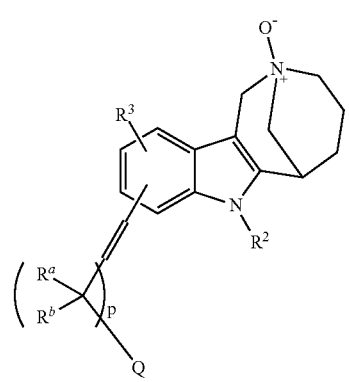
(III-b-2)
(III-b-3)
(III-b-4)
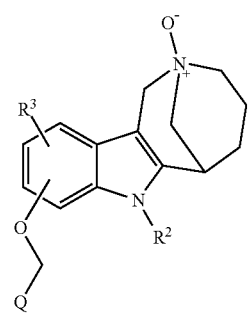
(III-b-5)
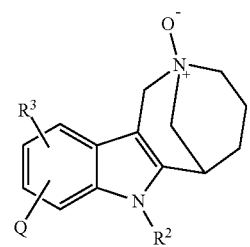
(III-b-6)

(III-b-7)
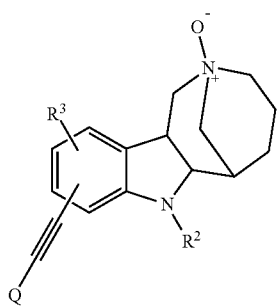
(III-b-8)
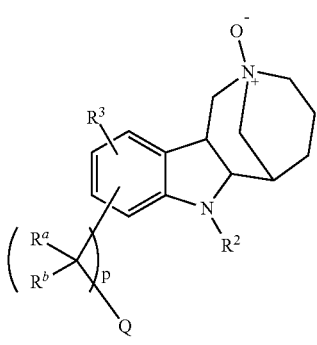
(III-b-9)
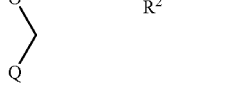
(III-b-10)
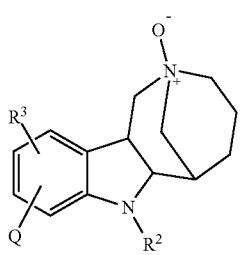
In another embodiment, compounds of formula (IV) can include, but are not limited to compounds of formula (IV-a).
(IV-a)
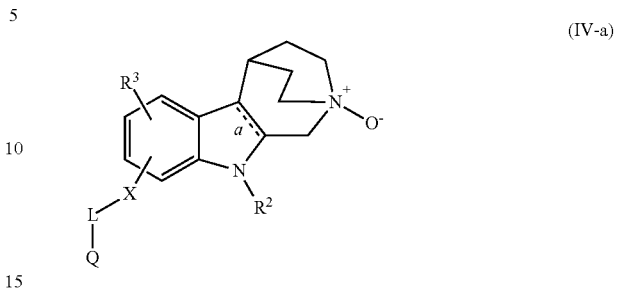
In a further embodiment, compounds of formula (IV-a) can include, but are not limited to compounds of formula (IV-a-1), (IV-a-2), (IV-a-3), (IV-a-4), (IV-a-5), (IV-a-6), (IV-a-7), (IV-a-8), (IV-a-9), or (IV-a-10).
(IV-a-1)
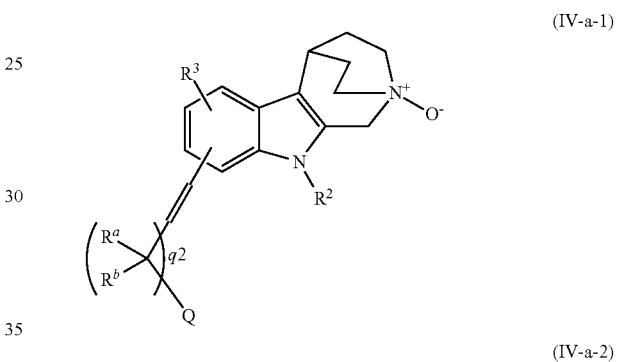
(IV-a-2)
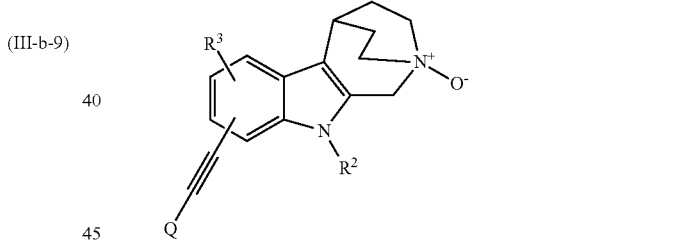
(IV-a-3)
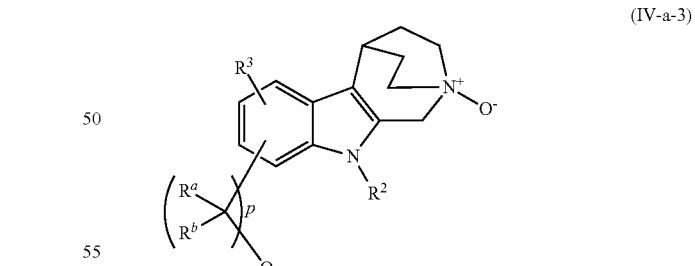
(IV-a-4)
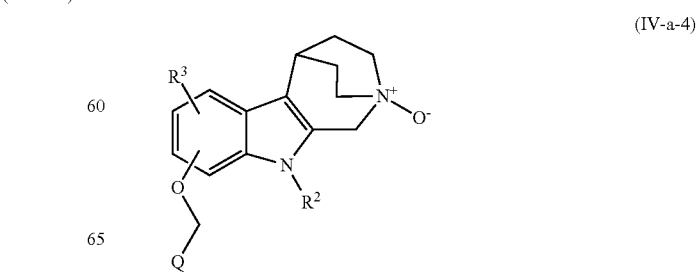

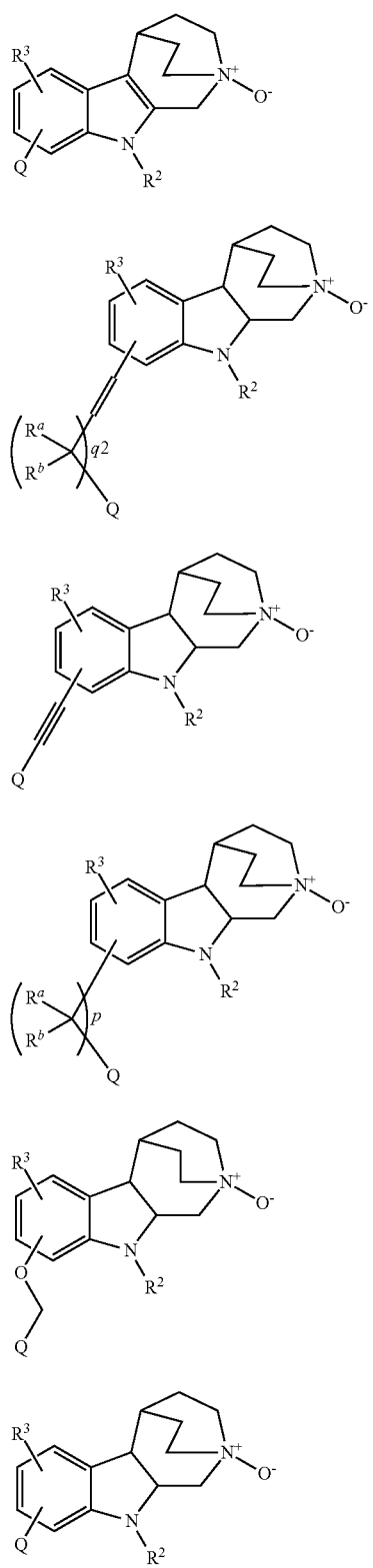
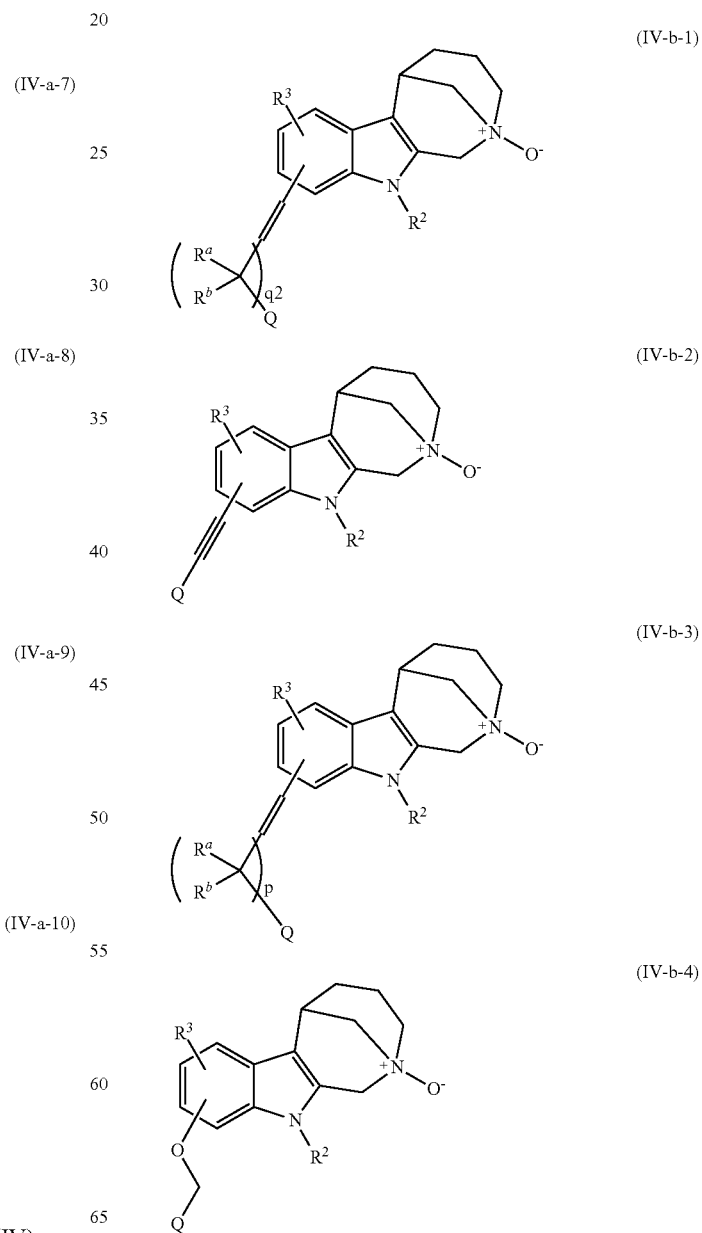
In a further embodiment, compounds of formula (IV-b) can include, but are not limited to compounds of formula (IV-b-1), (IV-b-2), (IV-b-3), (IV-b-4), (IV-b-5), (IV-b-6), (IV-b-7), (IV-b-8), (IV-b-9), or (IV-b-10).
In another embodiment, compounds of formula (IV) can include, but are not limited to compounds of formula (IV-b).

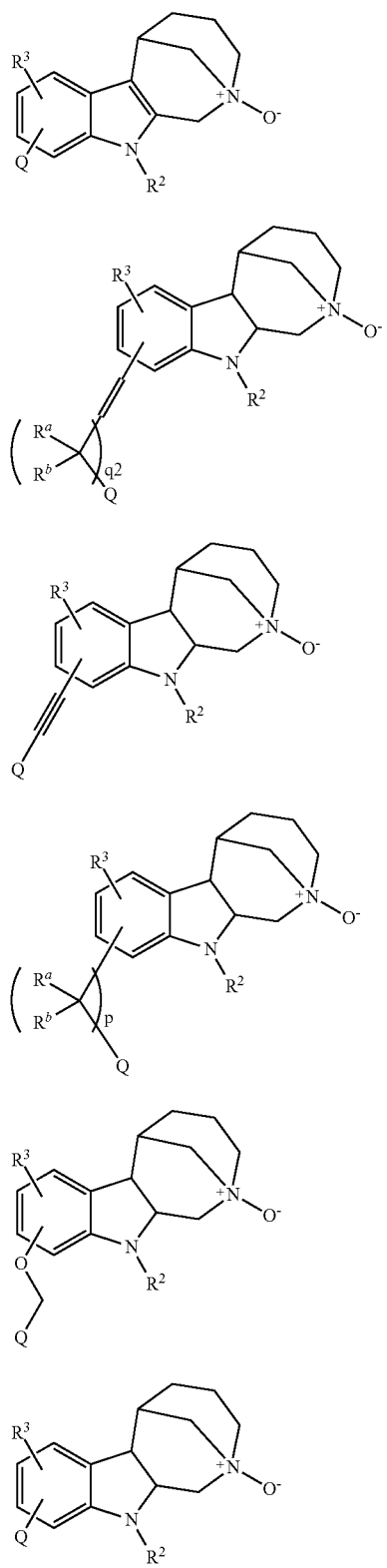
In another embodiment, compounds of formula (III) can include, but are not limited to compounds of formula (III-c).
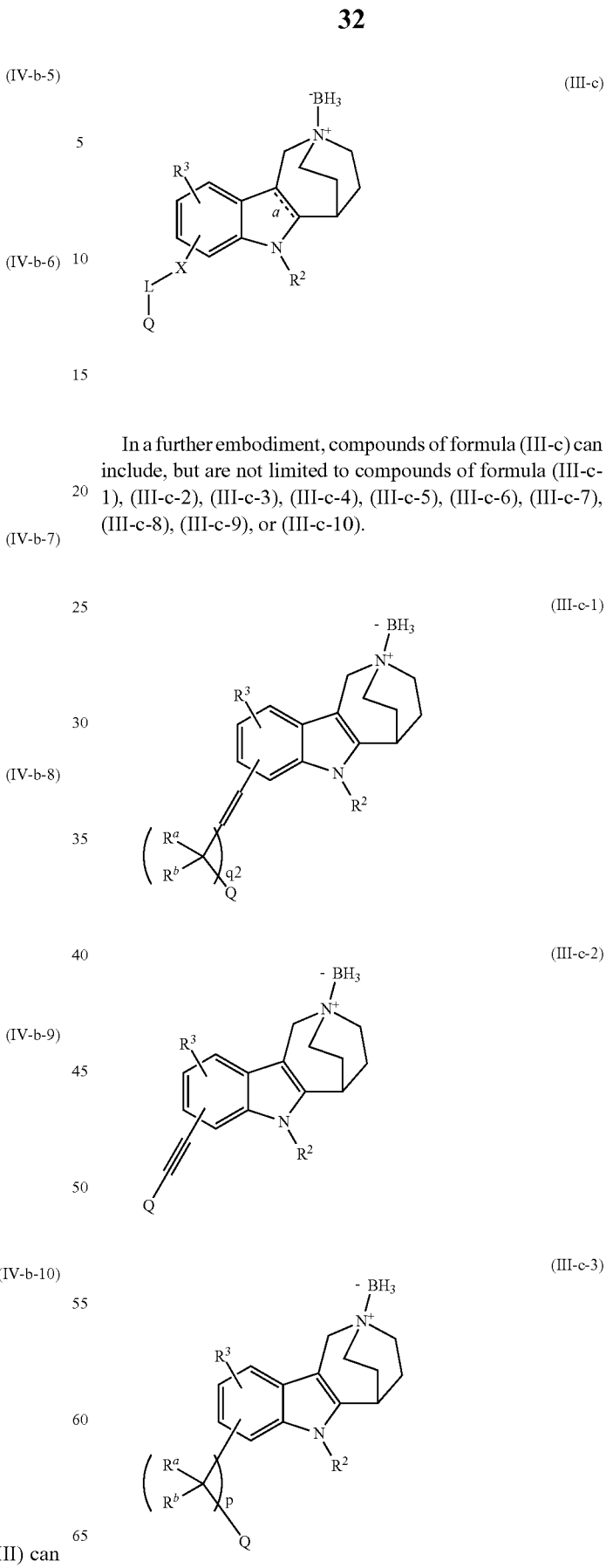
In a further embodiment, compounds of formula (III-c) can include, but are not limited to compounds of formula (III-c-1), (III-c-2), (III-c-3), (III-c-4), (III-c-5), (III-c-6), (III-c-7), (III-c-8), (III-c-9), or (III-c-10).

-continued
(III-c-4)
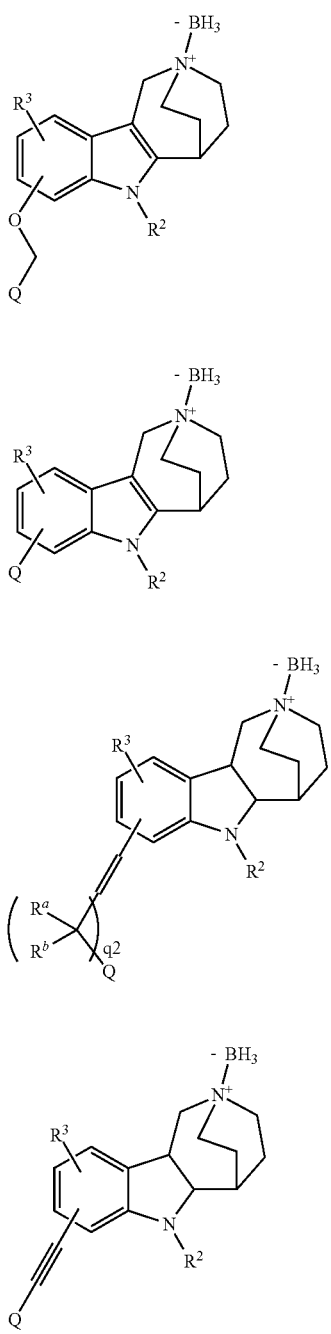
(III-c-5)
(III-c-6)
(III-c-7)
(III-c-8)
(III-c-9)
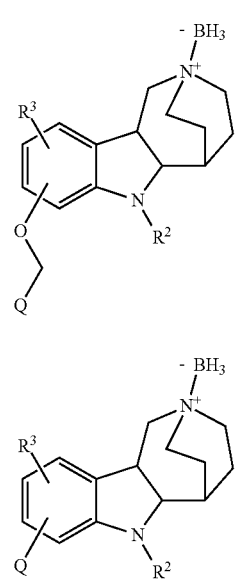
(III-c-10)
In another embodiment, compounds of formula (III) can include, but are not limited to compounds of formula (III-d).
(III-d)
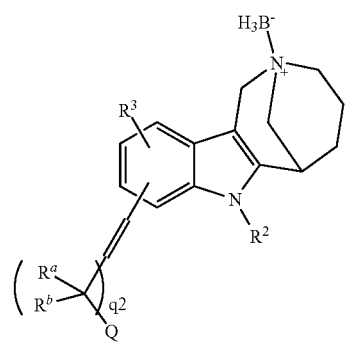
In a further embodiment, compounds of formula (III-d) can include, but are not limited to compounds of formula (III-d-1), (III-d-2), (III-d-3), (III-d-4), (III-d-5), (III-d-6), (III-d-7), (III-d-8), (III-d-9), or (III-d-10).
(III-d-1)

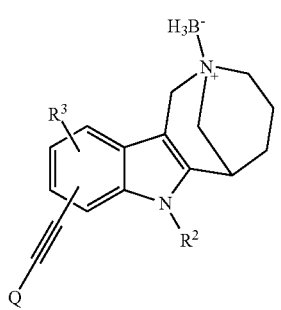
(III-d-2)
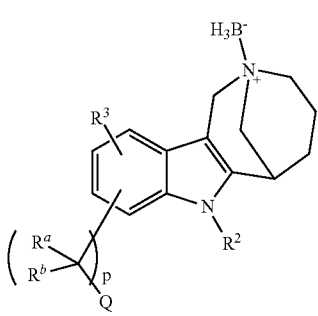
(III-d-3)
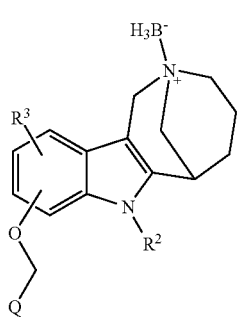
(III-d-4)
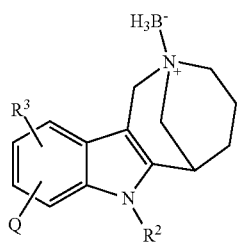
(III-d-5)
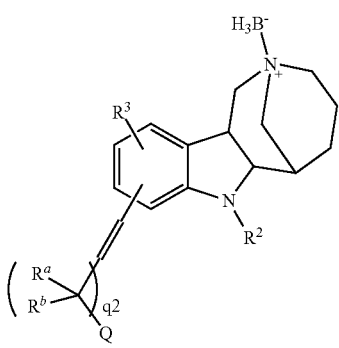
(III-d-6)
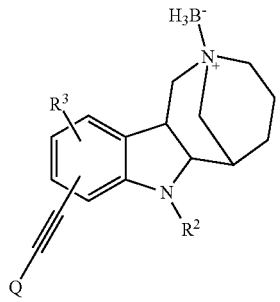
(III-d-7)
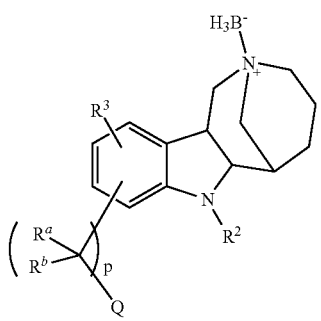
(III-d-8)
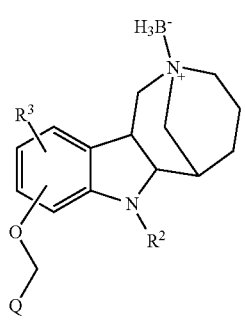
(III-d-9)
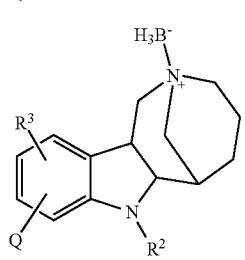
(III-d-10)
In another embodiment, compounds of formula (IV) can include, but are not limited to compounds of formula (IV-c).
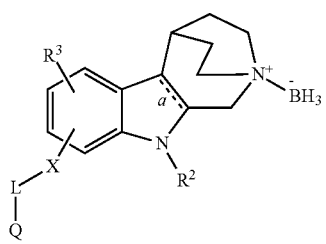
(IV-c)

In a further embodiment, compounds of formula (IV-c) can include, but are not limited to compounds of formula (IV-c-1), (IV-c-2), (IV-c-3), (IV-c-4), (IV-c-5), (IV-c-6), (IV-c-7), (IV-c-8), (IV-c-9), or (IV-c-10).
(IV-c-1)
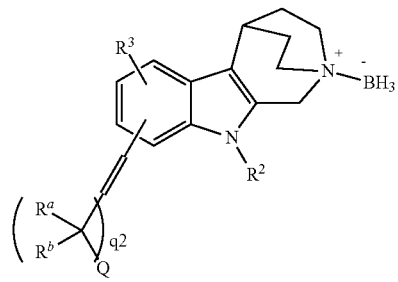
(IV-c-2)
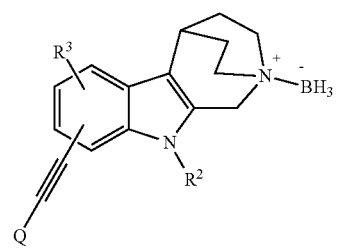
(IV-c-3)
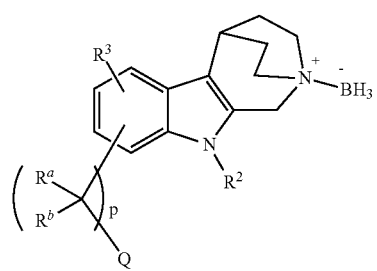
(IV-c-4)
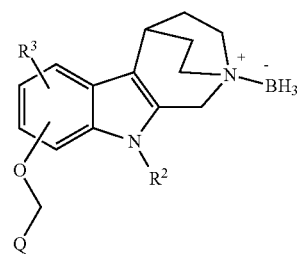
(IV-c-5)
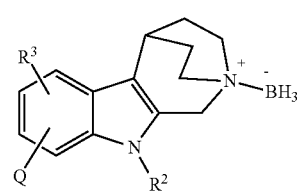
(IV-c-6)
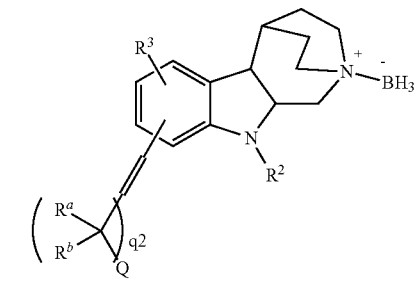
(IV-c-7)
(IV-c-8)
(IV-c-9)
(IV-c-10)
In another embodiment, compounds of formula (IV) can include, but are not limited to compounds of formula (IV-d).

(IV-d)
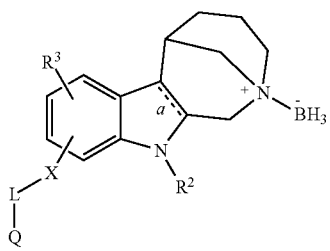
In a further embodiment, compounds of formula (IV-d) can include, but are not limited to compounds of formula (IV-d-1), (IV-d-2), (IV-d-3), (IV-d-4), (IV-d-5), (IV-d-6), (IV-d-7), (IV-d-8), (IV-d-9), or (IV-d-10).
(IV-d-1)
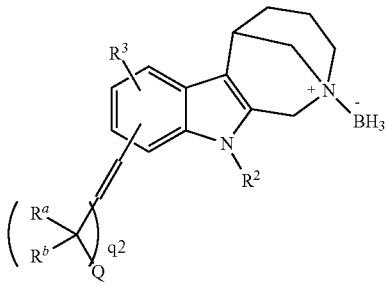
(IV-d-2)
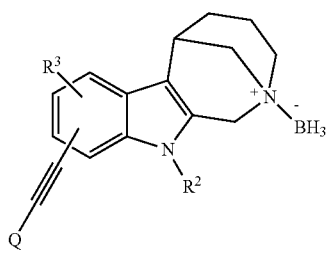
(IV-d-3)
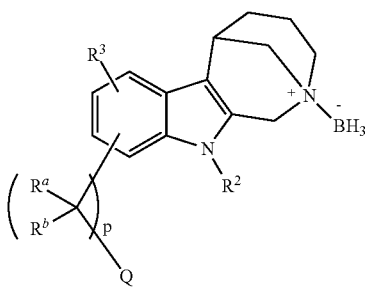
(IV-d-4)
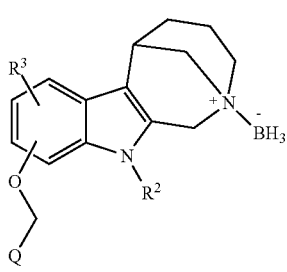
(IV-d-5)
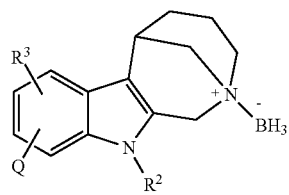
(IV-d-6)
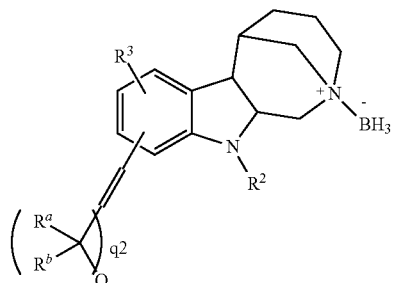
(IV-d-7)
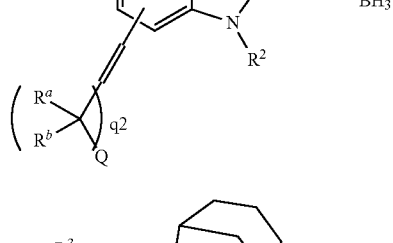
(IV-d-8)
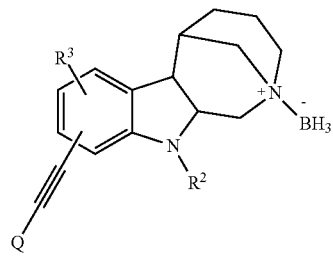
(IV-d-9)
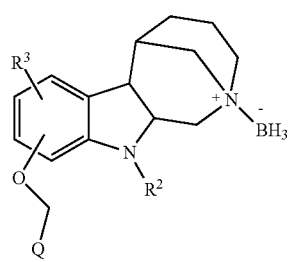
(IV-d-10)
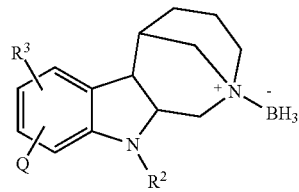
Specific embodiments of compounds contemplated as part of the invention include, but are not limited to:
7-[(E)-2-(6-methylpyridin-3-yl)vinyl]-3,4,5,6-tetrahydro-1H-2,5-ethanoazepino[4,3-b]indole;

7-[2-(6-methylpyridin-3-yl)ethyl]-3,4,5,6-tetrahydro-1H-2,5-ethanoazepino[4,3-b]indole;
7-[(6-methylpyridin-3-yl)ethynyl]-3,4,5,6-tetrahydro-1H-2,5-ethanoazepino[4,3-b]indole;
7-[(E)-2-(4-chlorophenyl)vinyl]-3,4,5,6-tetrahydro-1H-2,5-ethanoazepino[4,3-b]indole;
7-[(1E)-5-phenylpent-1-enyl]-3,4,5,6-tetrahydro-1H-2,5-ethanoazepino[4,3-b]indole;
7-[(E)-2-thien-3-ylvinyl]-3,4,5,6-tetrahydro-1H-2,5-ethanoazepino[4,3-b]indole;
7-(5-phenylpentyl)-3,4,5,6-tetrahydro-1H-2,5-ethanoazepino[4,3-b]indole;
9-[(E)-2-(6-methylpyridin-3-yl)vinyl]-3,4,5,6-tetrahydro-1H-2,5-ethanoazepino[4,3-b]indole;
9-[2-(6-methylpyridin-3-yl)ethyl]-3,4,5,6-tetrahydro-1H-2,5-ethanoazepino[4,3-b]indole;
7-[(E)-2-(4-fluorophenyl)vinyl]-3,4,5,6-tetrahydro-1H-2,5-ethanoazepino[4,3-b]indole;
7-[(E)-2-pyridin-4-ylvinyl]-3,4,5,6-tetrahydro-1H-2,5-ethanoazepino[4,3-b]indole;
7-[(E)-2-pyridin-2-ylvinyl]-3,4,5,6-tetrahydro-1H-2,5-ethanoazepino[4,3-b]indole;
7-(pyridin-3-ylethynyl)-3,4,5,6-tetrahydro-1H-2,5-ethanoazepino[4,3-b]indole;
7-[(E)-2-(2,4-difluorophenyl)vinyl]-3,4,5,6-tetrahydro-1H-2,5-ethanoazepino[4,3-b]indole;
7-[(E)-2-(3-fluorophenyl)vinyl]-3,4,5,6-tetrahydro-1H-2,5-ethanoazepino[4,3-b]indole;
7-[2-(3-fluorophenyl)ethyl]-3,4,5,6-tetrahydro-1H-2,5-ethanoazepino[4,3-b]indole;
8-[(E)-2-(6-methylpyridin-3-yl)vinyl]-3,4,5,6-tetrahydro-1H-2,5-ethanoazepino[4,3-b]indole;
10-[(E)-2-(6-methylpyridin-3-yl)vinyl]-3,4,5,6-tetrahydro-1H-2,5-ethanoazepino[4,3-b]indole;
7-[(E)-2-phenylvinyl]-3,4,5,6-tetrahydro-1H-2,5-ethanoazepino[4,3-b]indole;
7-{[4-(trifluoromethoxy)phenyl]ethynyl}-3,4,5,6-tetrahydro-1H-2,5-ethanoazepino[4,3-b]indole;
7-(pyridin-4-ylethynyl)-3,4,5,6-tetrahydro-1H-2,5-ethanoazepino[4,3-b]indole;
8-[(6-methylpyridin-3-yl)ethynyl]-3,4,5,6-tetrahydro-1H-2,5-ethanoazepino[4,3-b]indole;
10-[(6-methylpyridin-3-yl)ethynyl]-3,4,5,6-tetrahydro-1H-2,5-ethanoazepino[4,3-b]indole;
9-fluoro-7-[(6-methylpyridin-3-yl)ethynyl]-3,4,5,6-tetrahydro-1H-2,5-ethanoazepino[4,3-b]indole;
9-fluoro-7-[(E)-2-(6-methylpyridin-3-yl)vinyl]-3,4,5,6-tetrahydro-1H-2,5-ethanoazepino[4,3-b]indole;
7-(benzyloxy)-3,4,5,6-tetrahydro-1H-2,5-ethanoazepino[4,3-b]indole;
7-quinolin-6-yl-3,4,5,6-tetrahydro-1H-2,5-ethanoazepino[4,3-b]indole;
7-[(E)-2-(6-methylpyridin-3-yl)vinyl]-1,2,3,4,5,6-hexahydro-2,5-ethanoazepino[4,3-b]indole 2-oxide;
7-[(E)-2-pyrimidin-5-ylvinyl]-3,4,5,6-tetrahydro-1H-2,5-ethanoazepino[4,3-b]indole;
7-[(Z)-2-pyrimidin-5-ylvinyl]-3,4,5,6-tetrahydro-1H-2,5-ethanoazepino[4,3-b]indole;
7-[(Z)-2-(6-methylpyridin-3-yl)vinyl]-3,4,5,6-tetrahydro-1H-2,5-ethanoazepino[4,3-b]indole;
9-[(E)-2-(6-methylpyridin-3-yl)vinyl]-3,4,5,10-tetrahydro-1H-2,5-ethanoazepino[3,4-b]indole;
9-[2-(6-methylpyridin-3-yl)ethyl]-3,4,5,10-tetrahydro-1H-2,5-ethanoazepino[3,4-b]indole;
7-[(E)-2-pyridin-3-ylvinyl]-3,4,5,6-tetrahydro-1H-2,5-ethanoazepino[4,3-b]indole;
8-[(E)-2-(6-methylpyridin-3-yl)vinyl]-1,3,4,5,6,7-hexahydro-2,6-methanoazocino[4,3-b]indole;
(cis)-7-[(E)-2-(6-methylpyridin-3-yl)vinyl]-3,4,5,5a,6,10b-hexahydro-1H-2,5-ethanoazepino[4,3-b]indole;
7-(6-methylpyridin-3-yl)-3,4,5,6-tetrahydro-1H-2,5-ethanoazepino[4,3-b]indole;
7-(pyrimidin-5-yl)-3,4,5,6-tetrahydro-1H-2,5-ethanoazepino[4,3-b]indole;
7-(pyridin-3-yl)-3,4,5,6-tetrahydro-1H-2,5-ethanoazepino[4,3-b]indole;
7-(pyridin-4-yl)-3,4,5,6-tetrahydro-1H-2,5-ethanoazepino[4,3-b]indole; or
7-(quinolin-3-yl)-3,4,5,6-tetrahydro-1H-2,5-ethanoazepino[4,3-b]indole.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the compounds of the present invention. The present invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the present invention encompasses any tautomeric or stereoisomeric form, and mixtures thereof, and is not to be limited merely to any one tautomeric or stereoisomeric form utilized within the naming of the compounds or formulae drawings.

The present invention also includes isotopically-labeled compounds, which are identical to those recited in formula (I), formula (II), formula (III) or formula (IV), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

c. Biological Data

To determine the effectiveness of compounds having a formula (I), formula (II), formula (III), or formula (IV), these compounds can be evaluated in vitro models of cellular function and in vivo models of pro-cognitive effects.

Abbreviations which have been used in the descriptions of Biological Data that follow are: DMEM for Dulbecco's modified Eagle's medium; DMSO for dimethyl sulfoxide; FBS for fetal bovine serum; FITC for fluoroscein isothiocyanate; FLIPR for fluorometric imaging plate reader; GFAP for glial fibrillary acidic protein; HBSS for Hank's balanced salt solution; i.p. for intraperitoneal; NGF for nerve growth factor; PBS for phosphate buffered saline; and TRITC for tetramethylrhodamine isothiocyanate.

(i) Effects on Neurite Outgrowth in Neurons and Neuronal Cell Lines:

Effects on cellular properties such as neurite outgrowth and neuronal or neuronal-like cell number, etc. can be measured either using rat or human neuronal/neuroblastoma cell lines (e.g., SH-SY5Y, PC12, IMR-32, etc.) or using primary cells (e.g., rat cortical neurons). For example, it has been reported that dimebolin can increase neurite outgrowth in primary rat cortical neurons, comparable to that evoked by Brain Derived Neurotrophic factor (BDNF) (Hung, D. Dimebon: A phase 3 investigational agent for Alzheimer's disease with a novel mitochondrial mechanism of action. Presented at the International Conference on Alzheimer's Disease, Chicago, Ill., USA, July 2008; paper S4-04-05.).

For example, studies can be conducted using PC12 cells plated in 96-well plates, treated with or without nerve growth factor (100 ng/mL) for 6 days. Compounds are then added at various concentrations (ranging from 0.1 nM to 30 µM), and incubated for 24 hours. Cells are then fixed and stained by neuron marker β-tubulin (green), and nuclei were stained by Hoechst 33342 (blue). Images are collected using the ImageXpress Micro automatic fluorescent microscopy system (Molecular Devices, Sunnyvale, Calif.) employing a Nikon 10× Plan Fluor objective and Cool Snap HQ CCD camera. The Neurite Outgrowth module in the MetaMorph Imaging software can be used to automatically count neuron-like number, and the extent of neurite outgrowth.

In addition to PC12 cells, other cellular model systems may also be used. Rat cortical cells can be cultured and prepared for high content microscopy analysis as previously described (Hu, M.; Schurdak, M. E.; et al. High content screen microscopy analysis of $A\beta_{1-42}$-induced neurite outgrowth reduction in rat primary cortical neurons: Neuroprotective effects of α7 neuronal nicotinic acetylcholine receptor ligands. *Brain Res.* 2007, 1151, 227-235.). Briefly, cortical cell cultures are plated at density of 5×10$^5$ cells/mL onto poly-D-lysine coated 96-well plates and maintained in a cell incubator at 37° C. with 5% $CO_2$. Experiments are performed using 6-7 day-old cortical cell cultures by treating with test compounds. In some experiments, the effect of test compounds on reversing Aβ toxicity can also be measured (Hu, M.; Schurdak, M. E.; et al. High content screen microscopy analysis of $A\beta_{1-42}$-induced neurite outgrowth reduction in rat primary cortical neurons: Neuroprotective effects of α7 neuronal nicotinic acetylcholine receptor ligands. *Brain Res.* 2007, 1151, 227-235.). For assessment of neuroprotective effects, cells are first pretreated with test compounds for about 5 hours. Medium is then replaced with the medium containing freshly prepared about 5 µM $A\beta_{1-42}$ peptide in the absence or presence of the test compounds for 3 days. The untreated group contains the same percentage of vehicle (DMSO) as in the treatment groups. Cells are fixed with approximately 4% paraformaldehyde containing 0.5% Hoechst 33342 for about 15 minutes, followed by three washes using PBS (pH 7.4) and blocked with 10% donkey serum in PBS for 1 hour at room temperature. The cells are then incubated overnight at about 4° C. with mouse anti-tubulin monoclonal antibody (1:100) for staining neurons and rabbit anti-GFAP (1:1000) for staining glia. In the next day, cells are incubated with FITC-labeled anti-mouse and TRITC-labeled anti-rabbit antibodies (1:1000) for about 1 hour at room temperature. After fixing and staining the cells, nuclei (360/400 nm excitation and 465/300 nm emission filters), neuron (475/350 nm excitation and 535/400 nm emission filters) and glial cell (535 nm excitation and 610 nm emission filters) images are collected using the ImageExpress Micro automatic fluorescent microscopy system (Molecular Devices, Sunnyvale, Calif.) employing a Nikon 10× Plan Fluor objective and Cool Snap HQ CCD camera. The Neurite Outgrowth module in the MetaMorph Imaging software can be used to automatically count total cell number, number of neuron cells, and the extent of neurite outgrowth.

Exposure to $A\beta_{1-42}$ resulted in reduction of neurite outgrowth in primary postnatal (P0) cortical cells. The neurite outgrowth observed for untreated cells is set to 100% response. Treatment of cells with compounds prior to and concomitantly with $A\beta_{1-42}$ gave a neuroprotective effect with neurite outgrowth maintained or enhanced relative to untreated cells.

Table 1 shows the maximum response at the noted test compound concentration relative to 300 nM dimebolin.

TABLE 1

Neurite Outgrowth Assay

| Example | Maximum Effect (of % 300 nM Dimebolin) at Concentration (nM) | % Attenuation Effect of 5 µM Aβ 1-42 |
|---|---|---|
| 1 | 106% at 3000 nM | 34 |
| 3 | 115% at 3000 nM | 43 |
| 8 | 121% at 300 nM | 49 |
| 27 | 109% at 300 nM | 38 |

(ii) Effects on $A\beta_{1-42}$ Induced Tau Phosphorylation in PC12 Cells

The effect of test compound(s) on $A\beta_{1-42}$ induced tau phosphorylation can be assessed in a cell line such as PC12 as previously described (Hu, M.; Waring, J. F.; et al. Role of GSK-3β activation and α7 nAChRs in $A\beta_{1-42}$-induced tau phosphorylation in PC12 cells. *J. Neurochem.* 2008, 106 (3), 1371-1377.). Briefly, PC12 cells are plated on poly-D-lysine coated 96-well plates, cultured in Ham's F12K medium supplemented with 15% horse serum, 2.5% FBS, 2 mM L-glutamine, 100 U/mL penicillin and 100 µg/mL streptomycin at 37° C. with 5% $CO_2$ and differentiated with 100 ng/mL NGF for approximately 6 days. Cells are pretreated with test compounds for 30 minutes at about 37° C. The medium is then replaced with that containing freshly prepared $A\beta_{1-42}$ or control peptide in the absence or presence of the test compounds and the cells are incubated at 37° C. for 24 hours. Cells are fixed with 3.7% formaldehyde in PBS (pH 7.4) for about 1 hour at room temperature followed by permeabilization by three washes with 0.1% Triton-X 100 in PBS. The fixed cells are incubated with blocking buffer for about 2 hours at room temperature followed by overnight incubation with primary antibodies AT8 (for phosphorylated tau), anti-human tau (for total Tau), or anti-GSK-3β. On the next day, cells are washed 3 times with 0.1% Tween-20 in PBS, then incubated with IRDye® 800CW anti-mouse IgG antibodies (1:100) for 1 hour at room temperature for detection of phosphorylated tau (p-tau) or GSK-3β, or with the Alexa Fluor® 680 anti-rabbit antibodies (1:100) for detection of total tau (t-tau). Cells are then washed three times, and the target signals are simultaneously visualized using Odyssey Infrared Imaging Scanner with the 680-nm fluorophore emitting an image of red color and the 800-nm fluorophore emitting an image of green color. The integrated fluorescence intensities are calculated and analyzed using the Odyssey Infrared Imaging System Application Software version 1.2.15 (Li-Cor Biosciences (Lincoln, Nebr.). The p-tau and t-tau levels are typically presented as the ratio p-tau/t-tau (Hu, M.; Waring, J. F.; et al. Role of GSK-3β activation and α7 nAChRs in $A\beta_{1-42}$-induced tau phosphorylation in PC12 cells. *J. Neurochem.* 2008, 106(3), 1371-1377.).

(iii) Effects on Mitochondrial Function

The method also involves a high-throughput assay using serum-deprivation conditions involving neuronal cells to screen for compounds that increase or preserve mitochondrial membrane potential. Such compounds can be found to aid in rescuing cells from energy-depletion that occurs in several neurodegenerative states. Mitochondrial-mediated apoptosis occurs in response to a wide range of apoptotic stimuli including p53, c-myc, DNA damage, prooxidants, chemotherapeutic agents, serum starvation and death receptor activation (Lin C-H., Lu Y-Z., Cheng, F-C., Chu L-F. and Hsueh C-M. (2005) Bax-regulated mitochondrial-mediated apoptosis is responsible for the in vitro ischemia induced neuronal cell death of Sprague Dawley rat. (Neuroscience Letter 387:22-27).

Serum deprivation for 16-18 hours initiates the early stages of apoptosis (Chavier D, Lecoeur H, Langonne A, Borgne-Sanchez A, Mariani J., Martinou J-C, Rebouillat D and Jacotot E. Upstream control of apoptosis by caspase-2 in serum-deprived neurons. Apoptosis 10:1243-1259, 2005) and induces stress on a cell before full commitment to cell death. Mitochondria play a critical role in the cell for survival or death due to their regulation of both energy metabolism as well as apoptosis (Sullivan P G, Rabchevsky A G, Waldmeirer P C and Springer J E. Mitochondrial Permeability Transition in CNS Trauma: Cause or Effect of Neuronal Cell Death. J Neuroscience Res 2005, 79:231-239). One of the first major events to occur in apoptosis is the breakdown of the membranes of the mitochondria to release cytochrome c, activate caspases, change electron transport and cause a decrease in mitochondrial membrane potential ($\Delta\psi_m$). A change in $\Delta\psi_m$ therefore serves as a measure of mitochondrial function and indicator of cell health.

Thus, this stress inducer, serum deprivation, combined with monitoring changes in the mitochondrial membrane potential in a 96-well format allows for the establishment of an efficient high-throughput screen (HTS) in order to evaluate the ability of compounds to increase mitochondrial membrane potential in the presence of stress and preserve health of the cell. Exemplary procedures for conducting such high-throughput assay are provided below.

Tissue Culture: SK-N-SH human neuroblastoma cells obtained from American Type Culture Collection (Rockville, Md.) were maintained in the log phase of growth in Minimal Essential Media (MEM), 10% heat inactivated fetal calf serum and 100 units/mL antibiotic-antimycotic (AA). Cells were cultured and maintained in a humidified incubator at 37° C. under 5% $CO_2$ and 95% air. Cells were trypsinized (0.25%) and subcultured every 3 days and used from 15-18 passages. All cell culture supplies were obtained from Invitrogen (Carlsbad, Calif.).

Serum Deprivation/JC-1 Mitochondrial Membrane Potential (MMP) Assay.

SK-N-SH cells were plated 2-3 days in advance at a concentration of 50,000 cells/well onto collagen coated black-walled 96 well plates (Becton-Dickinson, Bedford, Mass.) in a total volume of 200 μL. On day of experimental treatment, the media containing serum was aspirated from each well and rinsed once with MEM/1% AA without serum. The cells then were incubated overnight in 100 μL of MEM/1% AA (no serum) with and without dimebolin or novel chemical entities overnight for ~18 hours. The following day, JC-1 dye (5,5',6,6'-tetrachloro-1,1',3,3'-tetraethylbenzimidazolcarbocyanide) was diluted 1:10 into MEM media according to the JC-1 Mitochondrial Membrane Potential Assay Kit: (Cayman Chemical Company, Ann Arbor, Mich.) and then 10 μL of the JC-1 dye solution was added to each well. The plates were centrifuged for 5 minutes at 400×g at room temperature followed by 40 minute incubation at 37° C. The plates were washed twice with 200 μL of provided Assay Buffer followed an addition of 100 μL of Assay Buffer to each well. The plates were read with an excitation and emission of 560 nM and 595 nM for red fluorescence and with an excitation and emission of 495 mM and 535 nM for green fluorescence to determine the final JC-1 value taking the red to green fluorescence ratio. This assay is based on change in mitochondrial membrane potential (MMP) using this lipophilic cationic dye, JC-1, by monitoring the changes in the ratio of red to green fluorescence as the MMP depolarizes. This change in MMP reflects the health of the cell with healthy, viable cells have a high JC-1 ratio and high MMP whereas apoptotic, unhealthy cells have a low JC-1 ratio or low MMP.

For the ability of compounds to reverse the stress due to serum deprivation and increase the JC-1 ratio, the percent maximal intensity in JC-1 ratio was normalized to that induced by the peak value for 10 μM dimebolin and plotted against the compound concentration to calculate $EC_{50}$ values and to control for plate-to-plate variability. Concentration-response data were analyzed using GraphPad Prism (San Diego, Calif.); the $EC_{50}$ values were derived from a single curve fit to the mean data of n=2-3, in duplicates. Selected data is shown in Table 2.

All compounds were dissolved in dimethyl sulfoxide at 10 mM stock solutions and tested at a concentration that the dimethyl sulfoxide levels never exceeded 1%.

TABLE 2

JC-1 Mitochondrial Membrane Potential (MMP) Assay

| Example | $EC_{50}$ (μM) | JC-1 max % |
|---|---|---|
| 1 | 6.02 | 139 |
| 2 | 5.22 | 170 |
| 3 | 4.36 | 188 |
| 4 | 4.09 | 123 |
| 5 | 5.27 | 58 |

TABLE 2-continued

JC-1 Mitochondrial Membrane Potential (MMP) Assay

| Example | EC$_{50}$ (µM) | JC-1 max % |
|---|---|---|
| 6 | 6.62 | 67 |
| 7 | 1.43 | 62 |
| 8 | 4.05 | 162 |
| 9 | 3.94 | 110 |
| 10 | 4.74 | 84 |
| 11 | 6.73 | 171 |
| 12 | 3.56 | 192 |
| 13 | 5.17 | 142 |
| 14 | >30 | 39 |
| 15 | >30 | 44 |
| 16 | >30 | 49 |
| 17 | 15.12 | 5.33 |
| 18 | 3.10 | 173 |
| 19 | 3.52 | 64 |
| 20 | >30 | 47 |
| 21 | 3.69 | 104 |
| 22 | 8.66 | 185 |
| 23 | 7.27 | 140 |
| 24 | 5.38 | 156 |
| 25 | 3.42 | 127 |
| 26 | 9.81 | 494 |
| 27 | 6.39 | 133 |
| 28 | >30 | 50 |
| 29 | 5.33 | 54 |
| 30 | >30 | 29 |
| 31 | 7.75 | 120 |
| 32 | 3.64 | 199 |
| 33 | 6.01 | 197 |
| 34 | 6.30 | 109 |
| 35 | 7.28 | 213 |
| 36 | 6.89 | 196 |
| 37 | 8.66 | 179 |
| 38 | 10.5 | 76 |
| 39 | 10.3 | 113 |
| 40 | 8.99 | 92 |
| 41 | 3.68 | 171 |

(iv) In Vivo Models of Procognitive Effects

A range of animal models capturing diverse cognitive domains may be utilized for assessing procognitive effects of compounds. Examples of these models are provided in Bitner et al., (Bitner, R. S.; Bunnelle, W. H.; et al. Broad-spectrum efficacy across cognitive domains by α7 nicotinic acetylcholine receptor agonism correlates with activation of ERK1/2 and CREB phosphorylation pathways. *J. Neurosci.* 2007, 27 (39), 10578-10587.). Various transgenic animal models that are relevant of neurodegenerative diseases of interest may also be utilized to assess effects of test compounds (Goetz, J.; Ittner, L. M. Animal models of Alzheimer's disease and frontotemporal dementia. *Nat. Rev. Neurosci.* 2008, 9 (7), 532-544.).

Figure 2:
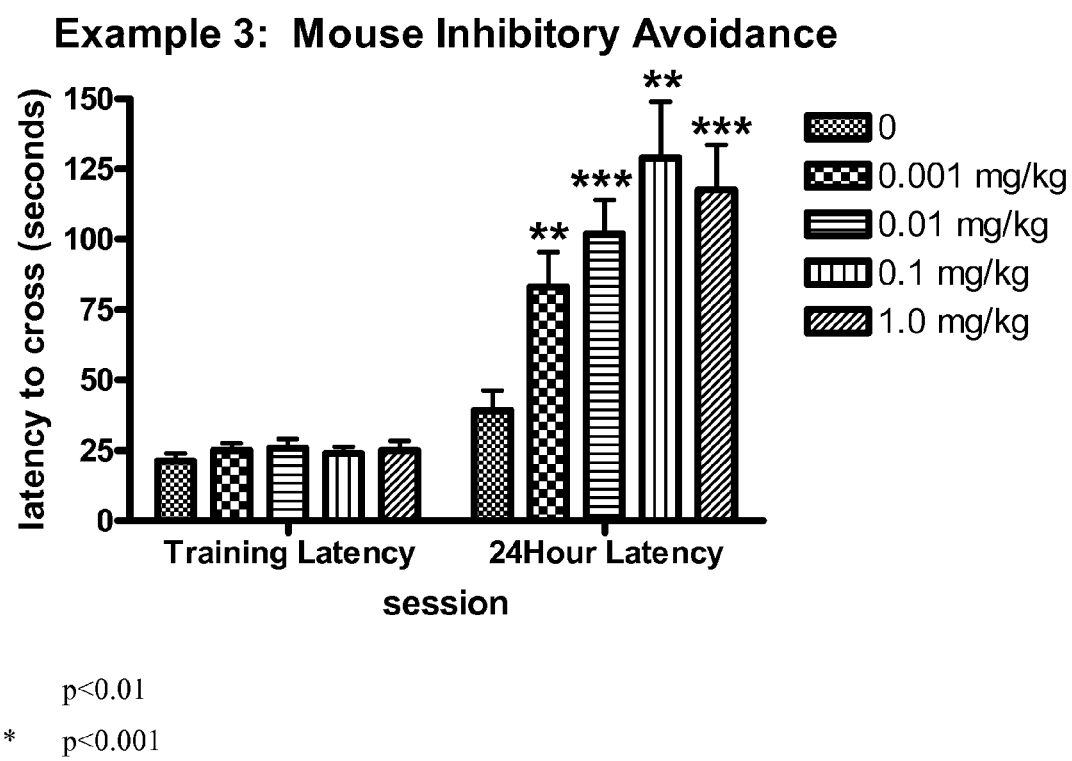
FIG. 2 shows a graphical representation of the concentration-dependent improvement in mouse 24-hour recall inhibitory avoidance scores upon treatment with test compound (Example 3). The X-axis represents the day of exposure to condition, and the Y-axis represents the latency to cross to the punished side.

Inhibitory Avoidance in Mouse: The inhibitory avoidance task involves the uses of a two-compartment step through apparatus (Ugo Basile, Collegeville, Pa.) that measures the animal's ability to remember a brief noxious stimulus (foot shock), and is considered a measure of trial learning, and memory consolidation. Briefly, 30 minutes after dosing, mice were placed in a lighted compartment of the apparatus where the latency to enter into the preferred dark compartment is recorded. Entry into a dark compartment results in the immediate delivery of a mild foot shock (0.2 mA, 1-second duration). Retention testing is conducted 24 hours later with the animal again placed in the lighted compartment where its latency to reenter the dark side of the apparatus is measured (no shock). Increasing retention latency is regarded as an index of memory consolidation (Bitner, R. S.; Bunnelle, W. H.; et al. Broad-spectrum efficacy across cognitive domains by α7 nicotinic acetylcholine receptor agonism correlates with activation of ERK1/2 and CREB phosphorylation pathways. *J. Neurosci.* 2007, 27 (39), 10578-10587.). As shown in FIG. 1, the latency to reenter the dark side (punishment side) is significantly increased 24 hours after initial exposure with Example 1 at the doses 0.001, 0.01, 0.1, and 1.0 mg/kg i.p. Similarly, as shown in FIG. 2, the latency to reenter the dark side (punishment side) is significantly increased 24 hours afar initial exposure with Example 3 at 0.001, 0.01, 0.1, and 1.0 mg/kg i.p. Statistical significance was first determined using a Kruskal-Wallis nonparametric analysis with post-hoc significance determined using Mann Whitney t-tests. (*p<0.05; p<0.01, *p<0.001 versus control)

Figure 3:
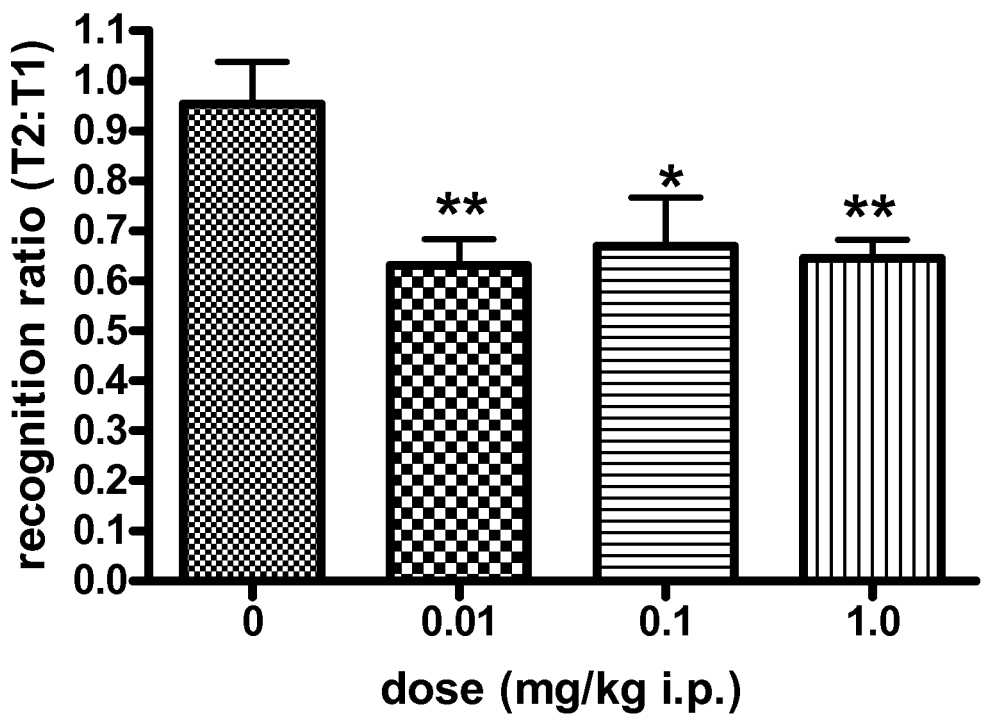
FIG. 3 shows a graphical representation of the concentration-dependent improvement in rat social recognition ratio scores upon treatment with test compound (Example 1). The X-axis represents the test concentrations, and the Y-axis represents the recognition ratio (T2:T1).

Social Recognition in Rat: The social recognition test measures short-term memory on the basis of olfactory cues, and depends on the hippocampus. Adult (350-450 g) rats are allowed to interact with a juvenile (60-80 g) rat for a 5 minute interaction trial (T1) in which the adult exhibits behaviors that included close following, grooming and/or sniffing of the juvenile for as much as 40-50% of the trial duration. The juvenile rat is then removed and the adult rat immediately administered various doses of test compound. A second 5 minute recognition trial (T2) is conducted 120 minutes later where interactive behavior of the adult rat is again monitored. If recognition memory is lost over the 120 minute interval between trials, the interactive behavior would be similar for the two trials; however, if memory is retained, the recognition ratio (T2:T1) would decline, i.e. decreasing T2:T1 ratio is regarded as an index of improved short-term recognition memory (Bitner, R. S.; Bunnelle, W. H.; et al. Broad-spectrum efficacy across cognitive domains by α7 nicotinic acetylcholine receptor agonism correlates with activation of ERK1/2 and CREB phosphorylation pathways. *J. Neurosci.* 2007, 27 (39), 10578-10587. Timmermann, D. B.; Groenlien, J. H.; et al. An allosteric modulator of the α7 nicotinic acetylcholine receptor possessing cognition-enhancing properties in vivo. *J. Pharmacol. Exp. Ther.* 2007, 323 (1), 294-307.). As shown in FIG. 3, the recognition ratio (T2:T1) declined significantly upon dosing intraperitoneally with Example 1 at 0.01, 0.1 and 1.0 mg/kg. Statistical significance was determined using a one-way ANOVA with post-hoc significance determined using Dunett's multiple comparison (*p<0.05; **p<0.01 versus control).

Delayed Matching-to-Sample (DMTS) Titration in Monkey: Studies can be conducted in Rhesus monkeys that were initially trained in the DMTS procedure (Buccafusco, J. J.; Terry, A. V.; et al. Profile of nicotinic acetylcholine receptor agonists ABT-594 and A-582941, with differential subtype selectivity, on delayed matching accuracy by young monkeys. *Biochem. Pharmacol.* 2007, 74 (8), 1202-1211.). Using a touch-sensitive screen in the animals home-cage, trial initiation consists of presentation of one of three colored stimuli (red, blue, or yellow rectangles) that remain in view (sample stimuli) until touched by subject. Following a delay interval, two choice rectangles are presented, one being the previous sample stimulus, in which correct (matching) choice-touch to the sample stimuli is food reinforced. For standard DMTS testing, the duration for each delay interval is adjusted for each subject until three levels of performance accuracy were approximated: zero delay (85-100% of trials answered correctly); short delay interval (75-84% correct); medium delay interval (65-74% correct); and long delay interval (55-64% correct). The titration version of the DMTS task used in the present studies requires the animals to perform a 96 trial session that begins with a 0 sec delay interval. If the trial is answered correctly, a 1 second delay interval is presented during the next trial presented. The 1 second incremental progression is maintained until the subject made an incorrect match. The delay interval for the trial after an incorrect match is always decreased by 1 second. After an incorrect match, if the next trial is answered correctly, then the subsequent trial presented a delay interval 1 second longer in duration. Dependent variables include the overall % of trials answered correctly, the number of trials to reach the maximal delay interval attained, and the maximum and average delay interval attained (in seconds). Compounds are administered prior to DMTS testing.

(v) Determination of Analgesic Effect Against Neuropathic Pain-Chung Model

Animals were prepared for testing, by use of a surgical procedure that induces neuropathic pain in one paw. Male Sprague Dawley rats were purchased from Charles River (Portage, Mich.). Prior to surgery, animals were housed in groups and maintained in a temperature-regulated environment. Following nerve ligation surgery, animals were housed in groups, and had access to food and water ad libitum.

The L5 and L6 spinal nerves of anesthetized rats were tightly ligated in a manner described previously (see Kim and Chung, Pain (1992) vol. 50 pp. 355-363). An incision was made on the dorsal portion of the hip and the muscle was blunt-dissected to reveal the spinal processes. The L6 transverse process was removed, and the left side L5 and L6 spinal nerves were tightly ligated with 5.0 braided silk suture. The wound was cleaned, the membrane sewn with 4.0 dissolvable Vicryl suture and the skin closed with wound clips. The paw affected by the surgical procedure (the left paw) develops an allodynic response, a hypersensitivity to mechanical and other stimuli; neuropathic pain is assessed as an increased sensitivity in the surgically affected (left) allodynic paw compared to the control paw on the right side, and measured by comparing the response of the (left side) allodynic paw to the response of the unaffected right side control paw.

For the assessment of neuropathic pain, mechanical allodynia in the affected paw of animals that had undergone spinal nerve ligation was evaluated using testing with von Frey filaments. As described previously by S. R. Chaplan, et al. ("Quantitative assessment of tactile allodynia in the rat paw" J. Neurosci. Meth. (1994) vol. 53 pp. 55-63), two weeks following surgery rats were acclimated to a testing box constructed of plexiglass with a wire mesh floor which allowed access to the plantar surface of the animal's hindpaws. Using an Up-Down method (Dixon, Annual Rev. Pharmacol. Toxicol. (1980) vol. 20, pp. 441-462; Chaplan et al. "Quantitative assessment of tactile allodynia in the rat paw" J. Neuroscience Methods (1994) vol. 53 pp. 55-63), von Frey filaments of increasing stiffness were applied to the plantar surface of the hindpaws and the withdrawal response of the animals was observed; for the surgically affected paw with neuropathic pain (the left side paw) the baseline level of allodynia has a withdrawal threshold of $\leq 4$ g of pressure. By comparison, for the control paw without allodynia (in this case the right side paw), the typical withdrawal pressure is around 15 g. Representative compounds of the invention, administered intraperitoneally 30 minutes before testing, are able to reduce the symptoms of neuropathic pain and induce a dose-dependent increase in the withdrawal threshold for allodynic (left side) limb, up to a maximum effect of 15 g. The efficacy of the compound in reducing neuropathic pain at different doses is determined by comparing response in the surgery-affected paw versus the response in the control paw. This is expressed as the MPE (maximum potential effect).

(vi) Determination of Analgesic Effect Against Neuropathic Pain-Bennett Model

Animals were prepared for testing, by use of a surgical procedure that induces neuropathic pain in one paw. IACUC guidelines for rodent survival surgery are followed. All surgical procedures are conducted on a clean, uncluttered surgical station. The area is wiped with a 70% ethanol solution before and after use. All instruments are sterilized by either autoclave or chemical sterilant (such as 2% glutaraldehyde >10 hr). Surgeons wear sterile gloves (for the initial procedure), clean lab coat or scrubs, hairnet or cap, and a half-mask respirator (when not working under a hood). Surgeons thoroughly wash their hands prior to donning sterile gloves. Gloves are disinfected in-between animals by cleansing with povidone iodine, chlorhexidine or 70% alcohol for at least 30 seconds. If multiple surgeries are performed, the instruments are cleaned and sterilized between procedures with hot glass beads (>10 seconds). To prevent thermal or chemical burns, the instruments are cooled by rinsing in sterile saline before use.

Male, Sprague Dawely rats, 175-200 g are used for surgeries. To minimize post-operative dehydration/maintain blood volume during the surgery, warmed sterile saline or Lactate Ringers solution at 10-15 mL/kg is administered subcutaneously immediately before or after surgery. This facilitates better renal function and presumably anesthesia product excretion post surgery. For all surgical procedures, anesthesia is induced with 4-5% isoflurane. Anesthesia is be maintained during surgery with 1-3% isoflurane. Following induction, the surgical site is carefully shaved and the exposed area is aseptically prepared with povidone-iodine scrub solution and 70% ethanol 2-3 times.

Chronic constriction injury (CCI), a model of neuropathic pain, is produced by following the method of Bennett and Xie (Bennett, G., et al. Pain, 1988, 33, 87-107). After site sterilization and anesthetic procedures outline above are completed, a 1.5 cm incision is made at the mid-thigh level to expose the biceps femoris and gluteous superficialis (right side), which are then separated by blunt dissection. The common sciatic nerve is exposed, isolated, and loosely ligated by four 5-0 chromic gut ligatures with <1 mm spacing between each. The surgical site is closed in layers—muscle is closed with 6.0 absorbable sutures, and the skin closed with wound clips Animals are allowed to recover on a warming plate and are returned to their home cages when fully ambulatory. Animals are not be used for testing until at least 10 days following surgery.

To measure mechanical sensitivity, tactile allodynia is measured using calibrated von Frey filaments (Stoelting, Wood Dale, Ill.) as described by Chaplan et al. (Chaplan S., et al. J of Neuroscience Methods 1994, 53, 55-63). Filament strengths used are: 0.4, 0.6, 1.0, 2, 4, 6, 8, and 15 g. Rats are be placed into inverted individual plastic containers (20× 12.5×20 cm) on top of a suspended wire mesh grid, and acclimated to the test chambers for at least 20 minutes. Filaments are applied perpendicular to the mid-plantar paw surface with enough force to cause slight buckling and held in place for 6-8 seconds. Positive responses include an abrupt withdrawal of the paw from the stimulus or flinching behavior immediately following removal of the stimulus. The maximum force applied will be 15 g. The 50% paw withdrawal threshold (PWT) is calculated in grams (g) using the up-down method of Dixon (Dixon W. Ann Rev Pharmacol Toxicol 1980, 20, 441-462). Only rats exhibiting increased mechanical sensitivity are used (threshold responses below 5 g). Data are reported as log g values and the percentage of maximum possible effect (% MPE) is calculated using log g values with the formula:

% MPE=(log[observed PWT in grams]−log[mean PWT vehicle])/(log[15]−log[mean PWT vehicle])*100

All statistical procedures are run on log g values.

(vii) Animal Pharmacokinetics

The pharmacokinetic properties of test compounds can be assessed in mouse, rat, dog and monkey to obtain various parameters including clearance (Clp), volume of distribution and bioavailability. For the determination of plasma and brain concentrations of the parent compound, naïve rats or mice can be dosed with the compounds i.p. and sacrificed at various time points post-dosing. For the determination of plasma concentrations, blood is collected into heparinized tubes and then centrifuged, and the separated plasma is frozen at −20° C. until analysis. For analysis, compounds are extracted from the samples via liquid-liquid extraction and quantified by liquid chromatography/mass spectroscopy.

d. Methods of Using the Compounds

In still yet another embodiment, the present invention provides a method for preventing or treating a disease condition in a subject in need of treatment thereof. The subject in need of treatment thereof can be a mammal, such as, but not limited to, a human.

In one aspect, the disease condition is a neurodegeneration disorder. A neurodegeneration disorder refers to a type of neurological disease marked by the loss of nerve cells in the brain or central nervous system. Examples of neurodegeneration disorders include, but are not limited to, Alzheimer's disease (AD), mild cognitive impairment (MCI), age-associated memory impairment (AAMI), multiple sclerosis, Parkinson's disease, vascular dementia, senile dementia, AIDS dementia, Pick's disease, dementia caused by cerebrovascular disorders, corticobasal degeneration, amyotrophic lateral sclerosis (ALS), Huntington's disease, diminished CNS function associated with traumatic brain injury or any combinations thereof.

In another aspect, the disease condition is a neuropsychiatric disorder. A neuropsychiatric disorder is a behavioral or psychological problem associated with a known neurological condition, and typically defined as a cluster of symptoms that co-exist. Examples of neuropsychiatric disorders include, but are not limited to, schizophrenia, cognitive deficits in schizophrenia, attention deficit disorder, attention deficit hyperactivity disorder, bipolar and manic disorders, depression or any combinations thereof.

In a further aspect, the present invention relates to methods of preventing or treating a pain including neuropathic and nociceptive pain, chronic or acute, such as, without limitation, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, ocular pain, visceral pain, cancer pain, dental pain, headache, migraine, carpal tunnel syndrome, fibromyalgia, neuritis, sciatica, pelvic hypersensitivity, pelvic pain, post operative pain, post stroke pain, and menstrual pain.

Cognitive deficits are recognized in various forms of neurodegeneration and neuropsychiatric disorders (such as, but not limited to, dementia, including Alzheimer's disease, (AD) and neuropsychiatric diseases, particularly schizophrenia and bipolar disorders). For example, in AD, current therapies offer modest efficacy, and therefore, there is need for an agent that offers a superior clinical benefit. One such agent, dimebolin, has been shown to inhibit neuronal death in models of neurodegenerative diseases suggestive of modification of disease processes (Lermontova, N. N.; Lukoyanov, N. V.; et al. Dimebon improves learning in animals with experimental Alzheimer's disease. *Bull. Exp. Biol. Med.* 2000, 129 (6), 544-546. Bachurin, S.; Bukatina, E.; et al. Antihistamine agent dimebon as a novel neuroprotector and a cognition enhancer. *Ann. N.Y. Acad. Sci.* 2001, 939 (Neuroprotective Agents), 425-435.) and more recently, shown to possess beneficial effect in cognition in patients with Alzheimer's disease (Burns, A.; Jacoby, R. Dimebon in Alzheimer's disease: old drug for new indication. *Lancet* 2008, 372 (9634), 179-80. Doody, R. S.; Gavrilova, S. I.; et al. Effect of dimebon on cognition, activities of daily living, behaviour, and global function in patients with mild-to-moderate Alzheimer's disease: a randomised, double-blind, placebo-controlled study. *Lancet* 2008, 372 (9634), 207-215.). Patients with mild-to-moderate Alzheimer's disease administered with 20 mg three times a day (60 mg/day) showed significant improvement in the clinical course of disease, as reflected in improvement over baseline for ADAS-Cog (Alzheimer's disease assessment scale—cognitive subscale) (Cummings, J.; Doody, R.; Gavrilova, S.; Sano, M.; Aisen, P.; Seely, L.; Hung, D. 18-month data from an open-label extension of a one-year controlled trial of dimebon in patients with mild-to-moderate Alzheimer's disease. Presented at the International Conference on Alzheimer's Disease (ICAD), Chicago, Ill., USA, July 2008; paper P4-334). Patients with mild-to-moderate Alzheimer's disease who had earlier received the drug for 12 months had preservation of function close to their starting baseline on key symptoms of Alzheimer's disease indicated the ability of dimebolin to alter disease progression. Patients originally on placebo who received dimebolin in the extension study showed stabilization across all key measures.

Beneficial effects of agents such as dimebolin have been linked to diverse mechanisms of action including effects at the level of mitochondria. In particular, dimebolin has been reported to improve neuronal function by enhancing neuronal outgrowth and affecting mitochondrial function. For example, Hung and coworkers (Hung, D. Dimebon: A phase 3 investigational agent for Alzheimer's disease with a novel mitochondrial mechanism of action. Presented at the International Conference on Alzheimer's Disease, Chicago, Ill., USA, July 2008; paper S4-04-05.) reported that dimebolin can protect cells from excitotoxic damage and improve neurite outgrowth in vitro model systems. Other mechanisms of action may also contribute to its beneficial effects of compounds with a "dimebolin-like" profile. Indeed, multi-targeted mechanisms have been proposed as viable approaches for treatment of diverse neurodegenerative diseases (Zhang, H.-Y. One-compound-multiple-targets strategy to combat Alzheimer's disease. *FEBS Lett.* 2005, 579, 5260-5264. Youdim, M.; Buccafusco, J. Multi-functional drugs for various CNS targets in the treatment of neurodegenerative disorders. *Trends in Pharm. Sci.* 2005, 26 (1), 27-35. Csermely, P.; Agoston, V.; Pongor, S. The efficiency of multi-target drugs: the network approach might help drug design. *Trends in Pharm. Sci.* 2005, 26 (4), 178-182. Cavalli, A.; Bolognesi, M. L.; Minarini, A.; Rosini, M.; Tumiatti, V.; Recanatini, M.; Melchiorre, C. Multi-target directed ligands to combat neurodegenerative diseases. *J. Med. Chem.* 2008, 51 (3), 347-372.). Dimebolin is also thought to exert its cognitive enhancing effects also through inhibition of butyryl-cholinesterase, acetyl cholinesterase, NMDA receptor or L-type calcium channels (Bachurin, S.; Bukatina, E.; et al. Antihistamine agent dimebon as a novel neuroprotector and a cognition enhancer. *Ann. N.Y. Acad. Sci.* 2001, 939 (Neuroprotective Agents), 425-435. Lermontova, N. N.; Redkozubov, A. E.; et al. Dimebon and tacrine inhibit neurotoxic action of beta-amyloid in culture and block L-type Ca(2+) channels. *Bull. Exp. Biol. Med.* 2001, 132 (5), 1079-83. Grigor'ev, V. V.; Dranyi, O. A.; et al. Comparative Study of Action Mechanisms of Dimebon and Memantine on AMPA- and NMDA-Subtypes Glutamate Receptors in Rat Cerebral Neurons.

*Bull. Exp. Biol. Med.* 2003, 136 (5): 474-477.). Interactions at the level of select 5HT receptors have also been implicated in the beneficial cognitive of dimebolin-like analogs (Tkachenko, S. Discovery and in vivo evaluation of potent 5-HT6 receptor antagonists for cognition enhancement in treating Alzheimer's disease. Presented at the International Conference on Alzheimer's Disease (ICAD), Chicago, Ill., USA, July 2008; paper P2-478.). Thus, available preclinical and clinical data suggests that compounds exhibiting a "dimebolin-like" profile can be beneficial in treating neurodegenerative diseases such as Alzheimer's disease and other dementias. Therefore, it is believed that the compounds of the present invention exhibit at least one of the mechanisms of action exhibited by dimebolin.

For treating a neurodegenerative or a neuropsychiatric disorder, the method comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug. A "cognitive enhancing drug", as defined herein, is a drug that improves impaired human cognitive abilities of the brain (namely, thinking, learning, and memory). Cognitive enhancing drugs work by altering the availability of neurochemicals (e.g., neurotransmitters, enzymes, and hormones), by improving oxygen supply, by stimulating nerve growth, or by inhibiting nerve damage. Examples of cognitive enhancing drugs include a compound that increases the activity of acetylcholine such as, but not limited to, an acetylcholine receptor agonist (e.g., a nicotinic alpha-7 receptor agonist or allosteric modulator, an alpha4 beta2 nicotinic receptor agonist or allosteric modulators), an acetylcholinesterase inhibitor (e.g., donepezil, rivastigmine, and galantamine), a butyrylcholinesterase inhibitor, an N-methyl-D-aspartate (NMDA) receptor antagonist (e.g., memantine), an activity-dependent neuroprotective protein (ADNP) agonist, a serotonin 5-HT1A receptor agonist (e.g., xaliproden), a 5-HT$_4$ receptor agonist, a 5-HT$_6$ receptor antagonist, a serotonin 1A receptor antagonist, a histamine H$_3$ receptor antagonist, a calpain inhibitor, a vascular endothelial growth factor (VEGF) protein or agonist, a trophic growth factor, an anti-apoptotic compound, an AMPA-type glutamate receptor activator, a L-type or N-type calcium channel blocker or modulator, a potassium channel blocker, a hypoxia inducible factor (HIF) activator, a HIF prolyl 4-hydroxylase inhibitor, an anti-inflammatory agent, an inhibitor of amyloid Aβ peptide or amyloid plaque, an inhibitor of tau hyperphosphorylation, a phosphodiesterase 5 inhibitor (e.g., tadalafil, sildenafil), a phosphodiesterase 4 inhibitor, a monoamine oxidase inhibitor, or pharmaceutically acceptable salt thereof. Specific examples of such cognitive enhancing drugs include, but are not limited to, cholinesterase inhibitors such as donepezil (Aricept®), rivastigmine (Exelon®), galanthamine (Reminyl), N-methyl-D-aspartate antagonists such as memantine (Namenda®). At least one cognitive enhancing drug can be administered simultaneously with the compounds of the present invention or sequentially with the compounds of the present invention (and in any order). Additionally, it is believed that the combinations described herein may have additive or synergistic effects when used in the above-described treatment.

In still yet another embodiment, the present invention relates to a method for preventing (the development of) a disease condition, such as a neurodegeneration disorder or a neuropsychiatric disorder. As used herein, the term "prevent" a disease condition, such as a neurodegenerative disorder or a neuropsychiatric disorder by administration of any of the compounds described herein means that the detectable physical characteristics or symptoms of the disease or condition do not develop following the administration of the compound described herein. Specifically, the method of the present invention comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug.

In still yet another embodiment, the present invention relates to a method for preventing the progression (e.g., worsening) of a disease condition, such as a neurodegeneration disorder or a neuropsychiatric disorder. The method comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug.

In the above described methods for preventing the development or progression of a neurodegeneration disorder or a neuropsychiatric disorder one or more biomarkers, diagnostic tests or combination of biomarkers and diagnostic tests known to those skilled the art can be used to determine whether or not (1) a subject is at risk of developing one or more of neurodegeneration disorders or neuropsychiatric disorders; or (2) the neurodegeneration disorders or neuropsychiatric disorders in the subject previously diagnosed with one or more of the aforementioned disorders is progressing (e.g., worsening).

One or more biomarkers, diagnostic tests or combinations of biomarkers and diagnostic tests known in the art can be used to identify subjects who are at risk of developing a neurodegeneration disorder or a neuropsychiatric disorder. Likewise, one or more biomarkers, diagnostic tests or combinations of biomarkers and diagnostic tests known in the art can be used to determine the progression of the disease or condition of subjects who have been identified as suffering from a neurodegeneration disorder or a neuropsychiatric disorder. For example, one or more biological markers, neuroimaging markers or combination of biological or neuroimaging markers (e.g., MRI, etc.) can be used to identify subjects at risk of developing AD or, for those subjects identified as suffering AD, the progression of the disease. Biological markers that can be examined include, but are not limited to, beta-amyloid$_{1-42}$, tau, phosphorylated tau (ptau), plasma Aβ antibodies, α-antichymotrypsin, amyloid precursor protein, APP isoform ratio in platelets, β-secretase (also known as BACE), CD59, 8-hydroxy-deoxyguanine, glutamine synthetase, glial fibrillary acidic protein (GFAP), antibodies to GFAP, interleukin-6-receptor complex, kallikrein, melanotransferrin, neurofilament proteins, nitrotyrosine, oxysterols, sulphatides, synaptic markers, 51003, NPS, plasma signaling proteins, etc., or any combinations thereof (See, Shaw, L., et al., *Nature Reviews* 2007, 6, 295-303. Borroni, B., et al., *Current Medicinal Chemistry* 2007, 14, 1171-1178.

Phillips, K., et al., *Nature Reviews* 2006, 5 463-469. Bouwman, F. H., et al., *Neurology* 2007, 69, 1006-1011; Ray, S., et al., *Nature Medicine* 2007, 13 (11), 1359-1362. Cummings, J., et al., *Neurology* 2007, 69, 1622-1634.).

Actual dosage levels of active ingredients in the pharmaceutical compositions of the present invention can be varied so as to obtain an amount of the active compound(s) that is effective to achieve the desired therapeutic response for a particular subject (e.g., a mammal, preferably, a human (patient)), compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the present invention can also be administered to a subject as a pharmaceutical composition comprising the compounds of interest in combination with at least one pharmaceutically acceptable carriers. The phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a subject (namely, a mammal, such as a human) ranges from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions may contain such amounts or submultiples thereof to make up the daily dose.

e. Pharmaceutical Compositions

In yet another embodiment, the present invention provides pharmaceutical compositions. The pharmaceutical compositions of the present invention comprise the compounds of the present invention or a pharmaceutically acceptable salt or solvate thereof. The pharmaceutical compositions of the present invention comprise compounds of the present invention that can be formulated together with at least one non-toxic pharmaceutically acceptable carrier.

In yet another embodiment, the present invention provides a pharmaceutical composition comprising compounds of the present invention, or a pharmaceutically acceptable salt thereof, and one or more pharmaceutically acceptable carriers, alone or in combination with one or more compounds that are not the compounds of the present invention. Examples of one or more compounds that can be combined with the compounds of the present invention in pharmaceutical compositions, include, but are not limited to, one or more cognitive enhancing drugs.

The pharmaceutical compositions of this present invention can be administered to a subject (e.g., a mammal, such as a human) orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of the present invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of the present invention include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq.). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

Esters can be prepared from substrates of formula (I), formula (II), formula (III), or formula (IV) containing either a hydroxyl group or a carboxy group by general methods known to persons skilled in the art. The typical reactions of these compounds are substitutions replacing one of the heteroatoms by another atom, for example:

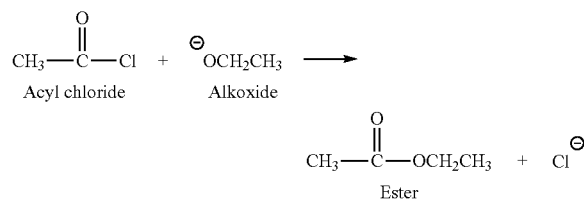

Amides can be prepared from substrates of formula (I), formula (II), formula (III), or formula (IV) containing either an amino group or a carboxy group in similar fashion. Esters can also react with amines or ammonia to form amides.

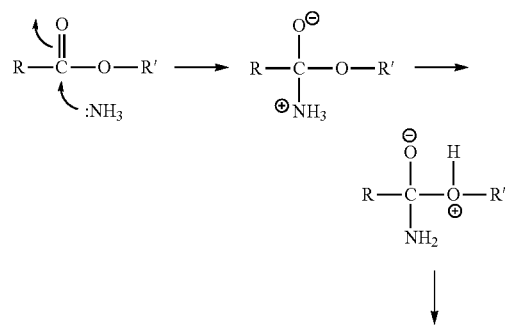

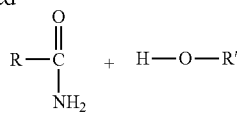

Another way to make amides from compounds of formula (I), formula (II), formula (III), or formula (IV) is to heat carboxylic acids and amines together.

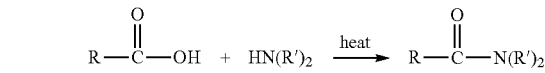

The present invention also contemplates compounds of the present invention formed by synthetic means or formed by in vivo biotransformation of a prodrug.

The compounds of the present invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. Screening Methods

Methods for identifying one or more target compounds that can be used to prevent or treat a neurodegenerative disorder or a neuropsychiatric disorder in a subject in need of treatment thereof. Preferably, the methods allow for the identification of one or more target compounds in a high throughput manner.

The method involves providing a population of neuronal or neuroblastoma cells or neuronal or neuroblastoma cell lines. Examples of neuronal or neuroblastoma cells or cell lines that can be used in this method include, but are not limited to, PC 12, SH-SY5Y, SK-N-SH, IMR-32, or dissociated cells from tissues such as neonatal rat cortex or hippocampus cells. One or more target compounds are added to the population of neuronal or neuroblastoma cells or cell lines. If more then one target compound is being added, the target compounds can all be the same compounds but added in varying concentrations (such as, for example, 0.1 nM to 30 micromolar). Alternatively, the target compounds can all be different compounds. After addition of one or more target compounds to the population of cells or cell lines described above, the cells or cell lines are allowed to incubate for a period from at least one 1 hour to about 72 hours, preferably about 24 hours. The neuronal number and neurite outgrowth can then be determined using routine techniques known in the art. For example, the cells or cell lines can be fixed and then stained using any stain known in the art, such as, for example, β-tubulin (green). The total cell number and the extent of neurite outgrowth can be determined using the Neurite Outgrowth module in the MetaMorph Imaging software (Commercially available from Molecular Devices, Sunnyvale, Calif.). Target compounds that cause an increase in neuronal number and/or neuronal outgrowth are selected for further testing for use in preventing or treating a neurodegenerative or neuropsychiatric disorders.

Method details are described above in the Biological Data section in the description of the Effects on Mitochondrial Function assay.

One advantage of the assay is that after a 16-18 hours stress of serum deprivation, the health of the mitochondria can be measure by a 30 minute step with a fluorescent dye, JC-1. JC-1 measures the change in mitochondria membrane potential by measuring red fluorescence with excitation/emission at 560/595 nM, which is high for healthy cells and green fluorescence with excitation/emission at 495/535 nM), which is low if cells are unhealthy.

Another advantage of the assay is that the assay can measure the effect of mitochondrial function of multiple compounds in either a 1 point concentration or a 9-point dose response curve in a 96-well based format.

g. General Synthesis

This invention is intended to encompass compounds of the present invention whether prepared by synthetic processes or by metabolic processes. Preparation of the compounds by metabolic processes includes those occurring in the human or animal body (in vivo) or processes occurring in vitro.

The compounds of the present invention may be prepared by a variety of processes well known for the preparation of compounds of this class. For example, the compounds of the present invention wherein the groups a, $R^2$, $R^3$, L, Q, X, h, k, m, and n, have the meanings as set forth in the Summary of the Invention section unless otherwise noted, can be synthesized as shown in Schemes 1-13.

Abbreviations which have been used in the descriptions of the Schemes and the Examples that follow are: Ac for acetyl; aq for aqueous; atm for atmosphere; Bn for benzyl; Bu for butyl; DMF for N,N-dimethylformamide; DMSO for dimethyl sulfoxide; Et for ethyl; EtOH for ethanol; HOAc for acetic acid; HPLC for high pressure liquid chromatography; LC/MS for liquid chromatography/mass spectroscopy; Me for methyl; MeOH for methanol; NBS for N-bromosuccinimide; NCS for N-chlorosuccinimide; OAc for acetate; Ph for phenyl; psi for pounds per square inch; t-Bu for tertiary-butyl; TFA for trifluoroacetic acid; and THF for tetrahydrofuran.

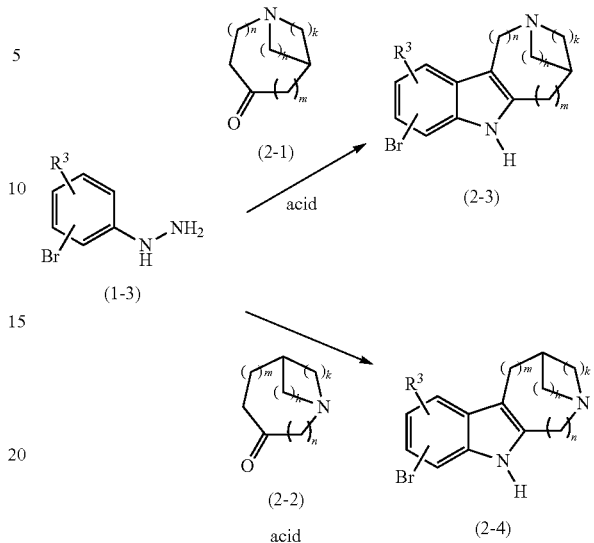

Condensation of compounds of formula (1-3) with bicyclic ketoamines of formula (2-1) under conditions of the Fischer indole synthesis as described in, for example (Hughes, D. L. Progress in the Fischer Indole Reaction. A Review. *Org. Prep. Proced. Int.* 1993, 25, 607-632. Humphrey, G. R.; Kuethe, J. K. Practical Methodologies for the Synthesis of Indoles.

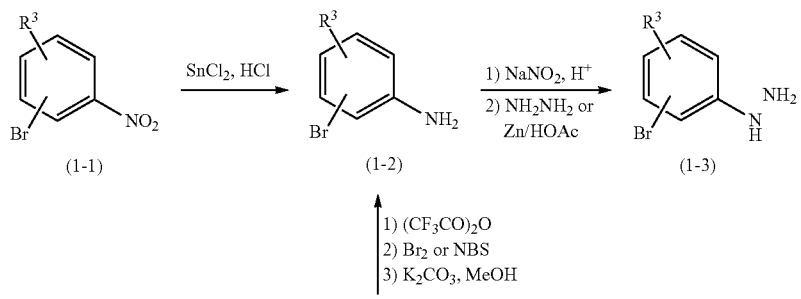

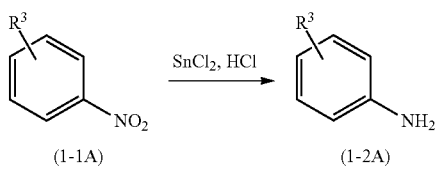

Compounds of formula (1-3), wherein $R^3$ is defined in the Summary of the Invention, can be prepared from the corresponding nitrobenzenes of formula (1-1) or anilines of formula (1-2) by diazotization followed by displacement with hydrazine, or reduction of the diazonium to provide the hydrazine of formula (1-3). Alternatively, the compounds can be prepared from des-bromo precursors by electrophilic bromination of the protected anilines of formula (1-2A).

*Chem. Rev.* 2006, 106, 2875-2911.), provides compounds of formula (2-3). Compounds of formula (2-3) are representative of compounds of formula (I). In like manner, condensation of compounds of formula (1-3) with bicyclic ketoamines of formula (2-2) under conditions of the Fischer indole synthesis gives compounds of formula (2-4). Compounds of formulas (2-4) are representative of compounds of formula (II).

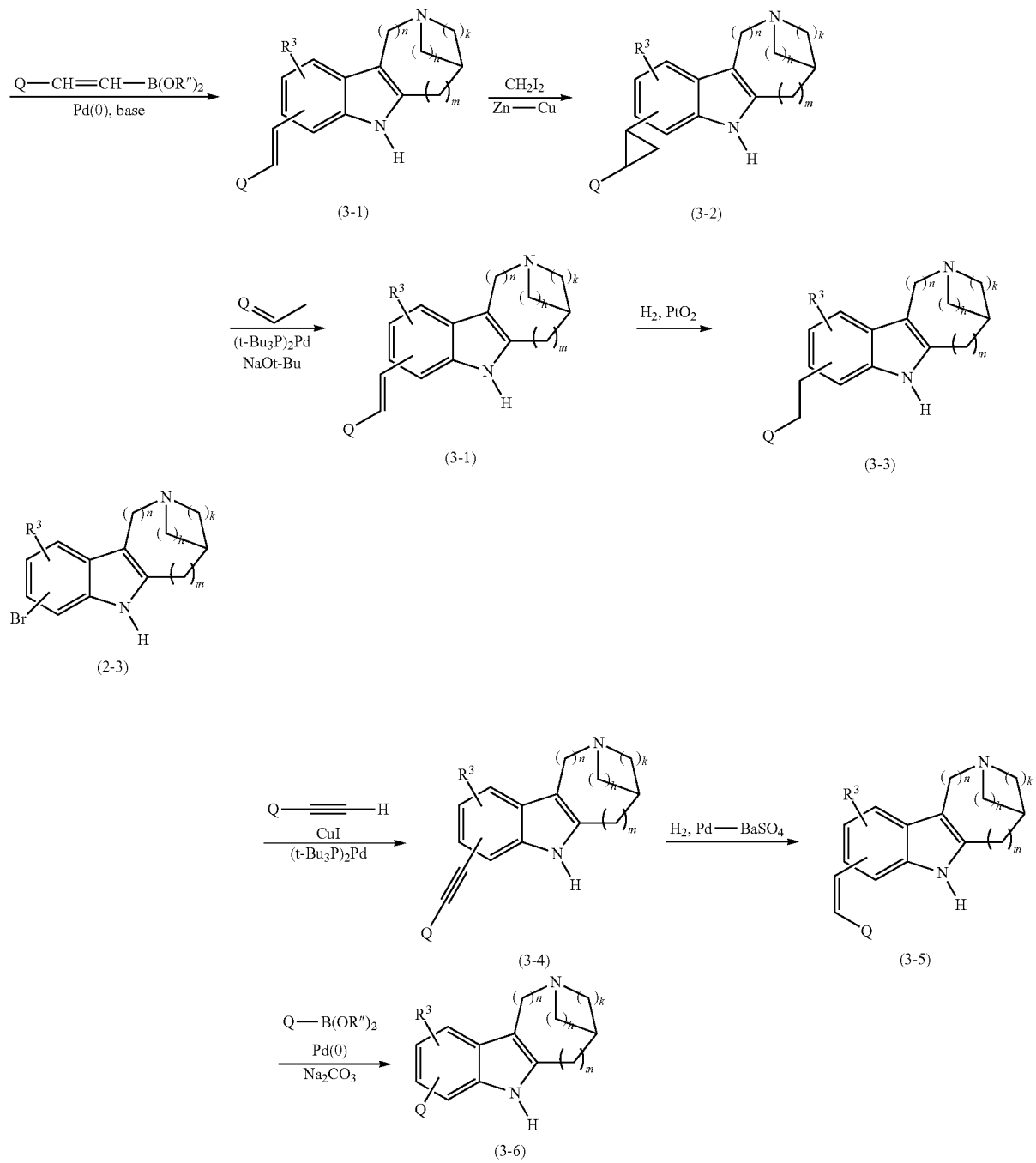

Compounds of formula (2-3) can be elaborated by any of the methods of Scheme 3 to install the substituent X-L-Q as defined in formula (I) to give compounds of formulas (3-1), (3-4), and (3-6). Compounds of formula (2-3) can be treated under Suzuki reaction conditions with Q-CH=CH—B(OR")$_2$ or Q-B(OR")$_2$, wherein R" is hydrogen, alkyl or taken to together with the boron and oxygen atoms form a 4,4,5,5-tetramethyl-1,3,2-dioxaborolane, to give compounds of formula (3-1) or (3-6), respectively. Heck reaction conditions can be used to also convert compounds of formula (2-3) to compounds of formula (3-1). Similarly, Sonogashira coupling conditions can be used to convert compounds of formula (2-3) to compounds of formula (3-4). Further manipulation of the side chain, by methods well-known to one skilled in the art, can be employed to provide the variations embodied in the definition of L in formula (I). For example, carbene addition to compounds of formula (3-1) can give compounds of formula (3-2). Compounds of formula (3-1) and (3-4) can be reduced with hydrogen and an appropriate catalyst to give compounds of formula (3-3) and (3-5), respectively. Compounds of formulas (3-1), (3-2), (3-3), (3-4), (3-5), and (3-6) are representative of compounds of formula (I).

Scheme 4
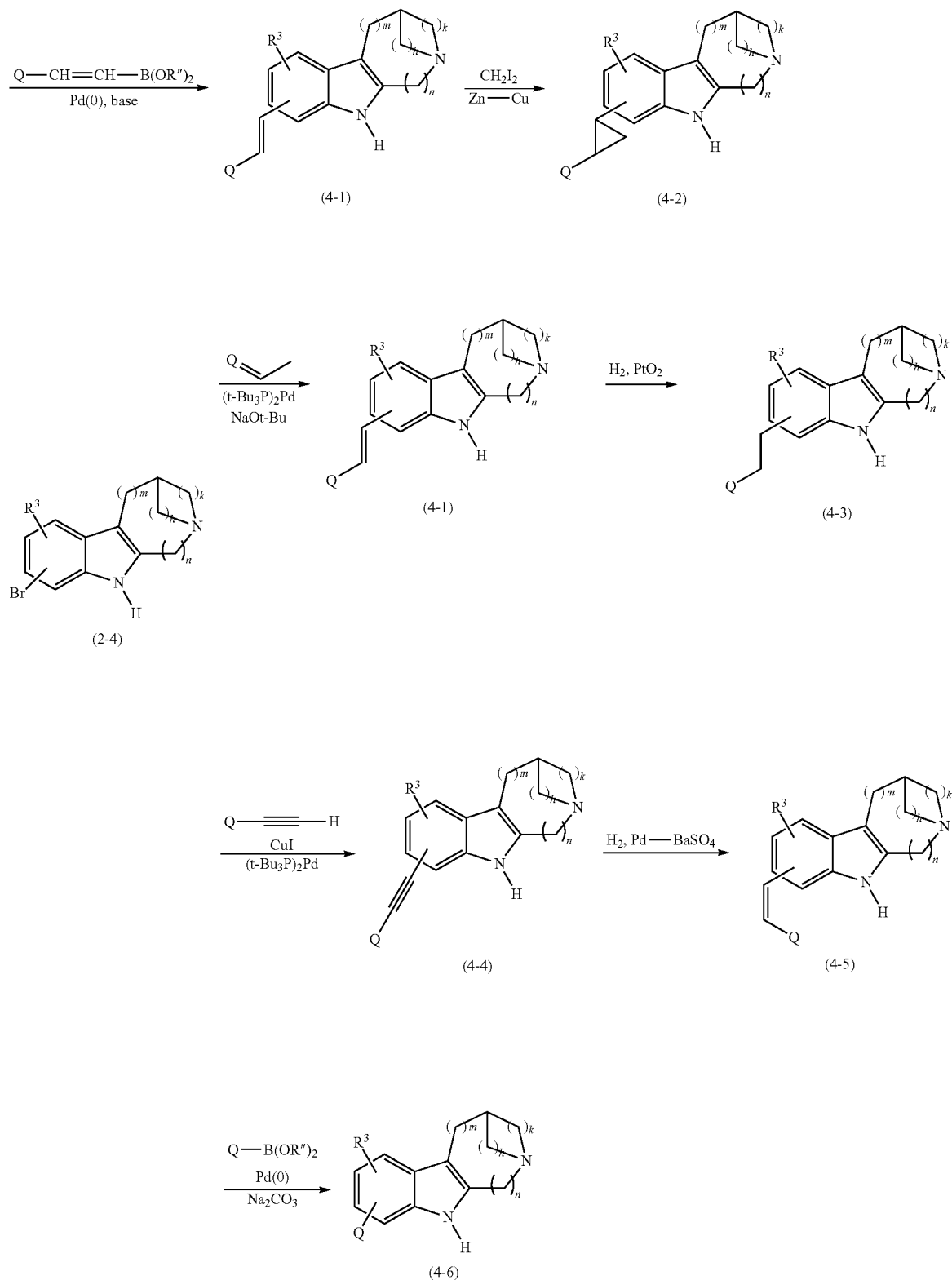
Compounds of formula (2-4) can be elaborated with the reaction sequences described in Scheme 3 to furnish compounds of formulas (4-1), (4-2), (4-3), (4-4), (4-5), and (4-6). Compounds of formulas (4-1), (4-2), (4-3), (4-4), (4-5), and (4-6) are representative of compounds of formula (II).

Scheme 5

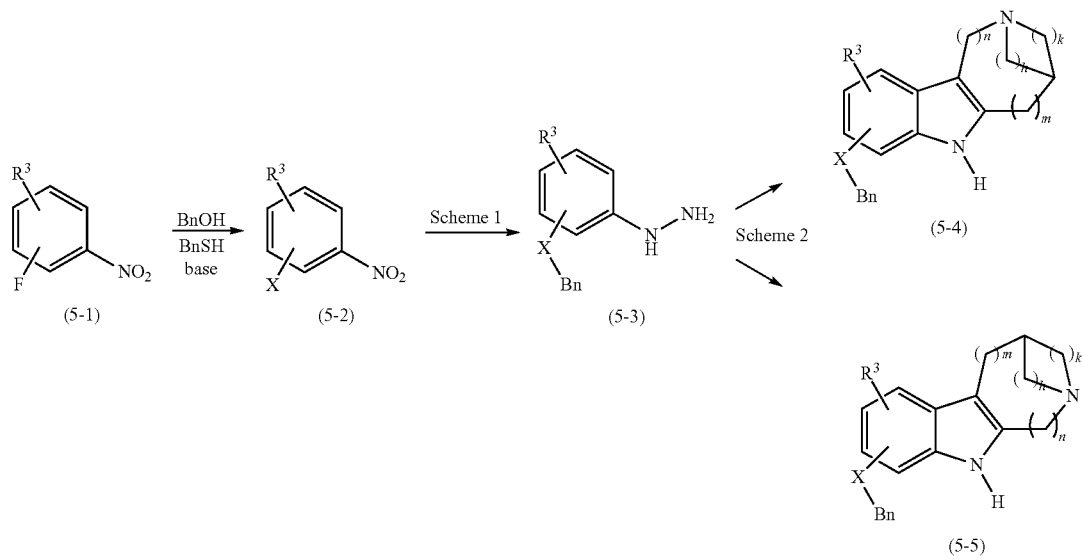

Compounds of formula (5-4) can be prepared as illustrated in Scheme 4. Accordingly, compounds of formula (5-1) can be reacted with benzyl alcohol or benzyl mercaptan under nucleophilic aromatic substitution reaction conditions to give compounds of formula (5-2), wherein X is O or S. Compounds of formula (5-2) can be converted to hydrazines of formula (5-3) using the conditions described in Scheme 1. Compounds of formula (5-3) can be reacted under Fischer indole conditions with compounds of formula (2-1) as described in Scheme 2 to give compounds of formula (5-4) which are representative of compounds of formula (I). Similarly, compounds of formula (5-3) can be reacted with compounds of formula (2-2) as described in Scheme 2 to give compounds of formula (5-5) which are representative of compounds of formula (II).

Scheme 6

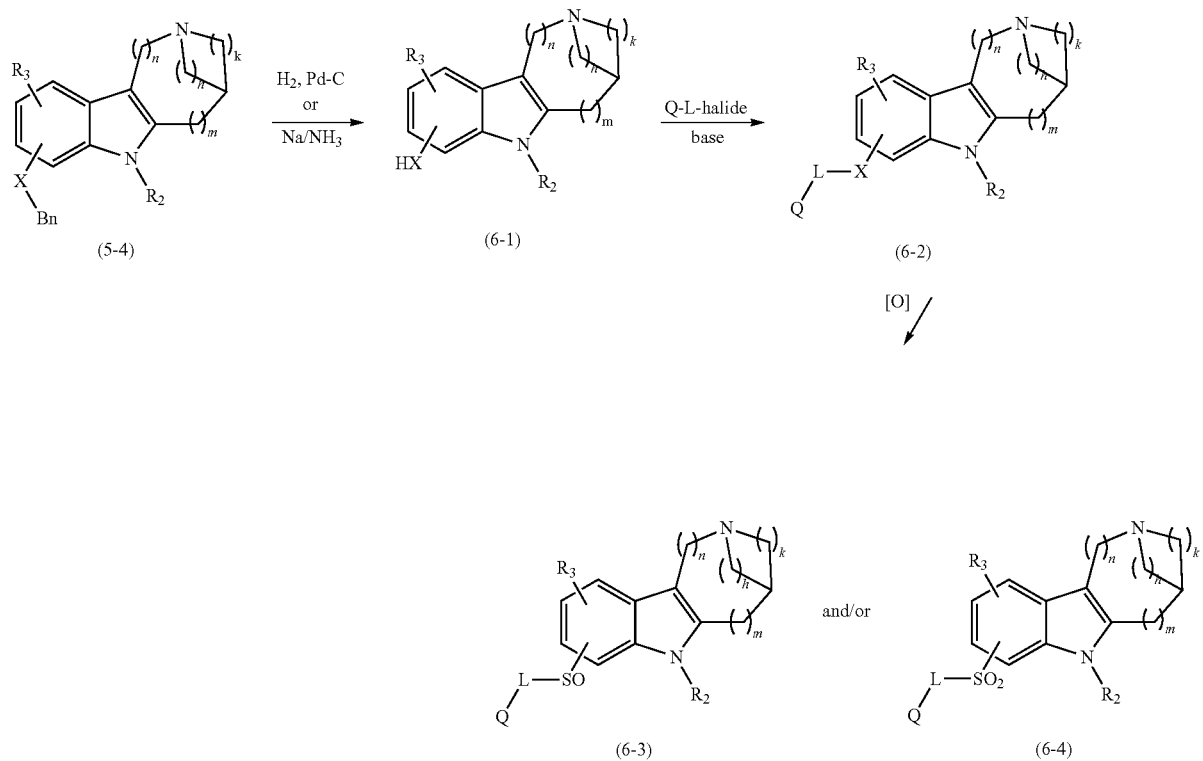

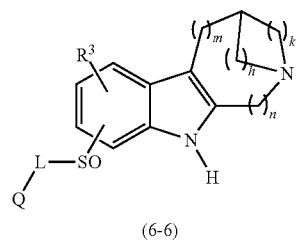

(6-6)

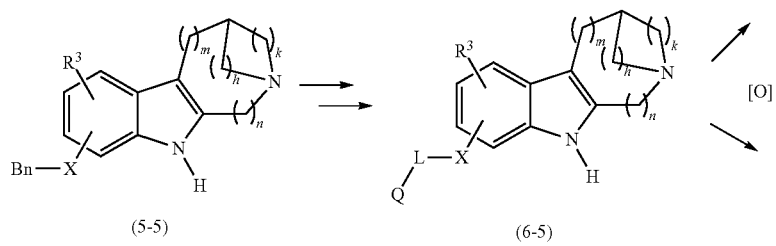

(5-5)   (6-5)   [O]

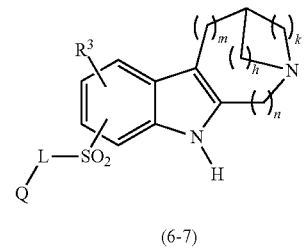

(6-7)

The benzyloxy or thiobenzyl group of compounds of formula (5-4), wherein X is O or S, can be cleaved reductively (e.g., Piers et al. Can. J. Chem. 1962, 40, 511-517) to give the corresponding phenols or thiophenols of formula (6-1). The liberated phenols or thiophenols of formula (6-1) can be alkylated to provide compounds of formula (6-2). In the case where X is S, compounds of formula (6-2) can be oxidized to the sulfoxides of formula (6-3) or sulfones of formula (6-4). Compounds of formulas (6-2), (6-3), and (6-4) are representative of compounds of formula (I).

The benzyloxy or thiobenzyl group of compounds of formula (5-5), wherein X is O or S, can be cleaved reductively and alkylated as described above to provide compounds of formula (6-5). In the case where X is S, compounds of formula (6-5) can be oxidized to the sulfoxides of formula (6-6) or sulfones of formula (6-7). Compounds of formulas (6-5), (6-6), and (6-7) are representative of compounds of formula (II).

Scheme 7

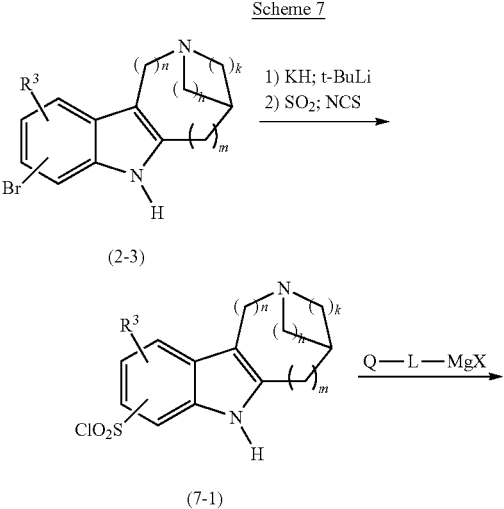

(2-3)   1) KH; t-BuLi
         2) SO$_2$; NCS (7-1)   Q—L—MgX

-continued

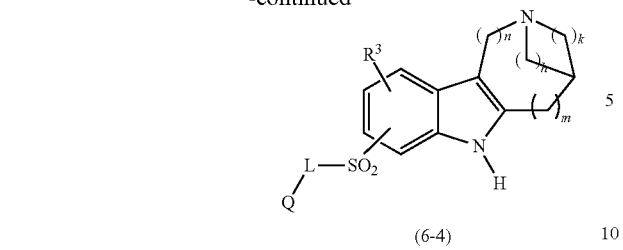

(6-4)

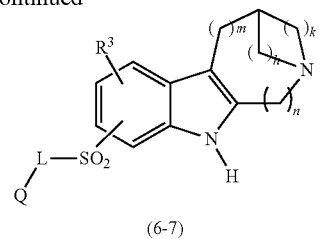

(6-7)

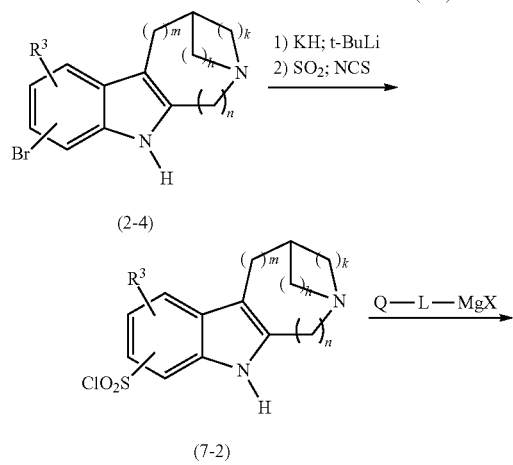

Alternatively, the sulfones of formula (6-4) can be prepared as described in Scheme 7. Compounds of formula (2-3) can be metalated and then reacted with sulfur dioxide and N-chlorosuccinimide as described by (Madar, M M et al, Bioorganic and Medicinal Chemistry Letters 2005, 15,617-620) to give chlorosulfones of formula (7-1). Reaction with a suitable organometallic agent such as Grignard reagent Q-L-MgBr provides compounds of formula (6-4). Compounds of formula (6-4) are representative of compounds of formula (I).

Compounds of formula (2-4) can be transformed in like manner to compounds of formula (7-2) and then to compounds of formula (6-7). Compounds of formula (6-7) are representative of compounds of formula (II).

Scheme 8

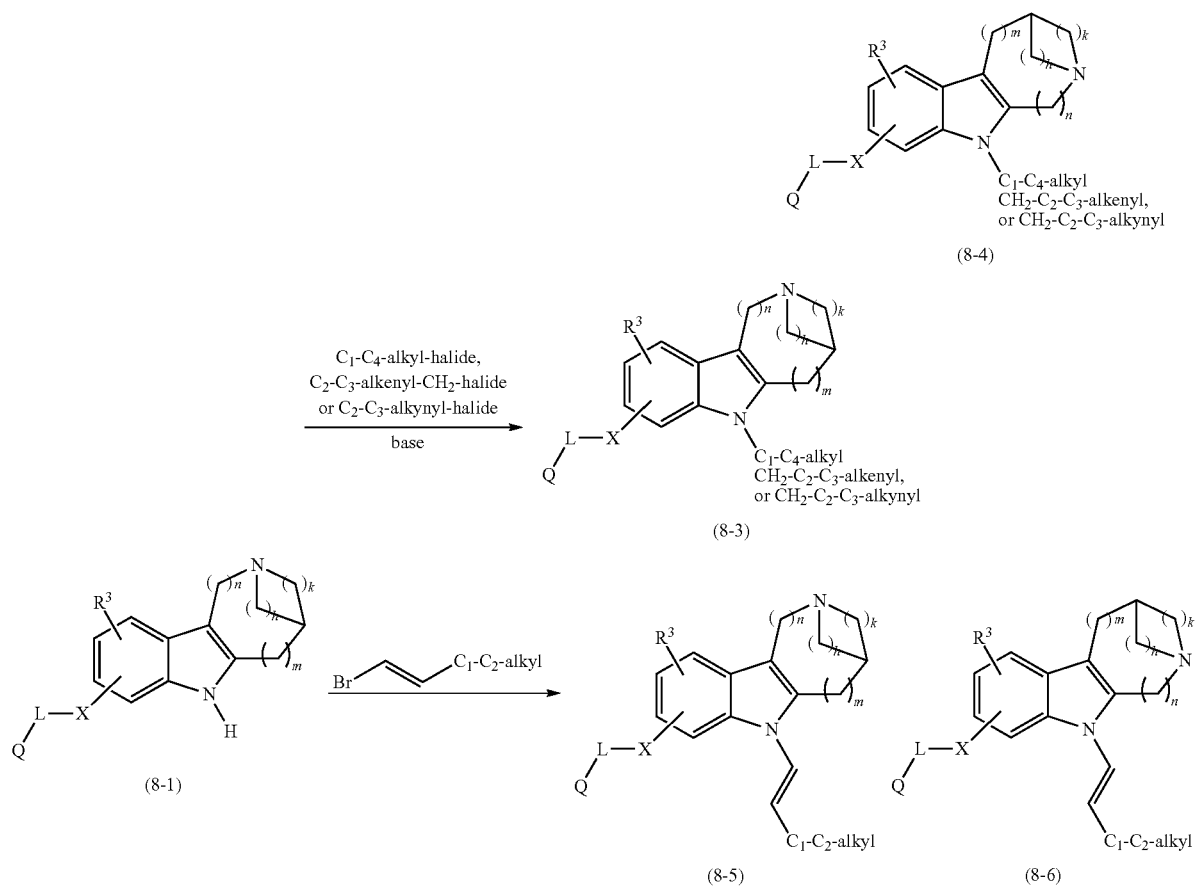

-continued

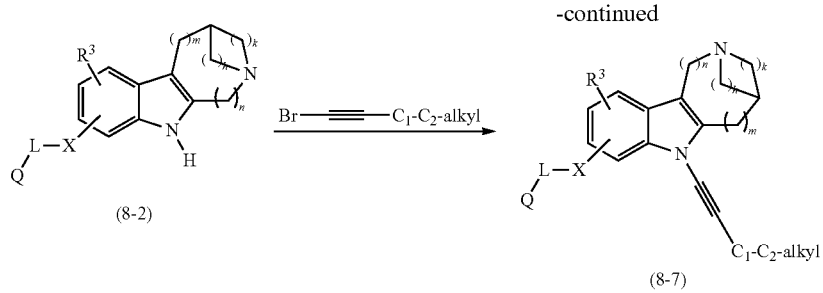

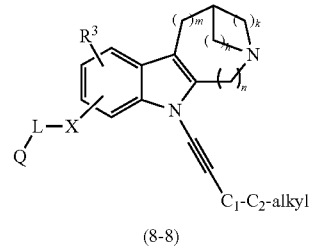

The indole NH of compound of formula (8-1); wherein $R^3$, L, Q, X, h, k, m, and n are as defined in the Summary of the Invention; can be elaborated to compounds of formulas (8-3), (8-5), or (8-7) as illustrated in Scheme 8. Compounds of formula (8-1) can be alkylated with a $C_1$-$C_4$-alkyl-halide, optionally in the presence of a base (e.g., NaH or $NaNH_2$), in a solvent such as N,N-dimethylformamide or tetrahydrofuran to give compounds of formula (8-3). Alkylations can also be accomplished with halo-alkenes or halo-alkynes wherein the double or triple bond is separated from the halogen by at least one methylene to provide compounds of formula (8-3). N-Vinylation (Lebedov, A Y et al. Organic Letters 2002, 4, 623-626) and N-alkynylation (Zhang Y et al. Organic Letters 2004, 6, 1151-1154) can be accomplished by Pd- and Cu-mediated processes to give compounds of formulas (8-5) and (8-7), respectively. Compounds of formulas (8-3), (8-5), and (8-7) are representative of compounds of formula (I).

Similarly, compounds of formula (8-2) can be converted to compounds of formulas (8-4), (8-6), and (8-8) which are representative of compounds of formula (II).

Scheme 9

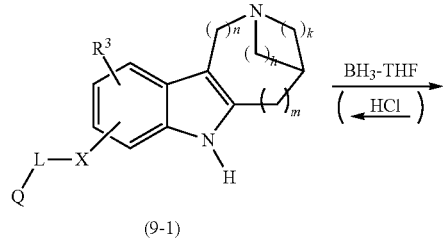

(9-1)

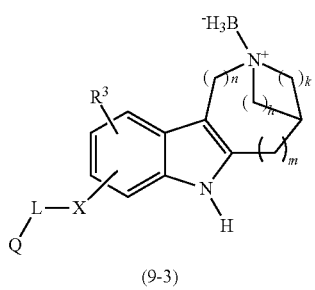

(9-3)

-continued (9-2)

(9-4)

For many of the conversions described herein, it may be preferable to mask the bridgehead amine with a suitable protecting group that can be removed later in the synthesis. Two such protecting strategies are outlined in Scheme 9. Treatment of the amine [illustrated for compounds of formula (9-1), but applicable also to compounds of formula (9-2)] with one equivalent of borane-tetrahydrofuran provides the borane-amine complexes of formula (9-3), in which the nucleophilicity and basicity of the bridgehead amine is substantially attenuated allowing selective reaction of electrophiles at other sites of the molecule. Compounds of formula (9-3) are representative of compounds of formula (III). Similarly, borane complexes made from compounds of formula (9-2) are representative of compounds of formula (IV). The borane complex can be removed when desired by treatment with HCl. In a similar fashion, treatment of the bridgehead amine with a benzyl halide [illustrated for compounds of formula (9-2), but equally applicable to compounds of formula (9-1)] results in formation of the bridgehead quaternary ammonium species of formula (9-4). The benzyl group can be removed when desired by hydrogenolysis.

Scheme 10

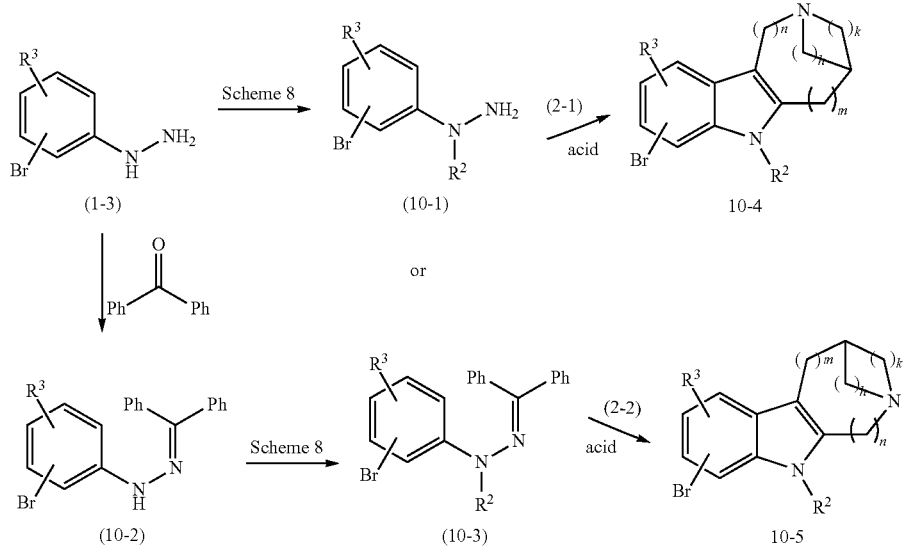

In some cases, it may be convenient to install $R^2$, wherein $R^2$ is $C_1$-$C_4$ alkyl, $C_2$-$C_4$ alkenyl, or $C_2$-$C_4$ alkynyl, at the hydrazone stage as illustrated in Scheme 8. For those compounds wherein $R^2$ is $C_2$-$C_4$ alkenyl or $C_2$-$C_4$ alkynyl, the double or triple bond of the $R^2$ substituent is separated from the nitrogen to which it is attached by at least one methylene when alkylation chemistry is used. The hydrazines of formula (1-3) can be converted to the corresponding hydrazones of formula (10-2) by reaction with benzophenone under conditions known to one skilled in the art. Compounds of formulas (1-3) or (10-2) can be alkylated as described in Scheme 8 for the preparation of compounds of formula (8-3) or (8-4) to give compounds of formulas (10-1) and (10-3), respectively. Compounds of formulas (10-1) and (10-3) can be reacted under Fischer indole reaction conditions with keto-amines of formulas (2-1) or (2-2) to provide compounds of formula (10-4) or (10-5), respectively. Compounds of formula (10-4) are representative of compounds of formula (I), and compounds of formula (10-5) are representative of compounds of formula (II).

Scheme 11

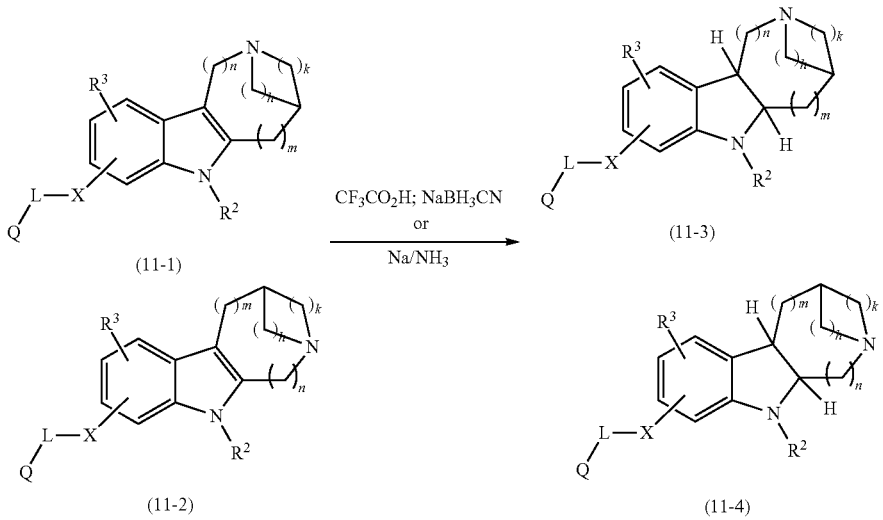

Reduction of the indoles of formula (11-1); wherein $R^2$, $R^3$, L, Q, X, h, k, m and n are as defined in the Summary of the invention; to the corresponding indolines of formula (11-3) can be accomplished by established methods as illustrated in Scheme 11. Accordingly, the indoles of formula (11-1) can be reduced to the indolines of formula (11-3) in the presence of sodium cyanoborohydride and trifluoroacetic acid or in the presence of sodium and ammonia. Compounds of formula (11-3) are representative of compounds of formula (I).

Similarly, compounds of formula (11-2) can be reduced to compounds of formula (11-4). Compounds of formula (11-4) are representative of compounds of formula (II).

Scheme 12

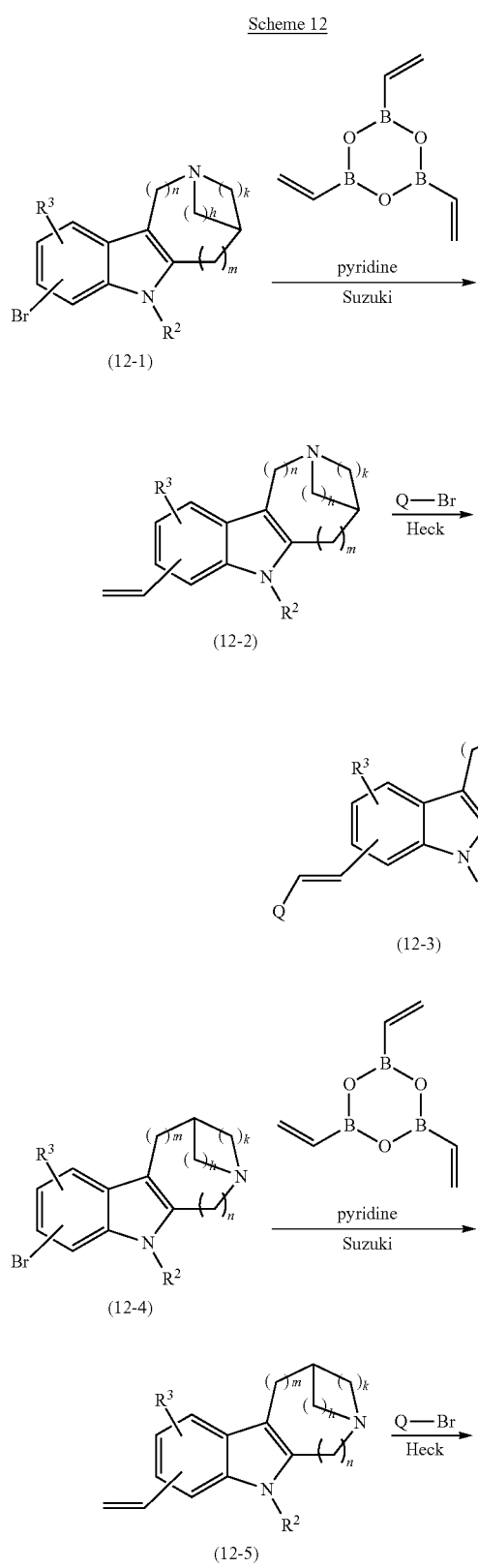

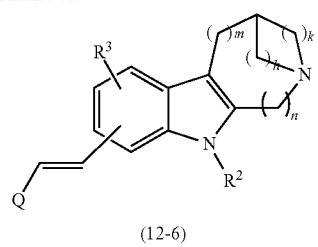

Compounds of formula (12-3) can be prepared as described in Scheme 12. Compounds of formula (12-1); wherein $R^2$, $R^3$, h, k, m, and n are as defined in the Summary of the Invention; can be reacted under Suzuki reaction conditions with 2,4,6-trivinyl-1,3,5,2,4,6-trioxatriboranane pyridine complex to give compounds of formula (12-2). Compounds of formula (12-2) can then be reacted with Q-Br, wherein Q is as described in the Summary of the Invention, under Heck reaction conditions to give compounds of formula (12-3). Compounds of formula (12-3) are representative of compounds of formula (I).

In like manner, compounds of formula (12-4) can be converted to compounds of formula (12-5). Then compounds of formula (12-5) can be coupled with Q-Br to give compounds of formula (12-6). Compounds of formula (12-6) are representative of compounds of formula (II).

Scheme 13

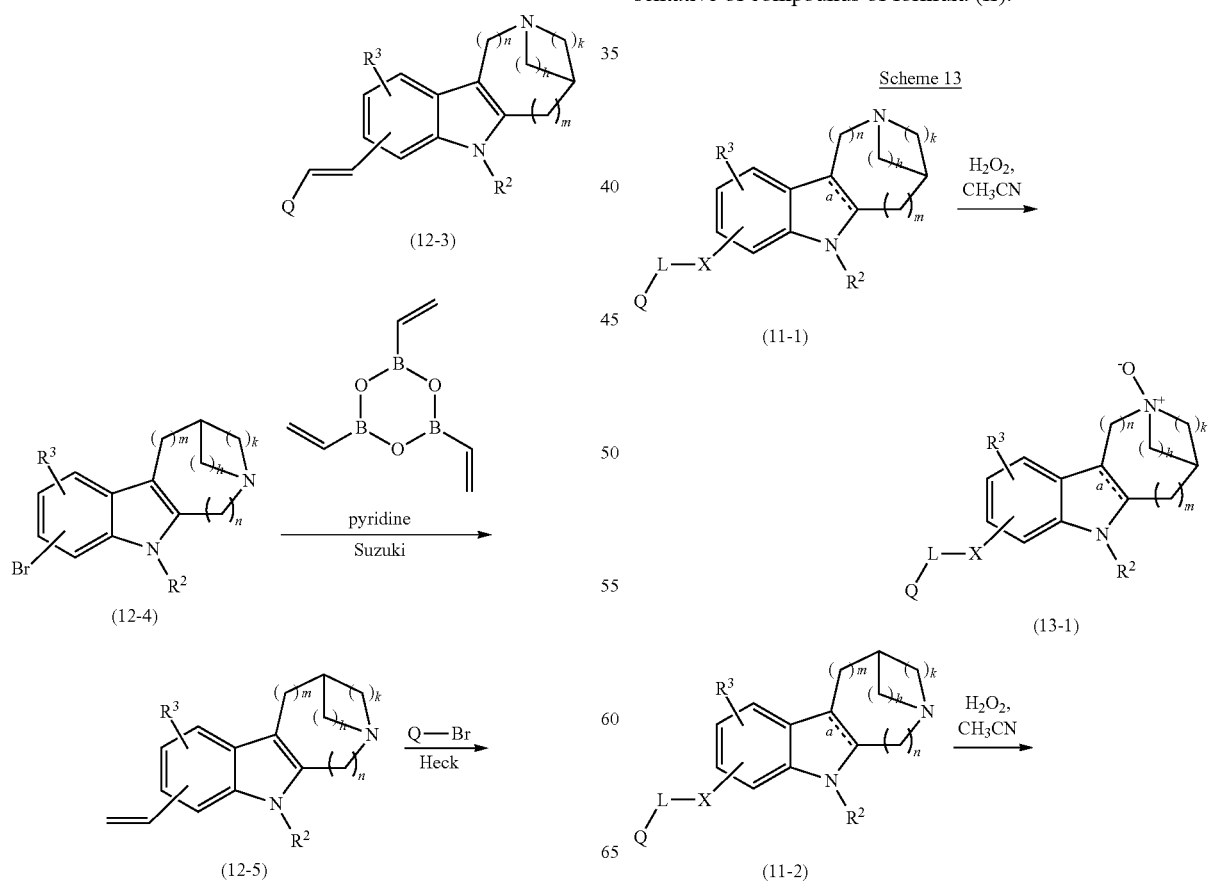

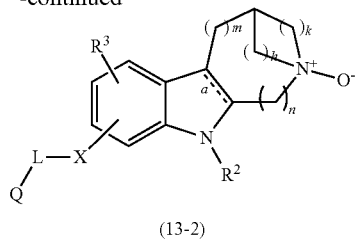

(13-2)

The amines of formula (11-1) and (11-2); wherein a, $R^2$, $R^3$, h, k, m, and n are as defined in the Summary of the Invention; can be oxidized by, for example, hydrogen peroxide in acetonitrile, to the N-oxides of formulas (13-1) and (13-2), respectively, as illustrated in Scheme 12. Compounds of formula (13-1) are representative of compounds of formula (III) and compounds of formula (13-2) are representative of compounds of formula (IV).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protective Groups in Organic Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

H. EXAMPLES

The compounds and processes of the present invention will be better understood by reference to the following Examples, which are intended as an illustration of and not a limitation upon the scope of the application.

Example 1

7-[(E)-2-(6-methylpyridin-3-yl)vinyl]-3,4,5,6-tetrahydro-1H-2,5-ethanoazepino[4,3-b]indole

Example 1A 1-azabicyclo[3.2.2]nonan-4-one

An ice-cooled solution (5° C.) of (trimethylsilyl)diazomethane/hexane (2 N, 30 mL, 60 mmol; Aldrich) under nitrogen was treated dropwise with a solution of quinuclidin-3-one (7500 mg, 60 mmol) in dry tetrahydrofuran (40 mL). Methanol (20 mL) was added, and the yellow solution was warmed to room temperature, stirred for 24 hours, and quenched to colorless by addition of acetic acid. After a few minutes, saturated aqueous sodium carbonate (15 mL) was added. The organic layer was separated, and the aqueous solution was extracted with methylene chloride (3×50 mL). The combined organic layer and extracts were dried over magnesium sulfate, and concentrated in vacuo to give the titled compound. The material was used directly for next step without further purification.

Example 1B 7-bromo-3,4,5,6-tetrahydro-1H-2,5-ethanoazepino[4,3-b]indole

A mixture of (2-bromophenyl)hydrazine hydrochloride (1.5 g, 6.71 mmol; Aldrich) and the product of Example 1A (0.94 g, 6.71 mmol) was combined with a solution of HCl in acetic acid (1.0 M, 20 mL; Aldrich) and stirred at 105° C. for 18 hours. The reaction mixture was concentrated under vacuum. The residue was taken up in toluene (100 mL) and concentrated under vacuum to remove most of the acetic acid (the azeotrope procedure was repeated a second time). The residue was dissolved in dimethyl sulfoxide (20 mL) and purified by reverse-phase HPLC [Waters XBridge™ RP18 column, 5 μm, 50×100 mm, flow rate 100 mL/minute, 40-99% gradient of methanol in buffer (0.1 M aqueous ammonium bicarbonate, adjusted to pH 10 with ammonium hydroxide)] to afford the title compound: $^1$H NMR (400 MHz, methanol-$d_4$) δ ppm 2.05-2.13 (m, 4 H), 3.08 (pent, J=6.9 Hz, 2 H), 3.15 (pent, J=3.6 Hz, 1 H), 3.26 (pent, J=7.2 Hz, 2 H), 4.23 (s, 2 H), 6.88 (t, J=7.8 Hz, 1 H), 7.19 (d, J=7.6 Hz, 1 H), 7.27 (d, J=7.9 Hz, 1 H); MS (APCI) m/z 291/293 (M+H)$^+$.

Example 1C

2-methyl-5-vinylpyridine

Water (10 mL) was added to a mixture of potassium vinyltrifluoroborate (6.35 g, 47.4 mmol, Aldrich), 5-bromo-2-methylpyridine (8.00 g, 46.5 mmol,), triphenylphosphine (0.732 g, 2.79 mmol) and $Cs_2CO_3$ (45.5 g, 140 mmol) in a 500 mL round-bottom flask with stir bar. The flask was evacuated and purged with nitrogen (3 cycles), and the mixture was heated under nitrogen at 75-80° C. for 19 hours, and then cooled to room temperature. The mixture was diluted with water (100 mL) and hexanes (50 mL), and the aqueous layer was drawn off and extracted with ether-hexanes (4:1, 50 mL). The combined organic phases were washed with brine (25 mL), dried over $Na_2SO_4$ and distilled at atmospheric pressure to a volume of ca. 10 mL. The residue was distilled under vacuum (90-100° C./20 Torr) to provide the title compound: $^1H$ NMR (400 MHz, methanol-$d_4$) δ ppm 2.51 (s, 3 H) 5.35 (d, J=11.1 Hz, 1 H) 5.86 (d, J=17.8 Hz, 1 H) 6.74 (dd, J=17.8, 11.1 Hz, 1 H) 7.27 (d, J=7.9 Hz, 1 H) 7.84 (dd, J=8.3, 2.4 Hz, 1 H) 8.40 (d, J=2.0 Hz, 1 H).

Example 1D

7-[(E)-2-(6-methylpyridin-3-yl)vinyl]-3,4,5,6-tetrahydro-1H-2,5-ethanoazepino[4,3-b]indole A mixture of bis(tri-t-butylphosphino)palladium (26.3 mg, 0.052 mmol; Aldrich), the product of Example 1C (123 mg, 0.52 mmol), sodium t-butoxide (124 mg, 1.29 mmol; Aldrich) and the product of Example 1B (150 mg, 0.52 mmol) was combined with 1,4-dioxane (3 mL). The mixture was purged with a stream of nitrogen for 2 minutes, then heated at 105° C. for 6 hours in a sealed tube. The reaction mixture was cooled to room temperature and concentrated under vacuum. The residue was dissolved in dimethyl sulfoxide (5 mL), filtered through a glass microfiber frit and purified by reverse-phase HPLC [Waters XBridge™ RP18 column, 5 μm, 30×100 mm, flow rate 40 mL/minute, 40-99% gradient of methanol in buffer (0.1 M aqueous ammonium bicarbonate, adjusted to pH 10 with ammonium hydroxide)] to afford the title compound: $^1H$ NMR (400 MHz, methanol-$d_4$) δ ppm 2.05-2.15 (m, 4 H), 2.54 (s, 3 H), 3.02-3.12 (m, 2 H), 3.14 (pent, J=3.6 Hz, 1 H), 3.20-3.29 (m, 2 H), 4.23 (s, 2 H), 7.02 (t, J=7.6 Hz, 1 H), 7.23 (d, J=16.5 Hz, 1 H), 7.24-7.27 (m, 1 H), 7.31 (d, J=8.2 Hz, 1 H), 7.39 (d, J=7.3 Hz, 1 H), 7.68 (d, J=16.5 Hz, 1 H), 8.01 (dd, J=8.2, 2.4 Hz, 1 H), 8.61 (d, J=2.4 Hz, 1 H); MS (APCI) m/z=330 (M+H)$^+$.

Example 2

7-[2-(6-methylpyridin-3-yl)ethyl]-3,4,5,6-tetrahydro-1H-2,5-ethanoazepino[4,3-b]indole Adam's catalyst ($PtO_2$, 7 mg, 0.031 mmol; Aldrich) was added to a solution of the product of Example 1D (60 mg, 0.18 mmol) in ethanol (5 mL). The reaction flask was evacuated and purged with nitrogen (3 cycles) then evacuated and purged with hydrogen (4 cycles), and the mixture was stirred under hydrogen (1 atm) at room temperature for 18 hours. The flask was evacuated and purged with nitrogen (3 cycles), and the reaction mixture was filtered. The filtrate was concentrated under vacuum, and the residue was purified by reverse-phase HPLC [Waters XBridge™ RP18 column, 5 μm, 30×100 mm, flow rate 40 mL/minute, 35-99% gradient of methanol in buffer (0.1 M aqueous ammonium bicarbonate, adjusted to pH 10 with ammonium hydroxide)] to afford the title compound: $^1H$ NMR (500 MHz, methanol-$d_4$) δ ppm 2.06 (td, J=7.3, 3.7 Hz, 4 H), 2.45 (s, 3 H), 2.99 (t, J=7.6 Hz, 2 H), 3.01-3.09 (m, 3 H), 3.11 (t, J=7.6 Hz, 2 H), 3.23 (dq, J=7.3, 7.1 Hz, 2 H), 4.20 (s, 2 H), 6.77 (d, J=7.0 Hz, 1 H), 6.88 (t, J=7.5 Hz, 1 H), 7.13 (d, J=7.6 Hz, 1 H), 7.14 (d, J=7.9 Hz, 1 H), 7.49 (dd, J=7.9, 2.1 Hz, 1 H), 8.11 (d, J=1.8 Hz, 1 H); MS (APCI) m/z 332 (M+H)$^+$.

Example 3

7-[(6-methylpyridin-3-yl)ethynyl]-3,4,5,6-tetrahydro-1H-2,5-ethanoazepino[4,3-b]indole Triethylamine (2 mL) was added to a mixture of bis(tri-t-butylphosphino)palladium (8.8 mg, 0.017 mmol; Aldrich), 5-ethynyl-2-methylpyridine (60 mg, 0.52 mmol; International Publication No. WO2005090333), CuI (3.3 mg, 0.017 mmol; Aldrich) and the product of Example 1B (100 mg, 0.34 mmol) in anhydrous tetrahydrofuran (2 mL). The mixture was purged with a nitrogen stream for 2 minutes, then stirred under nitrogen at 100° C. for 5 hours in a sealed tube. The mixture was cooled to ambient temperature and concentrated under vacuum. The residue was taken up in dimethyl sulfoxide (5 mL), filtered through a glass microfiber frit and purified by reverse-phase HPLC [Waters XBridge™ RP18 column, 5 μm, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1H$ NMR (500 MHz, methanol-$d_4$) δ ppm 2.05-2.16 (m, 4 H), 2.56 (s, 3 H), 3.02-3.12 (m, 2 H), 3.17-3.21 (m, 1 H), 3.21-3.29 (m, 2 H), 4.24 (s, 2 H), 7.00 (t, J=7.6 Hz, 1 H), 7.24 (dd, J=7.3, 0.9 Hz, 1 H), 7.34 (d, J=7.9 Hz, 1 H), 7.36 (dd, J=7.9, 0.9 Hz, 1 H), 7.94 (dd, J=8.1, 2.3 Hz, 1 H), 8.68 (d, J=1.8 Hz, 1H); MS (APCI) m/z 328 (M+H)$^+$.

Example 4

7-[(E)-2-(4-chlorophenyl)vinyl]-3,4,5,6-tetrahydro-1H-2,5-ethanoazepino[4,3-b]indole A suspension of the product of Example 1B (55 mg, 0.19 mmol), trans-2-(4-chlorophenyl)vinylboronic acid (41 mg, 0.23 mmol; Aldrich), dichlorobis(triphenylphosphine)palladium (II) (6.6 mg, 9.4 μmmol; Aldrich) and 1.0 M sodium carbonate (0.47 mL) in 2-propanol (1.5 mL) was purged with nitrogen and then stirred at 110° C. for 5 hours in a sealed tube. The reaction mixture was cooled and partitioned between $CHCl_3$/2-propanol (4:1, 2×20 mL) and 1.0 M sodium carbonate (30 mL). The combined organic extracts were dried (sodium sulfate) and concentrated under vacuum. The resulting residue was purified by reverse-phase HPLC [Waters XBridge™ RP18 column, 5 μm, 30×100 mm, flow rate 40 mL/minute, 40-99% gradient of methanol in buffer (0.1 M aqueous ammonium bicarbonate, adjusted to pH 10 with ammonium hydroxide)] to afford the title compound: $^1H$ NMR (500 MHz, methanol-$d_4$) δ ppm 2.03-2.16 (m, 4 H), 3.04-3.12 (m, 2 H), 3.12-3.18 (m, 1 H), 3.20-3.29 (m, 2 H), 4.24 (s, 2 H), 7.01 (t, J=7.6 Hz, 1 H), 7.19-7.26 (m, 2 H), 7.31-7.41 (m, 3 H), 7.55-7.67 (m, 3 H); MS (APCI) m/z 349 (M+H)$^+$.

Example 5

7-[(1E)-5-phenylpent-1-enyl]-3,4,5,6-tetrahydro-1H-2,5-ethanoazepino[4,3-b]indole A suspension of the product of Example 1B (110 mg, 0.38 mmol) and 5-phenyl-1-pentenylboronic acid pinacol ester (123 mg, 0.45 mmol; Alfa) was processed as described in Example 4 to provide the title compound: $^1$H NMR (500 MHz, methanol-$d_4$) δ ppm 1.79-1.90 (m, 2 H), 2.00-2.14 (m, 4 H), 2.28-2.37 (m, 2 H), 2.69 (t, J=7.0 Hz, 2 H), 3.00-3.08 (m, 2 H), 3.08-3.11 (m, 1 H), 3.22 (ddd, J=14.1, 8.5, 5.8 Hz, 2 H), 4.20 (s, 2 H), 6.33 (dt, J=15.9, 7.0 Hz, 1 H), 6.77 (d, J=15.9 Hz, 1 H), 6.93 (t, J=7.6 Hz, 1 H), 7.12-7.17 (m, 3 H), 7.18-7.22 (m, 2 H), 7.22-7.28 (m, 2 H); MS (APCI) m/z 357 (M+H)$^+$. Anal. Calcd. for $C_{25}H_{28}N_2 \cdot 0.2H_2O$: C, 83.38; H, 7.95; N, 7.78. Found: C, 83.29; H, 7.66; N, 7.68.

Example 6

7-[(E)-2-thien-3-ylvinyl]-3,4,5,6-tetrahydro-1H-2,5-ethanoazepino[4,3-b]indole

A suspension of the product of Example 1B (90 mg, 0.31 mmol) and E-2-(thiophenyl-3-yl)vinylboronic acid pinacol ester (88 mg, 0.37 mmol; Aldrich) was processed as described in Example 4 to provide the title compound: $^1$H NMR (500 MHz, methanol-$d_4$) δ ppm 2.03-2.16 (m, 4 H), 3.03-3.12 (m, 2 H), 3.12-3.16 (m, 1 H), 3.25 (ddd, J=14.0, 8.4, 6.0 Hz, 2 H), 4.24 (s, 2 H), 6.99 (t, J=7.6 Hz, 1 H), 7.21 (dd, J=7.6, 0.7 Hz, 1 H), 7.27 (d, J=16.2 Hz, 1 H), 7.33 (d, J=7.3 Hz, 1 H), 7.38-7.42 (m, 2 H), 7.45 (d, J=16.5 Hz, 1 H), 7.52 (dd, J=4.9, 0.9 Hz, 1 H); MS (APCI) m/z=321 (M+H)$^+$.

Example 7

7-(5-phenylpentyl)-3,4,5,6-tetrahydro-1H-2,5-ethanoazepino[4,3-b]indole

The product of Example 5 (70 mg, 0.20 mmol) was processed as described in Example 2 to provide the title compound: $^1$H NMR (500 MHz, methanol-$d_4$) δ ppm 1.36-1.48 (m, 2 H), 1.64 (pent, J=7.6 Hz, 2 H), 1.73 (pent, J=7.6 Hz, 2 H), 2.00-2.14 (m, 4 H), 2.57 (t, J=7.6 Hz, 2 H), 2.81 (t, J=7.5 Hz, 2 H), 3.01-3.12 (m, 3 H), 3.23 (ddd, J=14.0, 8.2, 6.1 Hz, 2 H), 4.22 (s, 2 H), 6.80-6.83 (m, 1 H), 6.89 (t, J=7.5 Hz, 1 H), 7.08-7.13 (m, 4 H), 7.18-7.23 (m, 2 H); MS (APCI) m/z 359 (M+H)$^+$.

Example 8

9-[(E)-2-(6-methylpyridin-3-yl)vinyl]-3,4,5,6-tetrahydro-1H-2,5-ethanoazepino[4,3-b]indole Example 8A 9-bromo-3,4,5,6-tetrahydro-1H-2,5-ethanoazepino[4,3-b]indole 4-Bromophenylhydrazine hydrochloride (4.33 g, 19.37 mmol; Aldrich) and the product of Example 1A (2.70 g, 19.37 mmol) were processed as described in Example 1B to provide the title compound: $^1$H NMR (300 MHz, methanol-$d_4$) δ ppm 2.14-2.36 (m, 4 H), 3.17-3.25 (m, 1 H), 3.33-3.45 (m, 2 H), 3.45-3.65 (m, 2 H), 4.54 (s, 2 H), 7.18 (dd, J=8.8, 1.8 Hz, 1 H), 7.24 (d, J=9.1 Hz, 1 H), 7.51 (d, J=2.4 Hz, 1 H); MS (DCI) m/z 291/293 (M+H)$^+$.

Example 8B

9-[(E)-2-(6-methylpyridin-3-yl)vinyl]-3,4,5,6-tetrahydro-1H-2,5-ethanoazepino[4,3-b]indole The product of Example 1C (133 mg, 1.11 mmol) and the product of Example 8A (180 mg, 0.62 mmol) were processed as described in Example 1D to provide the title compound: $^1$H NMR (500 MHz, methanol-$d_4$) δ ppm 2.03-2.14 (m, 4 H), 2.52 (s, 3 H), 2.98-3.04 (m, 1 H), 3.08 (dt, J=14.0, 6.9 Hz, 2 H), 3.20-3.29 (m, 2 H), 4.27 (s, 2 H), 7.05 (d, J=16.2 Hz, 1 H), 7.27 (d, J=8.2 Hz, 2 H), 7.33 (d, J=16.2 Hz, 1 H), 7.35-7.38 (m, 1 H), 7.49 (s, 1 H), 7.94 (dd, J=7.9, 2.1 Hz, 1 H), 8.50 (d, J=1.8 Hz, 1 H); MS (APCI) m/z 330 (M+H)$^+$.

Example 9

9-[2-(6-methylpyridin-3-yl)ethyl]-3,4,5,6-tetrahydro-1H-2,5-ethanoazepino[4,3-b]indole The product of Example 8B (30 mg, 0.09 mmol) was processed as described in Example 2 to provide the title compound: $^1$H NMR (400 MHz, methanol-$d_4$) δ ppm 2.02-2.10 (m, 4H), 2.45 (s, 3H), 2.91-2.96 (m, 4H), 2.97-3.01 (m, 1H), 3.01-3.10 (m, 2H), 3.17-3.27 (m, 2H), 4.16 (s, 2H), 6.83 (dd, J=8.2, 1.8 Hz, 1H), 7.00 (d, J=0.9 Hz, 1H), 7.15 (d, J=8.2 Hz, 1H), 7.16 (d, J=7.9 Hz, 1H), 7.50 (dd, J=8.1, 2.3 Hz, 1H), 8.05 (d, J=2.1 Hz, 1H); MS (APCI) m/z 332 (M+H)$^+$.

Example 10

7-[(E)-2-(4-fluorophenyl)vinyl]-3,4,5,6-tetrahydro-1H-2,5-ethanoazepino[4,3-b]indole The product of Example 1B (62.4 mg, 0.21 mmol) and trans-2-(4-fluorophenyl)vinylboronic acid (56.9 mg, 0.343 mmol, Aldrich) were processed according to the method described in Example 4 and purified by reverse-phase HPLC (Waters XBridge™ C18 5 μm OBD 30×100 mm column, flow rate 40 mL/minute, 5-95% gradient of acetonitrile in 0.1% trifluoroacetic acid over 15 minutes) to afford the title compound as the trifluoroacetic acid salt: $^1$H NMR (300 MHz, methanol-$d_4$) δ ppm 2.32-2.45 (m, 4 H), 3.41-3.44 (m, 1 H), 3.50-3.56 (m, 2 H), 3.64-3.72 (m, 2 H), 4.76 (s, 2 H), 7.07-7.15 (m, 3 H), 7.24-7.33 (m, 2 H), 7.47 (d, J=7.5 Hz, 1 H), 7.54 (d, J=16.3 Hz, 1 H), 7.62-7.69 (m, 2 H); MS (DCI/NH$_3$) m/z 333 (M+H)$^+$. Anal. Calcd. for $C_{22}H_{21}FN_2 \cdot 1.3$ TFA: C, 61.47; H, 4.68; N, 5.83. Found: C, 61.62; H, 5.01; N, 5.97.

Example 11

7-[(E)-2-pyridin-4-ylvinyl]-3,4,5,6-tetrahydro-1H-2,5-ethanoazepino[4,3-b]indole The product of Example 1B (100 mg, 0.34 mmol), 4-vinylpyridine (144 mg, 1.37 mmol; Aldrich) and MgSO$_4$ (83 mg, 0.69 mmol) were combined and processed as described in Example 1D to provide the title compound: $^1$H NMR (400 MHz, methanol-$d_4$) δ ppm 1.97-2.22 (m, 4 H), 3.03-3.12 (m, 2 H), 3.13-3.18 (m, 1 H), 3.21-3.29 (m, 2 H), 4.24 (s, 2 H), 7.04 (t, J=7.6 Hz, 1 H), 7.24 (d, J=16.5 Hz, 1 H), 7.31 (dd, J=7.8, 0.8 Hz, 1 H), 7.44 (d, J=7.6 Hz, 1 H), 7.59-7.69 (m, 2 H), 7.94 (d, J=16.5 Hz, 1 H), 8.46-8.50 (m, 2 H); MS (APCI) m/z 316 (M+H)$^+$.

Example 12

7-[(E)-2-pyridin-2-ylvinyl]-3,4,5,6-tetrahydro-1H-2,5-ethanoazepino[4,3-b]indole The product of Example 1B (110 mg, 0.38 mmol; Aldrich) and 2-vinylpyridine (40 mg, 0.38 mmol; Aldrich) were processed as described in Example 1D to provide the title compound: $^1$H NMR (500 MHz, methanol-$d_4$) δ ppm 2.04-2.17

(m, 4 H), 3.04-3.12 (m, 2 H), 3.13-3.17 (m, 1 H), 3.26 (ddd, J=14.1, 8.5, 5.8 Hz, 2 H), 4.25 (s, 2 H), 7.04 (t, J=7.6 Hz, 1 H), 7.26 (ddd, J=7.4, 5.0, 1.1 Hz, 1 H), 7.28-7.34 (m, 2 H), 7.41 (d, J=7.3 Hz, 1 H), 7.71-7.74 (m, J=7.9 Hz, 1 H), 7.82 (td, J=7.6, 1.8 Hz, 1 H), 7.93-8.01 (m, 1 H), 8.51 (dd, J=5.0, 0.8 Hz, 1 H); MS (APCI) m/z 316 (M+H)$^+$.

Example 13

7-(pyridin-3-ylethynyl)-3,4,5,6-tetrahydro-1H-2,5-ethanoazepino[4,3-b]indole The product of Example 1B (130 mg, 0.45 mmol) and 3-ethynylpyridine (74 mg, 0.72 mmol; Aldrich) were processed according to the method described in Example 3 and purified by reverse-phase HPLC (Waters XBridge™ C18 5 μm OBD 30×100 mm column, flow rate 40 mL/minute, 5-95% gradient of acetonitrile in 0.1% trifluoroacetic acid over 15 minutes) to afford the title compound as the bis trifluoroacetate: $^1$H NMR (500 MHz, methanol-$d_4$) δ ppm 2.26-2.35 (m, 2 H), 2.36-2.45 (m, 2 H), 3.44-3.48 (m, 1 H), 3.48-3.56 (m, 2 H), 3.69 (ddd, J=13.8, 8.9, 5.3 Hz, 2 H), 4.77 (s, 2 H), 7.12 (t, J=7.6 Hz, 1 H), 7.39 (d, J=7.0 Hz, 1 H), 7.51 (d, J=7.9 Hz, 1 H), 7.74 (dd, J=8.1, 5.3 Hz, 1 H), 8.37 (dt, J=8.0, 1.6 Hz, 1 H), 8.65 (d, J=4.6 Hz, 1 H), 8.96 (s, 1 H); MS (APCI) m/z 314 (M+H)$^+$. Anal. Calcd. for $C_{21}H_{19}N_3$.2.85 TFA: C, 50.24; H, 3.45; N, 6.58. Found: C, 49.97; H, 3.54; N, 6.80.

Example 14

7-[(E)-2-(2,4-difluorophenyl)vinyl]-3,4,5,6-tetrahydro-1H-2,5-ethanoazepino[4,3-b]indole A suspension of the product of Example 1B (100 mg, 0.34 mmol) and trans-2-(2,4-difluorophenyl)vinylboronic acid pinacol ester (101 mg, 0.38 mmol; Aldrich) was processed as described in Example 4 to provide the title compound: $^1$H NMR (400 MHz, methanol-$d_4$) δ ppm 1.98-2.19 (m, 4 H), 3.03-3.17 (m, 3 H), 3.21-3.28 (m, 2 H), 4.24 (s, 2 H), 6.93-7.05 (m, 3 H), 7.25 (d, J=7.6 Hz, 1 H), 7.30 (d, J=16.2 Hz, 1 H), 7.37 (d, J=7.3 Hz, 1 H), 7.63 (d, J=16.5 Hz, 1 H), 7.79-7.88 (m, 1 H); MS (DCI) m/z 351 (M+H)$^+$.

Example 15

7-[(E)-2-(3-fluorophenyl)vinyl]-3,4,5,6-tetrahydro-1H-2,5-ethanoazepino[4,3-b]indole The product of Example 1B (120 mg, 0.41 mmol) and (E)-2-(3-fluorophenyl)vinylboronic acid (82 mg, 0.50 mmol; Aldrich) were processed as described in Example 4 to provide the title compound: $^1$H NMR (400 MHz, DMSO-$d_6$) δ ppm 1.93-2.01 (m, 4H), 2.88-3.02 (m, 2 H), 3.04-3.10 (m, 1 H), 3.11-3.22 (m, 2 H), 4.12 (s, 2 H), 6.98 (t, J=7.6 Hz, 1 H), 7.06-7.14 (m, 1 H), 7.22 (d, J=7.6 Hz, 1 H), 7.30 (d, J=16.2 Hz, 1 H), 7.38-7.42 (m, 1 H), 7.42-7.50 (m, 2 H), 7.52-7.58 (m, 1 H), 7.77 (d, J=16.5 Hz, 1 H); MS (DCI) m/z 333 (M+H)$^+$.

Example 16

7-[2-(3-fluorophenyl)ethyl]-3,4,5,6-tetrahydro-1H-2,5-ethanoazepino[4,3-b]indole The product of Example 15 (60 mg, 0.18 mmol) was processed as described in Example 2 to provide the title compound: $^1$H NMR (500 MHz, methanol-$d_4$) δ ppm 2.02-2.12 (m, 4 H), 2.97-3.02 (m, 2 H), 3.03-3.14 (m, 5 H), 3.19-3.28 (m, 2 H), 4.22 (s, 2 H), 6.81 (d, J=7.0 Hz, 1 H), 6.86 (td, J=8.6, 2.6 Hz, 1 H), 6.89 (t, J=7.5 Hz, 1 H), 6.94 (dt, J=12.2, 1.8 Hz, 1 H), 7.01 (d, J=7.6 Hz, 1 H), 7.14 (dd, J=7.8, 0.8 Hz, 1 H), 7.19-7.26 (m, 1 H); MS (DCI) m/z 335 (M+H)$^+$.

Example 17

8-[(E)-2-(6-methylpyridin-3-yl)vinyl]-3,4,5,6-tetrahydro-1H-2,5-ethanoazepino[4,3-b]indole

Example 17A mixture of 10-bromo-3,4,5,6-tetrahydro-1H-2,5-ethanoazepino[4,3-b]indole and 8-bromo-3,4,5,6-tetrahydro-1H-2,5-ethanoazepino[4,3-b]indole 3-Bromophenylhydrazine hydrochloride (2.25 g, 10.1 mmol; Aldrich) and the product of Example 1A (1.40 g, 10.1 mmol) were processed as described in example 1B to provide a single HPLC fraction which was concentrated to afford the titled mixture: $^1$H NMR (300 MHz, DMSO-$d_6$) δ ppm 1.83-2.01 (m, 4 H), 2.84-3.03 (m, 3 H), 3.04-3.19 (m, 2 H), 6.86 (t, J=7.7 Hz, 0.4H, H8 of 10-bromo isomer), 7.03 (dd, J=8.3, 2.0 Hz, 0.6H, H10 of 8-bromo isomer), 7.07 (dd, J=7.5, 0.8 Hz, 0.4 H, H7 of 10-bromo isomer), 7.21 (d, J=8.3 Hz, 0.6 H, H9 of 8-bromo isomer), 7.25 (dd, J=7.9, 0.8 Hz, 0.4 H, H9 of 10-bromo isomer), 7.42 (d, J=1.6 Hz, 0.6 H, H7 of 8-bromo isomer), 10.87 (s, 0.6 H, H6 of 8-bromo isomer), 11.05 (s, 0.4H, H6 of 10-bromo isomer); MS (APCI) m/z 291/293 (M+H)$^+$.

Example 17B

(E)-2-methyl-5-(2-(4,4,5,5-tetramethyl-1,3,2-dioxaborolan-2-yl)vinyl)pyridine A dry 500-mL round-bottom flask was charged with carbonylchlorohydrido-tris(triphenylphosphine) ruthenium(II) (0.571 g, 0.600 mmol; Aldrich) and toluene (80 mL) under nitrogen. After pinacolborane (3.19 mL 22.00 mmol, Aldrich) and 5-ethynyl-2-methylpyridine (2.343 g, 20 mmol; International Publication No. WO2005090333) were added, the mixture was stirred at room temperature for 16 hours. The reaction mixture was extracted with ether, then the extract was washed with water, dried over MgSO$_4$ and concentrated. The resulting material was purified by flash chromatography (silica gel, hexanes/ethyl acetate, 3:1) to afford the title compound: $^1$H NMR (300 MHz, CDCl$_3$) δ ppm 1.31 (s, 12 H), 2.55 (s, 3 H), 6.19 (d, J=19.0 Hz, 1 H), 7.13 (d, J=8.0 Hz, 1 H), 7.36 (d, J=18.0 Hz, 1 H), 7.71 (dd, J=8.0, 2.0 Hz, 1 H), 8.56 (d, J=2.0 Hz, 1 H); MS (DCI/NH$_3$) m/z 246 (M+H)$^+$.

Example 17C

8-[(E)-2-(6-methylpyridin-3-yl)vinyl]-3,4,5,6-tetrahydro-1H-2,5-ethanoazepino[4,3-b]indole The product of Example 17A (145 mg, 0.50 mmol) and the product of Example 17B (183 mg, 0.75 mmol) were processed as described in Example 4 to provide a mixture of the title compound and its 10-substituted isomer. These were separated by reverse-phase HPLC [Waters XBridge™ RP18 column, 5 μm, 30×100 mm, flow rate 40 mL/minute, 20-99% gradient of methanol in buffer (0.1 M aqueous ammonium bicarbonate, adjusted to pH 10 with ammonium hydroxide)]

to afford the pure title compound: $^1$H NMR (400 MHz, methanol-d$_4$) δ ppm 2.00-2.21 (m, 4H), 2.53 (s, 3 H), 3.00-3.06 (pent, J=2.6 Hz, 1 H), 3.08-3.18 (m, 2 H), 3.20-3.29 (m, 2 H), 4.56 (br s, 2 H), 7.04 (d, J=7.6 Hz, 1 H), 7.07 (d, J=0.9 Hz, 1 H), 7.22 (dd, J=8.1, 0.8 Hz, 1 H), 7.27-7.36 (m, J=12.4, 7.8 Hz, 2 H), 7.66 (d, J=16.2 Hz, 1 H), 7.95 (dd, J=8.1, 2.3 Hz, 1 H), 8.50 (d, J=2.1 Hz, 1 H); MS (DCI) m/z 330 (M+H)$^+$.

Example 18

10-[(E)-2-(6-methylpyridin-3-yl)vinyl]-3,4,5,6-tetrahydro-1H-2,5-ethanoazepino[4,3-b]indole Reverse-phase HPLC purification of the mixture described in Example 17C also provided the 10-substituted title compound: $^1$H NMR (400 MHz, methanol-d$_4$) δ ppm 1.98-2.19 (m, 4 H), 2.53 (s, 3 H), 3.04 (ddd, J=7.1, 4.7, 2.6 Hz, 1 H), 3.08-3.18 (m, 2 H), 3.25 (ddd, J=14.3, 9.1, 5.3 Hz, 2 H), 4.58 (s, 2 H), 7.02-7.08 (m, 2 H), 7.22 (dd, J=8.1, 0.8 Hz, 1 H), 7.27-7.35 (m, 2 H), 7.66 (d, J=16.2 Hz, 1 H), 7.95 (dd, J=8.1, 2.3 Hz, 1 H), 8.50 (d, J=2.1 Hz, 1 H); MS (ESI) m/z 330 (M+H)$^+$.

Example 19

7-[(E)-2-phenylvinyl]-3,4,5,6-tetrahydro-1H-2,5-ethanoazepino[4,3-b]indole

The product of Example 1B (100 mg, 0.34 mmol) and (E)-phenylethenylboronic acid (56 mg, 0.38 mmol; Aldrich) were processed as described in Example 4 to provide the title compound: $^1$H NMR (400 MHz, methanol-d$_4$) δ ppm 2.03-2.18 (m, 4 H), 3.04-3.13 (m, 2 H), 3.13-3.18 (m, 1 H), 3.21-3.28 (m, 2 H), 4.24 (s, 2 H), 7.01 (t, J=7.6 Hz, 1 H), 7.19-7.28 (m, 3 H), 7.32-7.41 (m, 3 H), 7.60 (d, J=12.2 Hz, 1 H), 7.62-7.65 (m, 2 H); MS (DCI) m/z 315 (M+H)$^+$.

Example 20

7-{[4-(trifluoromethoxy)phenyl]ethynyl}-3,4,5,6-tetrahydro-1H-2,5-ethanoazepino[4,3-b]indole The product of Example 1B (100 mg, 0.34 mmol), 4-(trifluoromethoxy)phenylacetylene (192 mg, 1.03 mmol; Aldrich) and MgSO$_4$ (83 mg, 0.69 mmol) were combined and processed as described in Example 3 to provide the title compound: $^1$H NMR (400 MHz, methanol-d$_4$) δ ppm 2.00-2.24 (m, 4 H), 3.03-3.14 (m, 2 H), 3.17-3.21 (m, 1 H), 3.25 (ddd, J=14.2, 8.4, 6.1 Hz, 2 H), 4.24 (s, 2 H), 7.00 (t, J=7.6 Hz, 1 H), 7.23 (dd, J=7.3, 0.9 Hz, 1 H), 7.28-7.33 (m, 2 H), 7.35 (dd, J=7.9, 1.2 Hz, 1 H), 7.71-7.77 (m, 2 H); MS (APCI) m/z 397 (M+H)$^+$.

Example 21

7-(pyridin-4-ylethynyl)-3,4,5,6-tetrahydro-1H-2,5-ethanoazepino[4,3-b]indole

The product of Example 1B (100 mg, 0.34 mmol), 4-ethynylpyridine hydrochloride (144 mg, 1.03 mmol; Aldrich) and MgSO$_4$ (83 mg, 0.69 mmol) were combined and processed as described in Example 3 to provide the title compound: $^1$H NMR (400 MHz, methanol-d$_4$) δ ppm 2.05-2.16 (m, 4 H), 3.03-3.14 (m, 2 H), 3.18-3.22 (m, 1 H), 3.22-3.29 (m, 2 H), 4.26 (s, 2 H), 7.03 (t, J=7.6 Hz, 1 H), 7.29 (dd, J=7.5, 0.8 Hz, 1 H), 7.41 (dd, J=7.9, 0.9 Hz, 1 H), 7.62-7.66 (m, 2 H), 8.53-8.58 (m, 2 H); MS (APCI) m/z 314 (M+H)$^+$.

Example 22

8-[(6-methylpyridin-3-yl)ethynyl]-3,4,5,6-tetrahydro-1H-2,5-ethanoazepino[4,3-b]indole The product of Example 17A (412 mg, 1.42 mmol), (144 mg, 1.03 mmol; Aldrich), 5-ethynyl-2-methylpyridine (265 mg, 2.26 mmol; International Publication No. WO2005090333) and MgSO$_4$ (85 mg, 0.71 mmol) were combined and processed as described in Example 3 to provide the title compound: $^1$H NMR (400 MHz, methanol-d$_4$) δ ppm 2.03-2.16 (m, 4 H), 2.55 (s, 3 H), 3.02-3.14 (m, 3 H), 3.21-3.29 (m, 2 H), 4.25 (s, 2 H), 7.15 (dd, J=8.2, 1.2 Hz, 1 H), 7.28-7.33 (m, 2 H), 7.47-7.48 (m, 1 H), 7.82 (dd, J=8.2, 2.1 Hz, 1 H), 8.52 (d, J=1.8 Hz, 1 H); MS (APCI) m/z 328 (M+H)$^+$.

Example 23

10-[(6-methylpyridin-3-yl)ethynyl]-3,4,5,6-tetrahydro-1H-2,5-ethanoazepino[4,3-b]indole Reverse-phase HPLC purification of Example 22 also provided the title compound: $^1$H NMR (400 MHz, methanol-d$_4$) δ ppm 2.02-2.17 (m, 4 H), 2.56 (s, 3 H), 3.04 (ddd, J=7.2, 4.6, 2.6 Hz, 1 H), 3.08-3.18 (m, 2 H), 3.25 (ddd, J=14.2, 8.9, 5.3 Hz, 2 H), 4.68 (s, 2 H), 7.02 (dd, J=8.1, 7.5 Hz, 1 H), 7.16 (dd, J=7.3, 0.9 Hz, 1 H), 7.31 (dd, J=8.2, 0.9 Hz, 1 H), 7.33 (d, J=8.0 Hz, 1 H), 7.87 (dd, J=7.9, 2.1 Hz, 1 H), 8.57 (d, J=1.5 Hz, 1 H); MS (APCI) m/z 328 (M+H)$^+$.

Example 24

9-fluoro-7-[(6-methylpyridin-3-yl)ethynyl]-3,4,5,6-tetrahydro-1H-2,5-ethanoazepino[4,3-b]indole

Example 24A 7-bromo-9-fluoro-3,4,5,6-tetrahydro-1H-2,5-ethanoazepino[4,3-b]indole (2-Bromo-4-fluorophenyl)hydrazine hydrochloride (1.14 g, 4.72 mmol; Enamine) was suspended in HCl-acetic acid (1.0 M, 25 mL; Aldrich). The product of Example 1A (684 mg, 4.91 mmol) was added and the reaction was heated to 80° C. for 5 hours. The reaction was then allowed to cool and then concentrated. The product was triturated with acetonitrile and isolated by filtration, washing with additional acetonitrile (2×10 mL). The solid was partitioned between 1.0 M NaOH (50 mL) and CHCl$_3$ (3×50 mL). The combined organic extracts were dried over Na$_2$SO$_4$, filtered and concentrated to give the title compound: $^1$H NMR (300 MHz, methanol-d$_4$) δ ppm 2.05-2.11 (m, 4H), 3.01-3.14 (m, 3H), 3.19-3.26 (m, 2H), 4.17 (s, 2H), 6.96-7.04 (m, 2H); MS (DCI/NH$_3$) m/z 309/311 (M+H)$^+$. Anal. Calcd. for C$_{14}$H$_{14}$BrFN$_2$: C, 54.39; H, 4.56; N, 9.06. Found: C, 54.04; H, 4.28; N, 8.90.

Example 24B 9-fluoro-7-[(6-methylpyridin-3-yl)ethynyl]-3,4,5,6-tetrahydro-1H-2,5-ethanoazepino[4,3-b]indole The product of Example 24A (148.6 mg, 0.48 mmol) and 5-ethynyl-2-methylpyridine (92.5 mg, 0.790 mmol; International Publication No. WO2005090333) were processed according to the method described in Example 3 to afford the title compound: $^1$H NMR (300 MHz, methanol-$d_4$) δ ppm 2.07-2.13 (m, 4H), 2.48-2.61 (m, 4H), 3.03-3.13 (m, 2H), 3.18-3.26 (m, 2H), 4.21 (s, 2H), 7.00 (dd, J=9.9, 2.4 Hz, 1H), 7.08 (dd, J=9.5, 2.4 Hz, 1H), 7.36 (d, J=7.9 Hz, 1H), 7.96 (dd, J=8.0, 2.1 Hz, 1H), 8.70 (d, J=2.0 Hz, 1H); MS (DCI/NH$_3$) m/z 346 (M+H)$^+$.

Example 25

9-fluoro-7-[(E)-2-(6-methylpyridin-3-yl)vinyl]-3,4,5,6-tetrahydro-1H-2,5-ethanoazepino[4,3-b]indole The product of Example 24A (105.4 mg, 0.34 mmol) and the product of Example 17B (124.9 mg, 0.510 mmol) were processed according to the method described in Example 4. Purification by reverse-phase HPLC (Waters XBridge™ C18 5 μm OBD 30×100 mm column, flow rate 40 mL/minute, 5-95% gradient of acetonitrile in 0.1% trifluoroacetic acid over 15 minutes) afforded the title compound as the trifluoroacetate: $^1$H NMR (300 MHz, methanol-$d_4$) δ ppm 2.30-2.46 (m, 4H), 2.79 (s, 3H), 3.39-3.41 (m, 1H), 3.51-3.58 (m, 2H), 3.65-3.75 (m, 2H), 4.74 (s, 2H), 7.15 (dd, J=8.9, 2.2 Hz, 1H), 7.35 (dd, J=10.7, 2.4 Hz, 1H), 7.42 (d, J=16.3 Hz, 1H), 7.88-7.95 (m, 2H), 8.71 (dd, J=8.5, 2.2 Hz, 1H), 8.85 (d, J=2.0 Hz, 1H); MS (DCI/NH$_3$) m/z 348 (M+H)$^+$. Anal. Calcd. for C$_{22}$H$_{22}$FN$_3$.3 TFA. 1.1H$_2$O: C, 47.41; H, 3.87; N, 5.92. Found: C, 47.20; H, 3.62; N, 5.75.

Example 26

7-(benzyloxy)-3,4,5,6-tetrahydro-1H-2,5-ethanoazepino[4,3-b]indole

Under nitrogen, (2-(benzyloxy)phenyl)hydrazine (214 mg, 1.0 mmol, International Publication No. WO2009001129) was mixed with the product of Example 1A (139 mg, 1.0 mmol) and sulfuric acid (0.2 mL, 3.76 mmol; J. T. Baker) in dry dioxane (10 mL). Then the mixture was heated to 80° C. and stirred for 16 hours in a sealed tube. The mixture was concentrated and basified with 1.0 M NaOH and then extracted with ethyl acetate (3×20 mL). The organic phase was concentrated and purified by reverse-phase HPLC [Waters XBridge™ RP18 column, 5 μm, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (300 MHz, methanol-$d_4$) δ ppm 2.01-2.13 (m, 4 H), 3.01-3.13 (m, 3 H), 3.17-3.28 (m, 2 H), 4.22 (s, 2 H), 5.21 (s, 2 H), 6.66 (dd, J=7, 2 Hz, 1 H), 6.83-6.93 (m, 2 H), 7.28-7.41 (m, 3 H), 7.48-7.55 (m, 2 H); MS (DCI/NH$_3$) m/z 319 (M+H)$^+$.

Example 27

7-quinolin-6-yl-3,4,5,6-tetrahydro-1H-2,5-ethanoazepino[4,3-b]indole

7-Bromo-3,4,5,6-tetrahydro-1H-2,5-ethanoazepino[4,3-b]indole (146 mg, 0.5 mmol, Example 1B) was coupled with 6-quinolineboronic acid pinacol ester (191 mg, 0.75 mmol, Aldrich) following the procedure described in Example 4. Purification by preparative reverse-phase HPLC [Waters XBridge™ RP18 column, 5 μm, 30×100 mm, flow rate 40 mL/minute, 40-99% gradient of methanol in buffer (0.1 M aqueous ammonium bicarbonate, adjusted to pH 10 with ammonium hydroxide)] gave the title compound: $^1$H NMR (300 MHz, methanol-$d_4$) δ ppm 1.99-2.18 (m, 4 H) 3.02-3.30 (m, 5 H) 4.29 (s, 2 H) 7.10-7.24 (m, 2 H) 7.36 (d, J=8 Hz, 1 H) 7.58 (dd, J=8, 4 Hz, 1 H) 8.04-8.10 (m, 1 H) 8.13-8.22 (m, 2 H) 8.45 (d, J=8 Hz, 1 H) 8.86 (dd, J=4, 2 Hz, 1 H); MS (DCI/NH$_3$) m/z 340 (M+H)$^+$.

Example 28

7-[(E)-2-(6-methylpyridin-3-yl)yinyl]-1,2,3,4,5,6-hexahydro-2,5-ethanoazepino[4,3-b]indole 2-oxide Aqueous H$_2$O$_2$ (50%, 0.2 mL, 2.91 mmol) was added at room temperature to a suspension of the product of example 1D (60 mg, 0.18 mmol) in acetonitrile (1 mL) and water (1 mL). After 1 hour, the reaction was quenched with saturated aqueous Na$_2$S$_2$O$_3$ and stirred for 1 hour longer. The mixture was poured into water and extracted with CH$_2$Cl$_2$ (2×25 mL, containing about 2 mL CH$_3$OH). The combined extracts were concentrated under vacuum, and the residue was purified by chromatography (silica gel, eluted with a 5-50% gradient of 14 M ammonium hydroxide-methanol-dichloromethane (2:20:78) in dichloromethane), and further purified by reverse-phase HPLC [Waters XBridge™ RP18 column, 5 μm, 30×100 mm, flow rate 40 mL/minute, 5-95% gradient of methanol in buffer (0.1 M aqueous ammonium bicarbonate, adjusted to pH 10 with ammonium hydroxide)] to afford the title compound: $^1$H NMR (300 MHz, methanol-$d_4$) δ ppm 2.18-2.33 (m, 2 H), 2.38-2.53 (m, 2 H), 2.54 (s, 3 H), 3.25-3.32 (m, 1 H), 3.67-3.89 (m, 4 H), 4.85 (s, 2 H), 7.09 (t, J=7.5 Hz, 1 H), 7.24 (d, J=16.7 Hz, 1 H), 7.30 (d, J=7.9 Hz, 2 H), 7.46 (d, J=7.5 Hz, 1 H), 7.65 (d, J=16.3 Hz, 1 H), 8.00 (dd, J=8.1, 2.2 Hz, 1 H), 8.61 (d, J=2.0 Hz, 1 H); MS (+ESI) m/z 346 (M+H)$^+$.

Example 29

7-[(E)-2-(pyrimidin-5-yl)vinyl]-3,4,5,6-tetrahydro-1H-2,5-ethanoazepino[4,3-b]indole Example 29A 5-vinylpyrimidine A suspension of 2,4,6-trivinylcyclotriboroxane pyridine complex (2.41 g, 10 mmol; Aldrich), 5-bromopyrimidine (1.59 g, 10 mmol; Aldrich), dichlorobis(triphenylphosphine) palladium (II) (0.35 g, 0.5 mmol; Aldrich) and sodium carbonate (2.65 g, 25 mmol) in a solvent mixture of 2-propanol (15 mL) and water (5 mL) was purged with nitrogen and then stirred at 100° C. for 2 hours in a sealed tube. The reaction mixture was cooled and partitioned between CH$_2$Cl$_2$ (2×200 mL) and water (200 mL). The combined organic extracts were dried (sodium sulfate) and concentrated under vacuum. The resulting residue was purified by reverse-phase HPLC [Waters XBridge™ RP18 column, 5 μm, 30×100 mm, flow rate 40 mL/minute, 20-50% gradient of methanol in buffer (0.1 M aqueous ammonium bicarbonate, adjusted to pH 10 with ammonium hydroxide)]. Fractions containing the product were first concentrated on the rotavap to remove most of the methanol and then partitioned between sodium carbonate (1.0 M, 100 mL) and CH$_2$Cl$_2$ (2×200 mL). The combined organic extracts were dried (sodium sulfate) and concentrated on the rotavap to provide the title compound: $^1$H NMR (300 MHz, methanol-$d_4$) δ ppm 5.54 (d, J=11.1 Hz, 1 H), 6.07 (d, J=17.8 Hz, 1 H), 6.77 (dd, J=17.8, 11.1 Hz, 1 H), 8.87 (s, 2 H), 9.02 (s, 1H); MS (APCI) m/z 107 (M+H)+.

Example 29B

7-[(E)-2-(pyrimidin-5-yl)vinyl]-3,4,5,6-tetrahydro-1H-2,5-ethanoazepino[4,3-b]indole The product of Example 1B (265 mg, 0.91 mmol), the product of Example 29A (193 mg, 1.82 mmol) and magnesium sulfate (55 mg, 0.46 mmol) were combined and processed as described in Example 1D to provide the title compound as the slower eluting compound: $^1$H NMR (400 MHz, methanol-$d_4$) δ ppm 2.04-2.20 (m, 4 H), 3.04-3.17 (m, 3 H), 3.22-3.30 (m, 2 H), 4.26 (s, 2 H), 7.05 (t, J=7.6 Hz, 1 H), 7.24 (d, J=16.8 Hz, 1 H), 7.31 (dd, J=7.9, 0.9 Hz, 1 H), 7.43-7.47 (m, J=7.3 Hz, 1 H), 7.89 (s, 1 H), 9.02 (d, J=16.1 Hz, 1 H), 9.04 (s, 2 H); MS (APCI) m/z 317 (M+H)+.

Example 30

7-[(Z)-2-(pyrimidin-5-yl)vinyl]-3,4,5,6-tetrahydro-1H-2,5-ethanoazepino[4,3-b]indole Reverse-phase HPLC purification of Example 29 also provided the title compound as the faster eluting compound: $^1$H NMR (500 MHz, methanol-$d_4$) δ ppm 1.96-2.10 (m, 4 H), 2.95-3.01 (m, 1 H), 3.03-3.13 (m, 2 H), 3.20-3.28 (m, 2 H), 4.28 (s, 2 H), 6.70 (d, J=11.9 Hz, 1 H), 6.89-6.96 (m, 2 H), 7.19 (d, J=11.9 Hz, 1 H), 7.29 (dd, J=7.6, 0.6 Hz, 1 H), 8.45 (s, 2 H), 8.83 (s, 1H); MS (APCI) m/z 317 (M+H)+.

Example 31

7-[(Z)-2-(6-methylpyridin-3-yl)vinyl]-3,4,5,6-tetrahydro-1H-2,5-ethanoazepino[4,3-b]indole The product of Example 3 (100.9 mg, 0.308 mmol) was dissolved in methanol (5 mL). Lindlar catalyst (5% Pd on $CaCO_3$ poisoned with lead, Aldrich, 9.8 mg) was added to the reaction mixture. The reaction flask was purged with nitrogen then purged with hydrogen, and the mixture was stirred under hydrogen (1 atm) at room temperature for 3 hours. The flask was purged with nitrogen and the reaction mixture was filtered. The filtrate was concentrated under vacuum, and the residue was purified by reverse-phase HPLC [Waters XBridge™ RP18 column, 5 μm, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (300 MHz, methanol-$d_4$) δ ppm 2.01-2.10 (m, 4H), 2.41 (s, 3H), 2.97-3.13 (m, 3H), 3.21-3.26 (m, 2H), 26 (s, 2H), 6.69 (d, J=12.2 Hz, 1H), 6.88-6.90 (m, 2H), 6.99 (d, J=11.9 Hz, 1H), 7.04 (d, J=8.1 Hz, 1H), 7.21-7.26 (m, 1H) 7.44 (dd, J=8.2, 2.0 Hz, 1H), 8.16 (d, J=2.4 Hz, 1H); MS (APCI) m/z 330 (M+H)+.

Example 32

9-[(E)-2-(6-methylpyridin-3-yl)vinyl]-3,4,5,10-tetrahydro-1H-2,5-ethanoazepino[3,4-b]indole Example 32A 9-bromo-3,4,5,10-tetrahydro-1H-2,5-ethanoazepino[3,4-b]indole Crude reaction mixture was obtained as described in Example 1B. Analytical HPLC analysis [Phenomenex® Luna® Combi-HTS C8 (2) 5 μm 100 Å (2.1×30 mm), a gradient of 10-100% acetonitrile (A) and 0.1% trifluoroacetic acid in water (B) at a flow rate of 2.0 mL/minute over 3 minutes (0-0.1 minute 10% A, 0.1-2.6 minutes 10-100% A)] identified the product of Example 1B as the major product (retention time 1.77 minutes) and the title compound as the minor product (retention time 1.95 minutes). The crude reaction mixture was dissolved in dimethyl sulfoxide and then was purified by reverse-phase HPLC (Waters XBridge™ C18 5 μm OBD 30×100 mm column, flow rate 40 mL/minute, 20-99% gradient of methanol in water with 0.1% trifluoroacetic acid over 20 minutes) to afford a major fraction containing the product of Example 1B and a minor fraction containing the title compound. The fractions containing the title compound were combined and partitioned between $CHCl_3$/2-propanol (4:1, 2×200 mL) and 1.0 M sodium carbonate (200 mL). The combined organic extracts were dried (sodium sulfate) and concentrated under vacuum to afford the title compound: $^1$H NMR (400 MHz, methanol-$d_4$) δ ppm 1.92-2.13 (m, 4 H), 2.99-3.10 (m, 2 H), 3.19-3.28 (m, 3 H), 4.28 (s, 2 H), 6.88 (t, J=7.8 Hz, 1 H), 7.17 (dd, J=7.6, 0.6 Hz, 1 H), 7.38 (d, J=7.9 Hz, 1 H); MS (APCI) m/z 291/293 (M+H)+.

Example 32B

9-[(E)-2-(6-methylpyridin-3-yl)vinyl]-3,4,5,10-tetrahydro-1H-2,5-ethanoazepino[3,4-b]indole The product of Example 17B (105 mg, 0.43 mmol) and the product of Example 32A (125 mg, 0.43 mmol) were processed as described in Example 4 to provide the title compound: $^1$H NMR (400 MHz, methanol-$d_4$) δ ppm 1.95-2.14 (m, 4 H), 2.54 (s, 3 H), 3.02-3.12 (m, 2 H), 3.21-3.30 (m, 3 H), 4.32 (s, 2 H), 7.02 (t, J=7.6 Hz, 1 H), 7.22 (d, J=16.5 Hz, 1 H), 7.30 (d, J=8.2 Hz, 1 H), 7.36 (d, J=7.3 Hz, 1 H), 7.37 (d, J=7.9 Hz, 1 H), 7.65 (d, J=16.2 Hz, 1 H), 8.01 (dd, J=8.1, 2.3 Hz, 1 H), 8.60 (d, J=2.4 Hz, 1H); MS (APCI) m/z 330 (M+H)+.

Example 33

9-[2-(6-methylpyridin-3-yl)ethyl]-3,4,5,10-tetrahydro-1H-2,5-ethanoazepino[3,4-b]indole The product of Example 32B (80 mg, 0.24 mmol) was processed as described in Example 2 to provide the title compound: $^1$H NMR (300 MHz, methanol-$d_4$) δ ppm 1.91-2.16 (m, 4 H), 2.46 (s, 3 H), 2.93-3.04 (m, 3 H), 3.04-3.14 (m, 3 H), 3.20-3.28 (m, 3 H), 4.27 (s, 2 H), 6.74 (d, J=7.1 Hz, 1 H), 6.83-6.91 (m, 1 H), 7.15 (d, J=7.8 Hz, 1 H), 7.25 (dd, J=8.0, 0.8 Hz, 1 H), 7.51 (dd, J=7.8, 2.4 Hz, 1H), 8.13 (d, J=2.0 Hz, 1 H); MS (APCI) m/z 332 (M+H)+.

Example 34

7-[(E)-2-pyridin-3-ylvinyl]-3,4,5,6-tetrahydro-1H-2,5-ethanoazepino[4,3-b]indole A mixture of bis(tri-t-butylphosphino)palladium (18.4 mg, 0.036 mmol; Strem), 3-vinylpyridine (123 mg, 0.52 mmol; TCI-US), sodium t-butoxide (87 mg, 0.90 mmol; Aldrich) and the product of Example 1B (105 mg, 0.36 mmol) was combined with 1,4-dioxane (2 mL). The mixture was purged with a stream of nitrogen for 2 minutes, then stirred at 85° C. in a sealed tube. After 18 hours, the reaction mixture was cooled to ambient temperature. Magnesium sulfate (43 mg, 0.36 mmol) and 3-vinylpyridine (85 mg, 0.36 mmol; TCI- US) were added and the reaction mixture was again purged with nitrogen, sealed and stirred at 100° C. for 24 hour in a sealed tube. The reaction mixture was cooled to ambient temperature, filtered through a glass microfiber frit, rinsed with methanol (2 mL) and purified by reverse-phase HPLC [Waters XBridge™ RP18 column, 5 μm, 30×100 mm, flow rate 40 mL/minute, 30-100% gradient of methanol in buffer (0.1 M aqueous ammonium bicarbonate, adjusted to pH 10 with ammonium hydroxide)] to afford the title compound: $^1$H NMR (400 MHz, methanol-$d_4$) δ ppm 2.01-2.18 (m, 4 H), 3.02-3.12 (m, 2 H), 3.14 (pent, J=3.4 Hz, 1 H), 3.20-3.29 (m, 2 H), 4.23 (s, 2 H), 7.03 (t, J=7.6 Hz, 1 H), 7.25 (d, J=16.5 Hz, 1 H), 7.27 (d, J=7.3 Hz, 1 H), 7.41 (d, J=7.3 Hz, 1 H), 7.43 (dd, J=8.2, 4.9 Hz, 1 H), 7.74 (d, J=16.5 Hz, 1 H), 8.07-8.15 (m, 1 H), 8.38 (dd, J=4.6, 0.9 Hz, 1 H), 8.75 (d, J=1.5 Hz, 1H); MS (APCI) m/z 316 (M+H)$^+$.

Example 35

8-[(E)-2-(6-methylpyridin-3-yl)vinyl]-1,3,4,5,6,7-hexahydro-2,6-methanoazocino[4,3-b]indole

Example 35A ethyl 1-(3-ethoxy-3-oxopropyl)piperidine-3-carboxylate

A 25 mL round-bottom flask was charged with ethyl nipecotate (8.0 mL, 51.5 mmol, Aldrich) and ethyl acrylate (6.0 mL, 55.4 mmol, Aldrich). The flask was purged with nitrogen and the mixture was heated to 80° C. for 20 hours. The excess ethyl acrylate was removed under reduced pressure. The remaining residue was purified by distillation (0.9 Ton, 122° C.) to provide the title compound: $^1$H NMR (400 MHz, CDCl$_3$) δ ppm 1.23-1.27 (m, 6H), 1.41-1.59 (m, 2H), 1.69-1.74 (m, 1H), 1.90-1.94 (m, 1H), 2.05 (td, J=10.9, 2.9 Hz, 1H), 2.05 (t, J=10.7 Hz, 1H), 2.46-2.56 (m, 3H), 2.69-2.76 (m, 3H), 2.95-2.98 (m, 1H), 4.10-4.16 (m, 4H); $^{13}$C NMR (100 MHz, CDCl$_3$) δ ppm 14.14, 14.15, 24.51, 26.78, 32.61, 41.80, 53.37, 53.79, 55.12, 60.28, 60.23, 172.50, 174.03; MS (DCI/NH$_3$) m/z 258 (M+H)$^+$.

Example 35B

1-azabicyclo[3.3.1]nonan-4-one

A suspension of potassium tert-butoxide (12.03 g, 107 mmol; Aldrich) in toluene (200 mL) was heated to reflux for 15 minutes, then a solution of ethyl 1-(3-ethoxy-3-oxopropyl) piperidine-3-carboxylate (10.70 g, 41.6 mmol; Example 35A) in toluene (50 mL) was added dropwise over 2 hour to the refluxing reaction mixture. After the addition was complete, the reaction was heated to reflux for an additional 2 hours, cooled to ambient temperature, and extracted with water (3×50 mL). The combined aqueous layers were acidified with concentrated hydrochloric acid (40 mL), then heated to reflux for 22 hours. The reaction was basified with 45 weight % potassium hydroxide (~35 mL) and extracted with chloroform (3×100 mL). The combined organic extracts were dried over sodium sulfate, filtered and concentrated in vacuo to afford the title compound: $^1$H NMR (300 MHz, CDCl$_3$) δ ppm 1.50-1.81 (m, 2 H), 1.90-1.96 (m, 2 H), 2.39-2.43 (m, 1 H), 2.49-2.54 (m, 2 H), 3.08-3.41 (m, 6 H); MS (DCI/NH$_3$) m/z 140 (M+H)$^+$.

Example 35C

8-bromo-1,3,4,5,6,7-hexahydro-2,6-methanoazocino [4,3-b]indole

1-Azabicyclo[3.3.1]nonan-4-one (1.38 g, 9.91 mmol; Example 35B) and 3-bromophenylhydrazine hydrochloride (2.23 g, 9.98 mmol; Aldrich) were suspended in 1 M HCl in acetic acid (30 mL; Aldrich). The reaction mixture was heated to 80° C. for 5 hours to give a solution. The reaction was allowed to cool to ambient temperature and concentrated under vacuum. The residue was suspended in acetonitrile (20 mL), which was briefly heated to reflux and then cooled to ambient temperature. The suspended solid was isolated by filtration and washed with additional acetonitrile (10×2 mL) to provide a solid (3.03 g). This material was dissolved in 1 M NaOH (50 mL) and extracted with chloroform (3×50 mL). The combined organic layers were dried over sodium sulfate, filtered and concentrated in vacuo to afford the title compound: $^1$H NMR (300 MHz, CDCl$_3$) δ ppm 1.26-1.30 (m, 1H), 1.40-1.51 (m, 1H), 1.84-1.98 (m, 2H), 2.99-3.16 (m, 4H), 3.22-3.26 (m, 1H), 3.90 (d, J=16.3 Hz, 1H), 4.33 (d, J=16.3 Hz, 1H), 6.90 (t, J=7.8 Hz, 1H), 7.21 (dd, J=7.6, 0.9 Hz, 1H), 7.35 (dd, J=7.8, 1.0 Hz, 1H); MS (DCI/NH$_3$) m/z 291 (M+H)$^+$. Anal. Calcd. for $C_{14}H_{15}BrN_2$: C, 57.75; H, 5.19; N, 9.62. Found: C, 57.84; H, 5.33; N, 9.47.

Example 35D

8-[(E)-2-(6-methylpyridin-3-yl)vinyl]-1,3,4,5,6,7-hexahydro-2,6-methanoazocino[4,3-b]indole The product of Example 35C (150.4 mg, 0.517 mmol) and the product of Example 17B (176.3 mg, 0.719 mmol) were processed according to the method described in Example 4. Purification by reverse-phase HPLC [Waters XBridge™ RP18 column, 5 μm, 30×100 mm, flow rate 40 mL/minute, 20-99% gradient of methanol in buffer (0.1 M aqueous ammonium bicarbonate, adjusted to pH 10 with ammonium hydroxide)] provided the title compound: $^1$H NMR (300 MHz, methanol-$d_4$) δ ppm 1.53-1.60 (m, 2H), 1.91-2.03 (m, 2H), 2.55 (s, 3H), 3.33-3.54 (m, 5H), 4.27 (d, J=15.9 Hz, 1H), 4.65 (d, J=15.9 Hz, 1H), 7.09 (t, J=7.6 Hz, 1H), 7.27 (d, J=16.3 Hz, 1H), 7.32 (d, J=8.1 Hz, 1H), 7.38 (dd, J=7.8, 0.7 Hz, 1H), 7.48 (d, J=7.5 Hz, 1H), 7.69 (d, J=16.3 Hz, 1H), 8.02 (dd, J=8.1, 2.0 Hz, 1H); MS (DCI/NH$_3$) m/z 330 (M+H)$^+$.

Example 36

(cis)-7-[(E)-2-(6-methylpyridin-3-yl)vinyl]-3,4,5,5a,6,10b-hexahydro-1H-2,5-ethanoazepino[4,3-b]indole The product of Example 1D (100 mg, 0.30 mmol) was dissolved in trifluoroacetic acid (3.0 mL) and stirred at −30° C. A solution of sodium cyanoborohydride (120 mg, 1.82 mmol; Acros) in methanol (1.0 mL) was added dropwise over a period of 30 minutes. The reaction mixture was allowed to slowly warm up to ambient temperature over a period of 30 minutes and then stirred at 25° C. for 1 hour. Methanol (30 mL) was added to the reaction and concentrated under vacuum (repeated twice). The crude product was re-dissolved in methanol and purified by reverse-phase HPLC [Waters XBridge™ RP18 column, 5 μm, 30×100 mm, flow rate 40 mL/minute, 20-60% gradient of methanol in buffer (0.1 M aqueous ammonium bicarbonate, adjusted to pH 10 with ammonium hydroxide)] to afford the title compound: $^1$H NMR (400 MHz, methanol-$d_4$) δ ppm 1.53-1.64 (m, 1 H), 1.87-1.96 (m, 2 H), 2.18-2.28 (m, 1 H), 2.38-2.49 (m, 1 H), 2.51 (s, 3 H), 2.80-2.87 (m, 2 H), 2.90-3.01 (m, 2 H), 3.09-3.19 (m, 1 H), 3.24-3.29 (m, 1 H), 3.54-3.64 (m, 1 H), 4.19 (dd, J=8.9, 4.9 Hz, 1 H), 6.63 (t, J=7.5 Hz, 1 H), 6.88-6.93 (m, J=7.3 Hz, 1 H), 7.00 (d, J=16.2 Hz, 1 H), 7.24-7.35 (m, 3 H), 7.94 (dd, J=8.1, 2.3 Hz, 1 H), 8.52 (d, J=2.1 Hz, 1 H); MS (ESI+) m/z 332 (M+H)$^+$.

Example 37

7-(6-methylpyridin-3-yl)-3,4,5,6-tetrahydro-1H-2,5-ethanoazepino[4,3-b]indole

The product of Example 1B (123 mg, 0.42 mmol) and 6-methylpyridine-3-boronic acid pinacol ester (111 mg, 0.51 mmol; Synthonix) were processed as described in Example 4 to provide the title compound: $^1$H NMR (400 MHz, methanol-d$_4$) δ ppm 2.01-2.17 (m, 4 H), 2.60 (s, 3 H), 3.03-3.14 (m, 3 H), 3.20-3.29 (m, 2 H), 4.27 (s, 2 H), 7.03-7.06 (m, 1 H), 7.10 (t, J=7.6 Hz, 1 H), 7.34 (dd, J=7.6, 1.2 Hz, 1 H), 7.42 (d, J=8.2 Hz, 1 H), 7.96 (dd, J=7.9, 2.4 Hz, 1 H), 8.63 (d, J=2.1 Hz, 1 H); MS (APCI) m/z 304 (M+H)$^+$.

Example 38

7-(pyrimidin-5-yl)-3,4,5,6-tetrahydro-1H-2,5-ethanoazepino[4,3-b]indole

The product of Example 1B (100 mg, 0.32 mmol) and pyrimidine-5-boronic acid (64 mg, 0.52 mmol; MayBridge) were processed as described in Example 4 to provide the title compound: $^1$H NMR (500 MHz, methanol-d$_4$) δ ppm 2.01-2.17 (m, 4 H), 2.60 (s, 3 H), 3.03-3.14 (m, 3 H), 3.20-3.29 (m, 2 H), 4.27 (s, 2 H), 7.03-7.06 (m, 1 H), 7.10 (t, J=7.6 Hz, 1 H), 7.34 (dd, J=7.6, 1.2 Hz, 1 H), 7.42 (d, J=8.2 Hz, 1 H), 7.96 (dd, J=7.9, 2.4 Hz, 1 H), 8.63 (d, J=2.1 Hz, 1 H); MS (ESI+) m/z 291 (M+H)$^+$.

Example 39

7-(pyridin-3-yl)-3,4,5,6-tetrahydro-1H-2,5-ethanoazepino[4,3-b]indole

The product of Example 1B (80 mg, 0.28 mmol) and pyridine-3-boronic acid (36 mg, 0.29 mmol; Aldrich) were processed as described in Example 4 to provide the title compound: $^1$H NMR (300 MHz, methanol-d$_4$) δ ppm 2.00-2.14 (m, 4 H), 3.01-3.15 (m, 3 H), 3.20-3.28 (m, 2 H), 4.27 (s, 2 H), 7.04-7.09 (m, 1 H), 7.12 (t, J=7.3 Hz, 1 H), 7.37 (dd, J=7.5, 1.4 Hz, 1 H), 7.56 (dd, J=7.8, 5.1 Hz, 1 H), 8.05-8.12 (m, 1 H), 8.55 (dd, J=4.9, 1.5 Hz, 1H), 8.77-8.79 (m, 1 H); MS (ESI+) m/z 290 (M+H)$^+$.

Example 40

7-(pyridin-4-yl)-3,4,5,6-tetrahydro-1H-2,5-ethanoazepino[4,3-b]indole

The product of Example 1B (100 mg, 0.34 mmol) and pyridine-4-boronic acid (52 mg, 0.38 mmol; Aldrich) were processed as described in Example 4 to provide the title compound: $^1$H NMR (400 MHz, methanol-d$_4$) δ ppm 2.06-2.17 (m, 4 H), 3.06-3.18 (m, 3 H), 3.23-3.29 (m, 2 H), 4.30 (s, 2 H), 7.13 (t, J=7.6 Hz, 1 H), 7.17-7.20 (m, 1 H), 7.41 (dd, J=7.6, 1.2 Hz, 1 H), 7.70-7.74 (m, 2 H), 8.58-8.64 (m, 2 H); MS (APCI) m/z 290 (M+H)$^+$.

Example 41

7-(quinolin-3-yl)-3,4,5,6-tetrahydro-1H-2,5-ethanoazepino[4,3-b]indole

A suspension of the product of Example 1B (150 mg, 0.52 mmol), 3-quinolineboronic acid (102 mg, 0.59 mmol; Aldrich), dichlorobis(triphenylphosphine)palladium (II) (18 mg, 0.026 mmol; Aldrich) and 1.0 M sodium carbonate (1.3 mL) in 2-propanol (3.8 mL) was purged with nitrogen and then stirred at 80° C. for 1 hour in a sealed tube. The reaction mixture was cooled and partitioned between CHCl$_3$ (2×30 mL) and 1.0 M sodium carbonate (50 mL). The combined organic extracts were dried (sodium sulfate) and concentrated under vacuum. The resulting residue was purified by reverse-phase HPLC [Waters XBridge™RP18 column, 5 µm, 30×100 mm, flow rate 40 mL/minute, 40-100% gradient of methanol in buffer (0.1 M aqueous ammonium bicarbonate, adjusted to pH 10 with ammonium hydroxide)] to afford the title compound: $^1$H NMR (400 MHz, methanol-d$_4$) δ ppm 1.98-2.16 (m, 4 H), 3.02-3.14 (m, 3 H), 3.25 (ddd, J=14.1, 8.8, 5.5 Hz, 2 H), 4.28 (s, 2 H), 7.12-7.22 (m, 2 H), 7.39 (dd, J=7.3, 1.5 Hz, 1 H), 7.66 (ddd, J=8.1, 7.0, 1.1 Hz, 1 H), 7.79 (ddd, J=8.5, 6.9, 1.4 Hz, 1 H), 8.03 (dd, J=8.2, 0.9 Hz, 1 H), 8.09 (d, J=8.5 Hz, 1 H), 8.57 (d, J=2.1 Hz, 1 H), 9.09 (d, J=2.1 Hz, 1 H); MS (ESI+) m/z 340 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:
1. A compound of formula (I-a):

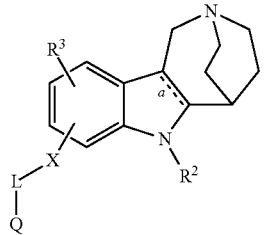

or a pharmaceutically acceptable salt thereof, wherein
a is a single or double bond;
X is O, S, S(O), S(O)$_2$, or a bond;
L is —[C(R$^a$)(R$^b$)]$_p$—, —[C(R$^a$)(R$^b$)]$_{q1}$—[(CR$^c$)═(CR$^d$)]—[C(R$^a$)(R$^b$)]$_{q2}$—, —[C(R$^a$) (R$^b$)]$_{r1}$—[C≡C]—[C(R$^a$)(R$^b$)]$_{r2}$—, —[C(R$^a$) (R$^b$)]$_s$-cyclopropylene-[C(R$^a$)(R$^b$)]$_t$—, or a bond; or
X and L taken together are a bond;
Q is substituted or unsubstituted monocyclic aryl, substituted or unsubstituted bicyclic aryl, substituted or unsubstituted monocyclic heteroaryl, or substituted or unsubstituted bicyclic heteroaryl;
R$^2$ is hydrogen, C$_1$-C$_4$ alkyl, C$_2$-C$_4$ alkenyl, or C$_2$-C$_4$ alkynyl, wherein C$_1$-C$_4$ alkyl, and the saturated carbon atoms of $C_2$-$C_4$ alkenyl and $C_2$-$C_4$ alkynyl, can be unsubstituted or substituted by hydroxyl, $C_1$-$C_8$ alkyl, $C_1$-$C_8$ haloalkyl, carboxy, or alkoxycarbonyl;

$R^3$ is hydrogen, halogen, $C_1$-$C_5$ haloalkyl, $C_1$-$C_5$ alkoxy, $C_1$-$C_5$ haloalkoxy, or cyano;

$R^a$, $R^b$, $R^c$, and $R^d$ are, at each occurrence, independently hydrogen, halogen, $C_1$-$C_8$ alkyl, $C_1$-$C_8$ haloalkyl, carboxy, or alkoxycarbonyl;

p is 1, 2, 3, 4, or 5;

q1 and q2 are independently 0, 1, 2, or 3, provided that the sum of q1 and q2 is 0, 1, 2, or 3;

r1 and r2 are independently 0, 1, 2, or 3, provided that the sum of r1 and r2 is 0, 1, 2, or 3;

s is 0, 1 or 2; and t is 0 or 1;

wherein Q, when substituted, is independently substituted with 1, 2, 3, 4, or 5 substituents, wherein the substituent is halogen, cyano, $C_1$-$C_5$ haloalkyl, $C_1$-$C_5$ alkyl, $C_2$-$C_5$ alkenyl, $C_2$-$C_5$ alkynyl, hydroxy, $C_1$-$C_5$ alkoxy, —O—$C_1$-$C_5$ haloalkyl, —S—$C_1$-$C_5$ alkyl, —S—$C_1$-$C_5$ haloalkyl, —$SO_2$—$C_1$-$C_5$ alkyl, —$SO_2$—$C_1$-$C_5$ haloalkyl, $C_1$-$C_5$ cyanoalkyl, or —$NO_2$.

2. The compound of claim 1, wherein L is —[C($R^a$)($R^b$)]$_p$—.

3. The compound of claim 2, wherein $R^2$ is hydrogen.

4. The compound of claim 2, wherein $R^2$ is $C_1$-$C_4$ alkyl.

5. The compound of claim 2, wherein $R^2$ is $C_2$-$C_4$ alkenyl.

6. The compound of claim 2, wherein $R^2$ is $C_2$-$C_4$ alkynyl.

7. The compound of claim 1, wherein L is —[C($R^a$)($R^b$)]$_{q1}$—[(C$R^c$)=(C$R^d$)]—[C($R^a$)($R^b$)]$_{q2}$—.

8. The compound of claim 7, wherein $R^2$ is hydrogen.

9. The compound of claim 7, wherein $R^2$ is $C_1$-$C_4$ alkyl.

10. The compound of claim 7, wherein $R^2$ is $C_2$-$C_4$ alkenyl.

11. The compound of claim 7, wherein $R^2$ is $C_2$-$C_4$ alkynyl.

12. The compound of claim 1, wherein L is —[C($R^a$)($R^b$)]$_{r1}$—[C≡C]—[C($R^a$)($R^b$)]$_{r2}$—.

13. The compound of claim 12, wherein $R^2$ is hydrogen.

14. The compound of claim 12, wherein $R^2$ is $C_1$-$C_4$ alkyl.

15. The compound of claim 12, wherein $R^2$ is $C_2$-$C_4$ alkenyl.

16. The compound of claim 12, wherein $R^2$ is $C_2$-$C_4$ alkynyl.

17. The compound of claim 1, wherein X and L taken together are a bond.

18. The compound of claim 17, wherein $R^2$ is hydrogen.

19. The compound of claim 17, wherein $R^2$ is $C_1$-$C_4$ alkyl.

20. The compound of claim 17, wherein $R^2$ is $C_2$-$C_4$ alkenyl.

21. The compound of claim 17, wherein $R^2$ is $C_2$-$C_4$ alkynyl.

22. The compound of claim 1, wherein $R^3$ is hydrogen.

23. The compound of claim 1, wherein $R^3$ is halogen.

24. The compound of claim 1, wherein $R^3$ is $C_1$-$O_5$ haloalkyl.

25. The compound of claim 1, wherein $R^3$ is $C_1$-$C_5$ alkoxy, $C_1$-$C_5$ haloalkoxy, or cyano.

26. A compound of formula (III-a) or formula (III-c):

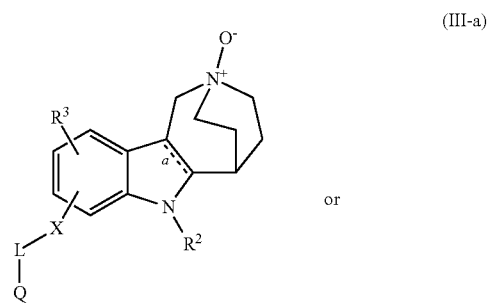

(III-a)

or

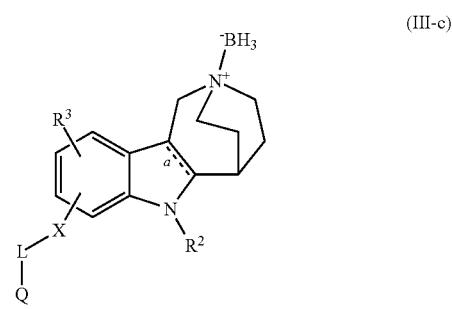

(III-c)

or a pharmaceutically acceptable salt thereof, wherein a, $R^2$, $R^3$, X, L, and Q are as defined in claim 1.

27. The compound according to claim 1, or a pharmaceutically acceptable salt thereof, selected from the group consisting of:

7-[(E)-2-(6-methylpyridin-3-yl)vinyl]-3,4,5,6-tetrahydro-1H-2,5-ethanoazepino[4,3-b]indole;

7-[2-(6-methylpyridin-3-yl)ethyl]-3,4,5,6-tetrahydro-1H-2,5-ethanoazepino[4,3-b]indole;

7-[(6-methylpyridin-3-yl)ethynyl]-3,4,5,6-tetrahydro-1H-2,5-ethanoazepino[4,3-b]indole;

7-[(E)-2-(4-chlorophenyl)vinyl]-3,4,5,6-tetrahydro-1H-2,5-ethanoazepino[4,3-b]indole;

7-[(1E)-5-phenylpent-1-enyl]-3,4,5,6-tetrahydro-1H-2,5-ethanoazepino[4,3-b]indole;

7-[(E)-2-thien-3-ylvinyl]-3,4,5,6-tetrahydro-1H-2,5-ethanoazepino[4,3-b]indole;

7-(5-phenylpentyl)-3,4,5,6-tetrahydro-1H-2,5-ethanoazepino[4,3-b]indole;

9-[(E)-2-(6-methylpyridin-3-yl)vinyl]-3,4,5,6-tetrahydro-1H-2,5-ethanoazepino[4,3-b]indole;

9-[2-(6-methylpyridin-3-yl)ethyl]-3,4,5,6-tetrahydro-1H-2,5-ethanoazepino[4,3-b]indole;

7-[(E)-2-(4-fluorophenyl)vinyl]-3,4,5,6-tetrahydro-1H-2,5-ethanoazepino[4,3-b]indole;

7-[(E)-2-pyridin-4-ylvinyl]-3,4,5,6-tetrahydro-1H-2,5-ethanoazepino[4,3-b]indole;

7-[(E)-2-pyridin-2-ylvinyl]-3,4,5,6-tetrahydro-1H-2,5-ethanoazepino[4,3-b]indole;

7-(pyridin-3-ylethynyl)-3,4,5,6-tetrahydro-1H-2,5-ethanoazepino[4,3-b]indole;

7-[(E)-2-(2,4-difluorophenyl)vinyl]-3,4,5,6-tetrahydro-1H-2,5-ethanoazepino[4,3-b]indole;

7-[(E)-2-(3-fluorophenyl)vinyl]-3,4,5,6-tetrahydro-1H-2,5-ethanoazepino[4,3-b]indole;

7-[2-(3-fluorophenyl)ethyl]-3,4,5,6-tetrahydro-1H-2,5-ethanoazepino[4,3-b]indole;

8-[(E)-2-(6-methylpyridin-3-yl)vinyl]-3,4,5,6-tetrahydro-1H-2,5-ethanoazepino[4,3-b]indole;

10-[(E)-2-(6-methylpyridin-3-yl)vinyl]-3,4,5,6-tetrahydro-1H-2,5-ethanoazepino[4,3-b]indole;

7-[(E)-2-phenylvinyl]-3,4,5,6-tetrahydro-1H-2,5-ethanoazepino[4,3-b]indole;
7-{[4-(trifluoromethoxy)phenyl]ethynyl}-3,4,5,6-tetrahydro-1H-2,5-ethanoazepino[4,3-b]indole;
7-(pyridin-4-ylethynyl)-3,4,5,6-tetrahydro-1H-2,5-ethanoazepino[4,3-b]indole;
8-[(6-methylpyridin-3-yl)ethynyl]-3,4,5,6-tetrahydro-1H-2,5-ethanoazepino[4,3-b]indole;
10-[(6-methylpyridin-3-yl)ethynyl]-3,4,5,6-tetrahydro-1H-2,5-ethanoazepino[4,3-b]indole;
9-fluoro-7-[(6-methylpyridin-3-yl)ethynyl]-3,4,5,6-tetrahydro-1H-2,5-ethanoazepino[4,3-b]indole;
9-fluoro-7-[(E)-2-(6-methylpyridin-3-yl)vinyl]-3,4,5,6-tetrahydro-1H-2,5-ethanoazepino[4,3-b]indole;
7-(benzyloxy)-3,4,5,6-tetrahydro-1H-2,5-ethanoazepino[4,3-b]indole;
7-quinolin-6-yl-3,4,5,6-tetrahydro-1H-2,5-ethanoazepino[4,3-b]indole;
7-[(E)-2-pyrimidin-5ylvinyl]-3,4,5,6-tetrahydro-1H-2,5-ethanoazepino[4,3-b]indole;
7-[(Z)-2-pyrimidin-5-ylvinyl]-3,4,5,6-tetrahydro-1H-2,5-ethanoazepino[4,3-b]indole;
7-[(Z)-2-(6-methylpyridin-3-yl)vinyl]-3,4,5,6-tetrahydro-1H-2,5-ethanoazepino[4,3-b]indole;
7-[(E)-2-pyridin-3-ylvinyl]-3,4,5,6-tetrahydro-1H-2,5-ethanoazepino[4,3-b]indole;
(cis)-7-[(E)-2-(6-methylpyridin-3-yl)vinyl]-3,4,5,5a,6,10b-hexahydro-1H-2,5-ethanoazepino[4,3-b]indole;
7-(6-methylpyridin-3-yl)-3,4,5,6-tetrahydro-1H-2,5-ethanoazepino[4,3-b]indole;
7-(pyrimidin-5-yl)-3,4,5,6-tetrahydro-1H-2,5-ethanoazepino[4,3-b]indole;
7-(pyridin-3-yl)-3,4,5,6-tetrahydro-1H-2,5-ethanoazepino[4,3-b]indole;
7-(pyridin-4-yl)-3,4,5,6-tetrahydro-1H-2,5-ethanoazepino[4,3-b]indole; and
7-(quinolin-3-yl)-3,4,5,6-tetrahydro-1H-2,5-ethanoazepino[4,3-b]indole.

28. A pharmaceutical composition comprising a therapeutically effective amount of a compound of formula (I-a) according to claim 1 or formula (III-a) or formula (III-c) according to claim 26.

29. A pharmaceutical composition comprising a therapeutically effective amount of a compound of formula (I-a) according to claim 1 or a compound of formula (III-a) or formula (III-c) according to claim 26 or a pharmaceutically acceptable salt thereof, in combination with a pharmaceutically acceptable carrier.

30. A compound according to claim 26 that is 7-[(E)-2-(6-methylpyridin-3-yl)vinyl]-1,2,3,4,5,6-hexahydro-2,5-ethanoazepino[4,3-b]indole 2-oxide, or a pharmaceutically acceptable salt thereof.

* * * * *